(12) United States Patent
Kaneko et al.

(10) Patent No.: US 11,656,384 B2
(45) Date of Patent: May 23, 2023

(54) COMPOSITION, FILM, LENS, SOLID STATE IMAGING ELEMENT, AND COMPOUNDS

(71) Applicant: FUJIFILM Corporation, Tokyo (JP)

(72) Inventors: Yushi Kaneko, Shizuoka (JP); Yoshinori Taguchi, Shizuoka (JP); Hirotaka Takishita, Shizuoka (JP); Masahiro Mori, Shizuoka (JP); Yasuhiro Sawamura, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 478 days.

(21) Appl. No.: 16/713,234

(22) Filed: Dec. 13, 2019

(65) Prior Publication Data

US 2020/0116896 A1 Apr. 16, 2020

Related U.S. Application Data

(63) Continuation of application No. PCT/JP2018/022539, filed on Jun. 13, 2018.

(30) Foreign Application Priority Data

Jun. 14, 2017 (JP) ................. 2017-117168

(51) Int. Cl.
| | | |
|---|---|---|
| C07D 251/70 | (2006.01) | |
| G02B 1/04 | (2006.01) | |
| C07C 233/65 | (2006.01) | |
| C07C 257/06 | (2006.01) | |
| C07C 311/21 | (2006.01) | |
| C07C 323/47 | (2006.01) | |
| C07D 209/60 | (2006.01) | |
| C07D 209/88 | (2006.01) | |
| C07D 251/52 | (2006.01) | |
| C07D 401/12 | (2006.01) | |
| C07D 417/12 | (2006.01) | |
| C07D 491/048 | (2006.01) | |
| C07D 513/04 | (2006.01) | |
| H04N 25/00 | (2023.01) | |

(52) U.S. Cl.
CPC ............ *G02B 1/041* (2013.01); *C07C 233/65* (2013.01); *C07C 257/06* (2013.01); *C07C 311/21* (2013.01); *C07C 323/47* (2013.01); *C07D 209/60* (2013.01); *C07D 209/88* (2013.01); *C07D 251/52* (2013.01); *C07D 251/70* (2013.01); *C07D 401/12* (2013.01); *C07D 417/12* (2013.01); *C07D 491/048* (2013.01); *C07D 513/04* (2013.01); *H04N 25/00* (2023.01)

(58) Field of Classification Search
CPC .......................... C07D 251/54; C07D 251/70
See application file for complete search history.

(56) References Cited

U.S. PATENT DOCUMENTS

| | | | | |
|---|---|---|---|---|
| 6,476,892 B2 * | 11/2002 | Aminaka | .......... | G02F 1/133634 |
| | | | | 349/96 |
| 7,375,222 B2 * | 5/2008 | Kubota | ................ | C07D 403/12 |
| | | | | 544/197 |
| 8,017,199 B2 * | 9/2011 | Fukagawa | .................. | C08J 5/18 |
| | | | | 349/120 |
| 2002/0039627 A1 | 4/2002 | Ichihashi et al. | | |
| 2003/0085387 A1 * | 5/2003 | Fujiyama | ............... | C08K 5/378 |
| | | | | 252/582 |
| 2017/0342091 A1 | 11/2017 | Hirai et al. | | |

FOREIGN PATENT DOCUMENTS

| | | |
|---|---|---|
| JP | 2002-20363 A | 1/2002 |
| JP | 2003-66225 A | 3/2003 |
| JP | 2004-53981 A | 2/2004 |
| JP | 2006-96875 A | 4/2006 |
| JP | 2009-222994 A | 10/2009 |
| JP | 2011-53594 A | 3/2011 |
| JP | 2011-81032 A | 4/2011 |
| JP | 2011-90052 A | 5/2011 |
| JP | 2013-61465 A | 4/2013 |
| JP | 2014-98101 A | 5/2014 |
| TW | 526225 B | 4/2003 |
| WO | WO 01/49686 A1 * | 7/2001 |
| WO | WO 01/92925 A1 | 12/2001 |
| WO | WO 2016/136786 A1 | 9/2016 |
| WO | WO 2018/235549 A1 * | 12/2018 |

OTHER PUBLICATIONS

CAPLUS Abstract 43:3748 (1949).*
Honda, CAPLUS Abstract 58:27332 (1963).*
Ciba Ltd., CAPLUS Abstract 66:7111 (1967).*
Kitamura et al., CAPLUS Abstract 123:259916 (1995).*
Registry RN 1027564-68-6 (2008).*
Machine Translation of WO 2018/235549, 58 pages, (publication date: 2018).*
International Preliminary Report on Patentability and Written Opinion of the International Searching Authority (Forms PCT/IB/326, PCT/IB/373, PCT/ISA/237), dated Dec. 26, 2019, for International Application No. PCT/JP2018/022539, with an English translation.

(Continued)

*Primary Examiner* — Deepak R Rao
(74) *Attorney, Agent, or Firm* — Birch, Stewart, Kolasch & Birch, LLP

(57) ABSTRACT

An object of the present invention is to provide a composition capable of forming a film having a high refractive index and excellent exterior characteristics. Another object of the present invention is to provide a film, a lens, and a solid-state imaging element in which the composition is used. Still another object of the present invention is to provide novel compounds.

The composition according to an embodiment of the present invention contains a compound represented by General Formula (I), a solvent, and a resin, in which a solubility of the compound represented by General Formula (I) in the solvent is less than 0.5% by mass at 25° C., and a maximum absorption wavelength of the compound represented by General Formula (I) at a wavelength range of 300 to 800 nm is equal to or shorter than 450 nm.

$$A\text{-}(\text{-}B\text{-}C)_n \qquad (I)$$

14 Claims, No Drawings

(56) References Cited

OTHER PUBLICATIONS

International Search Report (Form PCT/ISA/210), dated Sep. 18, 2818, for International Application No. PCT/JP2018/022539, with an English translation.
Japanese Office Action for corresponding Japanese Application No. 2019-525478, dated Jan. 5, 2021.
Taiwanese Office Action and Search Report dated Oct. 25, 2021 for corresponding Application 107120529 with an English translation of the Office Action.

\* cited by examiner

COMPOSITION, FILM, LENS, SOLID STATE IMAGING ELEMENT, AND COMPOUNDS

CROSS-REFERENCE TO RELATED APPLICATIONS

This application is a Continuation of PCT International Application No. PCT/JP2018/022539 filed on Jun. 13, 2018, which claims priority under 35 U.S.C. § 119(a) to Japanese Patent Application No. 2017-117168 filed on Jun. 14, 2017. The above application is hereby expressly incorporated by reference, in its entirety, into the present application.

BACKGROUND OF THE INVENTION

1. Field of the Invention

The present invention relates to a composition, a film, a lens, a solid-state imaging element, and compounds.

2. Description of the Related Art

Conventionally, various characteristics such as low colorability, high transparency, and high refractive index have been required for compounds used in optical materials (for example, materials forming microlens mounted on image sensors, a refractive index adjuster for color filters, and the like).

For example, JP2014-098101A discloses a triazine ring-containing polymer as a material having high heat resistance, high transparency, high refractive index, high solubility, and low volume shrinkage.

SUMMARY OF THE INVENTION

The solubility of the triazine ring-containing polymer disclosed in JP2014-098101A in a solvent is not necessarily high, and the handleability of the polymer is an issue.

Meanwhile, with the conventional techniques, it is impossible to provide a composition, which is capable of forming a film having a high refractive index and excellent exterior characteristics, by using a material other than the triazine ring-containing polymer.

An object of the present invention is to provide a composition capable of forming a film having a high refractive index and excellent exterior characteristics.

Another object of the present invention is to provide a film, a lens, and a solid-state imaging element in which the composition is used.

Still another object of the present invention is to provide novel compounds.

In order to achieve the above objects, the inventors of the present invention conducted intensive examinations. As a result, the inventors have found that the objects can be achieved using the following composition and have accomplished the present invention.

That is, the inventors have found that the objects can be achieved by the following constitution.

[1] A composition containing a compound represented by General Formula (I) which will be described later, a solvent, and a resin, in which a solubility of the compound represented by General Formula (I) in the solvent is less than 0.5% by mass at 25° C., and a maximum absorption wavelength of the compound represented by General Formula (I) at a wavelength range of 300 to 800 nm is equal to or shorter than 450 nm.

[2] The composition described in [1], in which B is $-NR^a-$, $-CONR^b-$, or $-SO_2NR^c-$.

[3] The composition described in [2], in which B is $-NH-$.

[4] The composition described in any one of [1] to [3], in which A is a heterocyclic group.

[5] The composition described in [4], in which A is a triazine ring group, a pyridine ring group, a pyrimidine ring group, or a group formed by the fusion of a partial structure represented by General Formula (IIA), which will be described later, with a benzene ring or a naphthalene ring.

[6] The composition described in [5], in which A is a triazine ring group.

[7] The composition described in any one of [1] to [6], in which C is an aryl group or a heterocyclic group.

[8] The composition described in any one of [1] to [7], in which the solvent is at least one kind of solvent selected from the group consisting of esters, alcohols, aromatic hydrocarbons, aliphatic hydrocarbons, nitriles, ketones, and halogen compounds.

[9] The composition described in any one of [1] to [8], further containing a polymerizable compound.

[10] The composition described in any one of [1] to [9], further containing a photopolymerization initiator.

[11] The composition described in [10], in which the photopolymerization initiator is an oxime compound.

[12] The composition described in any one of [1] to [11], in which the resin has a carbon-carbon double bond group in a molecule.

[13] A film formed of the composition described in any one of [1] to [12].

[14] A lens formed of the film described in [13].

[15] A solid-state imaging element comprising the lens described in [14].

[16] A compound represented by General Formula (III) which will be described later.

[17] The compound described in [16], in which the compound represented by General Formula (III) is a compound represented by General Formula (IV) which will be described later.

[18] The compound described in [16] or [17], in which X represents a nitrogen atom, and Y represents $-S-$.

[19] The compound described in [17] or [18], in which $Z^1$, $Z^2$, and $Z^3$ each represent a benzene ring.

[20] A compound represented by General Formula (V) which will be described later.

According to the present invention, it is possible to provide a composition capable of forming a film having a high refractive index and excellent exterior characteristics.

Furthermore, according to the present invention, it is possible to provide a film, a lens, and a solid-state imaging element in which the composition is used.

In addition, according to the present invention, it is possible to provide novel compounds.

DESCRIPTION OF THE PREFERRED EMBODIMENTS

Hereinafter, the present invention will be specifically described.

In the present specification, a range of numerical values described using "to" means a range including the numerical values listed before and after "to" as a lower limit and an upper limit.

In the present specification, "actinic rays" or "radiation", means, for example, a bright line spectrum of a mercury lamp, far ultraviolet rays represented by an excimer laser, extreme ultraviolet rays (EUV rays), X-rays, electron beams, and the like. Furthermore, in the present invention, light means actinic rays or radiation. In the present specification, unless otherwise specified, "exposure" includes not only the exposure by a mercury lamp, far ultraviolet rays represented by an excimer laser, X-rays, EUV rays, and the like, but also lithography by particle beams such as electron beams and ion beams.

In the present specification, "(meth)acrylate" represents acrylate and methacrylate, "(meth)acryl" represents acryl and methacryl, and "(meth)acryloyl" represents acryloyl and methacryloyl.

In the present specification, a term of "step" includes not only an independent step, but also a step which is not clearly differentiated from another step as long as the step acts as intended.

In the present specification, a weight-average molecular weight and a number-average molecular weight are each defined as a value which is measured by gel permeation chromatography (GPC) and expressed in terms of polystyrene. In the present specification, a weight-average molecular weight (Mw) and a number-average molecular weight (Mn) can be determined, for example, by using HLC-8220 (manufactured by Tosoh Corporation) as a measurement device, TSKgel Super AWM-H (manufactured by Tosoh Corporation, 6.0 mmID (inner diameter)×15.0 cm) as a column, and a 10 mmol/L lithium bromide N-methyl pyrrolidinone (NMP) solution as an eluent.

In the present specification, a polymerizable compound refers to a compound having a polymerizable group and may be a monomer or a polymer. The polymerizable group refers to a group involved in a polymerization reaction.

In the present specification, total solid contents refer to the total mass of components of a composition except for solvents.

In the present specification, in a case where there is no description regarding whether a group (atomic group) is substituted or unsubstituted, the group includes both a group which does not have a substituent and a group which has a substituent. For example, "alkyl group" includes not only an alkyl group which does not have a substituent (unsubstituted alkyl group) but also an alkyl group which has a substituent (substituted alkyl group). Examples of the substituent include groups selected from the following group of substituents T.

(Substituents T)

Examples of the substituents T include a halogen atom, an alkyl group, a cycloalkyl group, an alkenyl group, a cycloalkenyl group, an alkynyl group, an aryl group, a heterocyclic group, a cyano group, a hydroxyl group, a nitro group, a carboxyl group, an alkoxy group, an aryloxy group, a silyloxy group, a heterocyclic oxy group, an acyloxy group, a carbamoyloxy group, an amino group (including an alkylamino group and an anilino group), an acylamino group, an aminocarbonylamino group, an alkoxycarbonylamino group, an aryloxycarbonylamino group, a sulfamoylamino group, an alkylsulfonylamino or arylsulfonylamino group, a mercapto group, an alkylthio group, an arylthio group, a heterocyclic thio group, a sulfamoyl group, a sulfo group, an alkylsulfinyl or arylsulfinyl group, an alkylsulfonyl or arylsulfonyl group, an acyl group, an aryloxycarbonyl group, an alkoxycarbonyl group, a carbamoyl group, an arylazo or heterocyclic azo group, an imide group, a phosphino group, a phosphinyl group, a phosphinyloxy group, a phosphinylamino group, a silyl group, and the like. Details of these will be described below.

Examples of the substituents T include a halogen atom (for example, a fluorine atom, a chlorine atom, a bromine atom, and an iodine atom), a linear or branched alkyl group (a linear or branched substituted or unsubstituted alkyl group which is preferably an alkyl group having 1 to 30 carbon atoms, for example, a methyl group, an ethyl group, a n-propyl group, an isopropyl group, a tert-butyl group, a n-octyl group, a 2-chloroethyl group, a 2-cyanoethyl group, and a 2-ethylhexyl group), a cycloalkyl group (preferably a substituted or unsubstituted cyclolakyl group having 3 to 30 carbon atoms, for example, a cyclohexyl group and a cyclopentyl group, the cycloalkyl group may be a polycycloalkyl group (for example, a group having a polycyclic structure such as a bicycloalkyl group (preferably a substituted or unsubstituted bicycloalkyl group having 5 to 30 carbon atoms, more specifically, a bicyclo[1,2,2]heptan-2-yl group, a bicyclo[2,2,2]octan-3-yl group, and the like), a tricycloalkyl group, and the like), among these, a monocyclic cycloalkyl group or a bicycloalkyl group is preferable, and a monocyclic cycloalkyl group is more preferable), a linear or branched alkenyl group (a linear or branched substituted or unsubstituted alkenyl group, preferably an alkenyl group having 2 to 30 carbon atoms, for example, a vinyl group, an allyl group, a prenyl group, a geranyl group, and an oleyl group), a cycloalkenyl group (preferably a substituted or unsubstituted cycloalkenyl group having 3 to 30 carbon atoms, for example, a 2-cyclopenten-1-yl group and a 2-cyclohexen-1-yl group, the cycloalkenyl group may be a polycycloalkenyl group (a group having a polycyclic structure such as a bicycloalkenyl group (preferably a substituted or unsubstituted bicycloalkenyl group having 5 to 30 carbon atoms, more specifically a bicyclo[2,2,1]-hept-2-en-1-yl group, a bicyclo[2,2,2]-oct-2-en-4-yl group, and the like) a tricycloalkenyl group, and the like), among these, a monocyclic cycloalkenyl group is preferable), an alkynyl group (preferably a substituted or unsubstituted alkynyl group having 2 to 30 carbon atoms, for example, an ethynyl group, a propargyl group, a trimethylsilylethynyl group, and the like), an aryl group (preferably a substituted or unsubstituted aryl group having 6 to 30 carbon atoms, for example, a phenyl group, a p-tolyl group, a naphthyl group, a m-chlorophenyl group, an o-hexadecanoylaminophenyl group, a pyrenyl group, a biphenyl group, and a terphenyl group), a heterocyclic group (preferably a substituted or unsubstituted heterocyclic group having 5 to 7 carbon atoms; the heterocyclic group is a saturated or unsaturated and aromatic or non-aromatic; the heterocyclic group is a monocyclic or a fused ring; ring-constituting atoms in the heterocyclic group are selected from a carbon atom, a nitrogen atom, and a sulfur atom; the heterocyclic group is more preferably a heterocyclic group having at least one heteroatom among a nitrogen atom, an oxygen atom, or a sulfur atom and even more preferably a 5-membered or 6-membered aromatic heterocyclic group having 3 to 30 carbon atoms; for example, a 2-furyl group, a 2-thienyl group, a 2-pyridyl group, a 4-pyridyl group, a 2-pyrimidinyl group, and a 2-benzothiazolyl group), a cyano group, a hydroxyl group, a nitro group, and a carboxyl group, an alkoxy group (preferably a substituted or unsubstituted alkoxy group having 1 to 30 carbon atoms, for example, a methoxy group, an ethoxy group, a isopropoxy group, a tert-butoxy group, a n-octyloxy group, and a 2-methoxyethoxy group), an aryloxy group (preferably a substituted or unsubstituted aryloxy group having 6 to 30 carbon atoms, for example, a phenoxy group, a 2-methylphenoxy group, a 2,4-di-tert-amylphenoxy group, a 4-tert-butylphenoxy group, a 3-nitrophenoxy group, and a 2-tetradecanoylaminophenoxy group), a silyloxy group (preferably a silyloxy group having 3 to 20 carbon atoms, for example, a trimethylsilyloxy group and a tert-butyldimethylsilyloxy group), a heterocyclic oxy group (preferably a substituted or unsubstituted heterocyclic oxy group having 2 to 30 carbon atoms; as a heterocyclic portion, the heterocyclic portion described above regarding the heterocyclic group is preferable, for example, a 1-phenyltetrazol-5-oxy group and a 2-tetrahydropyranyloxy group), an acyloxy group (preferably a formyloxy group, a substituted or unsubstituted alkylcarbonyloxy group having 2 to 30 carbon atoms, or a substituted or unsubstituted arylcarbonyloxy group having 6 to 30 carbon atoms, for example, a formyloxy group, an acetyloxy group, a pivaloyloxy group, a stearoyloxy group, a benzoyloxy group, a p-methoxyphenylcarbonyloxy group, an acryloyloxy group, and a methacryloyloxy group), a carbamoyloxy group (preferably a substituted or unsubstituted carbamoyloxy group having 1 to 30 carbon atoms, for example, a N,N-dimethylcarbamoyloxy group, a N,N-diethylcarbamoyloxy group, a morpholinocarbonyloxy group, a N,N-di-n-octylaminocarbonyloxy group, and N-n-octylcarbamoyloxy group), an alkoxycarbonyloxy group (preferably a substituted or unsubstituted alkoxycarbonyloxy group having 2 to 30 carbon atoms, for example, a methoxycarbonyloxy group, an ethoxycarbonyloxy group, a tert-butoxycarbonyloxy group, and a n-octylcarbonyloxy group), an aryloxycarbonyloxy group (preferably a substituted or unsubstituted aryloxycarbonyloxy group having 7 to 30 carbon atoms, for example, a phenoxycarbonyloxy group, a p-methoxyphenoxycarbonyloxy group, and a p-n-hexadecyloxyphenoxycarbonyloxy group), an amino group (preferably an amino group, a substituted or unsubstituted alkylamino group having 1 to 30 carbon atoms, a substituted or unsubstituted arylamino group having 6 to 30 carbon atoms, or a heterocyclic amino group having 0 to 30 carbon atoms, for example, an amino group, a methylamino group, a dimethylamino group, an anilino group, a N-methyl-anilino group, a diphenylamino group, and a N-1,3,5-triazin-2-ylamino group), an acylamino group (preferably a formylamino group, a substituted or unsubstituted alkylcarbonylamino group having 1 to 30 carbon atoms, or a substituted or unsubstituted arylcarbonylamino group having 6 to 30 carbon atoms, for example, a formylamino group, an acetylamino group, a pivaloylamino group, a lauroylamino group, a benzoylamino group, a 3,4,5-tri-n-octyloxyphenylcarbonylamino group, an acryloylamino group, and a methacryloylamino group), an aminocarbonylamino group (preferably a substituted or unsubstituted aminocarbonylamino group having 1 to 30 carbon atoms, for example, a carbamoylamino group, a N,N-dimethylaminocarbonylamino group, N,N-diethylaminocarbonylamino group, and a morpholinocarbonylamino group), an alkoxycarbonylamino group (preferably a substituted or unsubstituted alkoxycarbonylamino group having 2 to 30 carbon atoms, for example, a methoxycarbonylamino group, an ethoxycarbonylamino group, a tert-butoxycarbonylamino group, a n-octadecyloxycarbonylamino group, and a N-methyl-methoxycarbonylamino group), an aryloxycarbonylamino group (preferably a substituted or unsubstituted aryloxycarbonylamino group having 7 to 30 carbon atoms, for example, a phenoxycarbonylamino group, a p-chlorophenoxycarbonylamino group, and a m-n-octyloxyphenoxycarbonylamino group), a sulfamoylamino group (preferably a substituted or unsubstituted sulfamoylamino group having 0 to 30 carbon atoms, for example, a sulfamoylamino group, a N,N-dimethylaminosulfonylamino group, and N-n-octylaminosulfonylamino group), an alkylsulfonylamino or arylsulfonylamino group (preferably a substituted or unsubstituted alkylsulfonylamino group having 1 to 30 carbon atoms or a substituted or unsubstituted arylsulfonylamino group having 6 to 30 carbon atoms, for example, a methylsulfonylamino group, a butylsulfonylamino group, a phenylsulfonylamino group, a 2,3,5-trichlorophenylsulfonylamino group, and a p-methylphenylsulfonylamino group), a mercapto group, an alkylthio group (preferably a substituted or unsubstituted alkylthio group having 1 to 30 carbon atoms, for example, a methylthio group, an ethylthio group, and a n-hexadecylthio group), an arylthio group (preferably a substituted or unsubstituted arylthio group having 6 to 30 carbon atoms, for example, a phenylthio group, a p-chlorophenylthio group, and a m-methoxyphenylthio group), a heterocyclic thio group (preferably a substituted or unsubstituted heterocyclic thio group having 2 to 30 carbon atoms; as a heterocyclic portion, the heterocyclic portion described above regarding the heterocyclic group is preferable, for example, a 2-benzothiazolylthio group and a 1-phenyltetrazol-5-ylthio group), a sulfamoyl group (preferably a substituted or unsubstituted sulfamoyl group having 0 to 30 carbon atoms, for example, a N-ethylsulfamoyl group, a N-(3-dodecyloxypropyl)sulfamoyl group, N,N-dimethylsulfamoyl group, N-acetylsulfamoyl group, a N-benzoylsulfamoyl group, and a N-(N'-phenylcarbamoyl)sulfamoyl group, a sulfo group, an alkylsulfinyl or arylsulfinyl group (preferably a substituted or unsubstituted alkylsulfinyl group having 1 to 30 carbon atoms or a substituted or unsubstituted arylsulfinyl group having 6 to 30 carbon atoms, for example, a methylsulfinyl group, an ethylsulfinyl group, a phenylsulfinyl group, and a p-methylphenylsulfinyl group), an alkylsulfonyl or arylsulfonyl group (preferably a substituted or unsubstituted alkylsulfonyl group having 1 to 30 carbon atoms or a substituted or unsubstituted arylsulfonyl group having 6 to 30 carbon atoms, for example, a methylsulfonyl group, an ethylsulfonyl group, a phenylsulfonyl group, and a p-methylphenylsulfonyl group), an acyl group (preferably a formyl group, a substituted or unsubstituted alkylcarbonyl group having 2 to 30 carbon atoms, or a substituted or unsubstituted arylcarbonyl group having 7 to 30 carbon atoms, for example, an acetyl group, a pivaloyl group, a 2-chloroacetyl group, a stearoyl group, a benzoyl group, a p-n-octyloxyphenylcarbonyl group, an acryloyl group, and a methacryloyl group), an aryloxycarbonyl group (preferably a substituted or unsubstituted aryloxycarbonyl group having 7 to 30 carbon atoms, for example, a phenoxycarbonyl group, a o-chlorophenoxycarbonyl group, a m-nitrophenoxycarbonyl group, and a p-tert-butylphenoxycarbonyl group), an alkoxycarbonyl group (preferably a substituted or unsubstituted alkoxycarbonyl group having 2 to 30 carbon atoms, for example, a methoxycarbonyl group, an ethoxycarbonyl group, a tert-butoxycarbonyl group, and a n-octadecyloxycarbonyl group), a carbamoyl group (preferably a substituted or unsubstituted carbamoyl group having 1 to 30 carbon atoms, for example, a carbamoyl group, a N-methylcarbamoyl group, a N,N-dimethylcarbamoyl group, a N,N-di-n-octylcarbamoyl group, and a N-(methylsulfonyl)carbamoyl group), an arylazo or heterocyclic azo group (preferably a substituted or unsubstituted arylazo group having 6 to 30 carbon atoms or a substituted or unsubstituted heterocyclic azo group having 3 to 30 carbon atoms (as a heterocyclic portion of the heterocyclic azo group, the heterocyclic portion described above regarding the heterocyclic group is preferable), for example, a phenylazo group, a p-chlorophenylazo group, and a 5-ethylthio-1,3,4-thiadiazol-2-ylazo group), an imide group (preferably a substituted or unsubstituted imide group having 2 to 30 carbon atoms, for example, a N-succinimide group and a N-phthalimide group), a phosphino group (preferably a substituted or unsubstituted phosphino group having 2 to 30 carbon atoms, for example, a dimethylphosphino group, a diphenylphosphino group, and a methylphenoxyphosphino group), a phosphinyl group (preferably a substituted or unsubstituted phosphinyl group having 2 to 30 carbon atoms, for example, a phosphinyl group, a dioctyloxyphosphinyl group, and a diethoxyphosphinyl group), a phosphinyloxy group (preferably a substituted or unsubstituted phosphinyloxy group having 2 to 30 carbon atoms, for example, a diphenoxyphosphinyloxy group and a dioctyloxyphosphinyloxy group), a phosphinylamino group (preferably a substituted or unsubstituted phosphinylamino group having 2 to 30 carbon atoms, for example, dimethoxyphosphinylamino group and a dimethylaminophosphinylamino group), and a silyl group (preferably a substituted or unsubstituted silyl group having 3 to 30 carbon atoms, for example, a trimethylsilyl group, a tert-butyldimethylsilyl group, and a phenyldimethylsilyl group).

Among the above functional groups, in functional groups having hydrogen atoms, the portion of the hydrogen atoms may be substituted with any of the above groups. Examples of functional groups that can be introduced as substituents include an alkylcarbonylaminosulfonyl group, an arylcarbonylaminosulfonyl group, an alkylsulfonylaminocarbonyl group, and an arylsulfonylaminocarbonyl group. More specifically, examples thereof include a methylsulfonylaminocarbonyl group, a p-methylphenylsulfonylaminocarbonyl group, an acetylaminosulfonyl group, and a benzoylaminosulfonyl group.

[Composition]

The composition according to an embodiment of the present invention contains a compound represented by General Formula (I) which will be described later, a solvent, and a resin, in which a solubility of the compound represented by General Formula (I) in the solvent is less than 0.5% by mass at 25° C., and a maximum absorption wavelength of the compound represented by General Formula (I) in a wavelength range of 300 to 800 nm is equal to or shorter than 450 nm.

One of the characteristics of the composition is that the compound represented by General Formula (I) (hereinafter, referred to as "specific compound" as well) as a material of high refractive index is dispersed in the solvent.

First, according to the examination conducted by the inventors of the present invention, it has been found that in a case where an attempt is made to further increase the refractive index of the material having high refractive index represented by a triazine-based compound, due to the influence such as an increase in intermolecular force, the solubility of the material in a solvent is reduced. That is, in a material of high refractive index, the refractive index and the solubility tend to have a trade-off relationship.

In contrast, the present invention has overcame the above problem by combining the specific compound, a solvent in which the specific compound exhibits low solubility, and a dispersant. More specifically, generally, the specific compound designed for improving refractive index does not dissolve in a solvent in which the specific compound exhibits low solubility. However, in a case where the specific compound is used in combination with a resin, the resin functions as a dispersant of the specific compound. That is, presumably, in the composition, the specific compound may be dispersed in the form of particles just as a pigment. As a result, a film is obtained which exhibits a high refractive index resulting from the specific compound and excellent exterior characteristics resulting from the excellent dispersibility of the specific compound.

In the conventional techniques, in order to dissolve a material having low solubility, a polar solvent needs to be used. However, the safety of the polar solvent is of concern, the polar solvent easily remains in a film, and it is apprehended that the polar solvent may deteriorate moisture resistance and weather fastness of a film.

In contrast, in the present invention, it is not necessary to use a polar solvent as a solvent. Therefore, the occurrence of problems described above can be inhibited.

As will be described later, in the compound represented by General Formula (I), in a case where the group represented by A is a triazine ring group, and the group represented by B is —NH—, the obtained film has a higher refractive index and excellent exterior characteristics.

In a case where the composition further contains a polymerizable compound and a photopolymerization initiator, the composition expresses photolithography properties. Particularly, in a case where the resin contained in the composition has an acid group, the composition can form a pattern having excellent developability and excellent shape (having a rectangular cross section).

Furthermore, it is preferable that the composition substantially does not contain a polar solvent. In a case where the composition substantially does not contain a polar solvent, residues are hardly generated at the time of development, and the cross-sectional shape of the obtained pattern is excellent (the pattern has a rectangular cross-sectional shape).

Hereinafter, components contained in the composition will be described.

<Compound Represented by General Formula (I)>

Hereinafter, the compound represented by General Formula (I) will be described.

$$A\text{-}(\text{-}B\text{-}C)_n \qquad (I)$$

In General Formula (I), n represents an integer equal to or greater than 2. A represents a benzene ring group, a naphthalene ring group, or a heterocyclic group. B represents a single bond, —O—, —NR$^a$—, —S—, —CONR$^b$—, or —SO$_2$NR$^c$—. R$^a$, R$^b$, and R$^c$ each independently represent a hydrogen atom, an alkyl group, or an aryl group. C represents an alkyl group, an aryl group, or a heterocyclic group. A plurality of B's may be the same as or different from each other. Furthermore, a plurality of C's may be the same as or different from each other.

In General Formula (I), A represents a benzene ring group, a naphthalene ring group, or a heterocyclic group.

The benzene ring group represented by A is a group formed by the removal of n hydrogen atoms from a benzene ring. The naphthalene ring group represented by A is a group formed by the removal of n hydrogen atoms from a naphthalene ring.

The heterocyclic group represented by A is not particularly limited, and examples thereof include an aliphatic heterocyclic group and an aromatic heterocyclic group. Examples of the aliphatic heterocyclic ring include a 5-membered, 6-membered-, or 7-membered aliphatic heterocyclic ring and a fused ring of these. Examples of the aromatic heterocyclic ring include a 5-membered, 6-membered, or 7-membered aromatic heterocyclic ring and a fused ring of these.

The fused ring may include a ring such as a benzene ring other than a heterocyclic group.

Examples of heteroatoms contained in the aliphatic heterocyclic group include a nitrogen atom, an oxygen atom, and a sulfur atom. The number of carbon atoms in the aliphatic heterocyclic ring is not particularly limited, but is preferably 3 to 20.

Specific examples of the aliphatic heterocyclic ring are not particularly limited and include an oxolane ring, an oxane ring, a piperidine ring, a piperazine ring, and the like. The aliphatic heterocyclic ring constitutes the aliphatic heterocyclic group by the removal of n hydrogen atoms from the ring.

Examples of heteroatoms contained in the aromatic heterocyclic group include a nitrogen atom, an oxygen atom, and a sulfur atom. The number of carbon atoms in the aromatic heterocyclic group is not particularly limited, but is preferably 3 to 20.

Specific examples of the aromatic heterocyclic ring are not particularly limited and include a furan ring, a thiophene ring, a pyrrole ring, an oxazole ring, an isoxazole ring, an oxadiazole ring, a thiazole ring, an isothiazole ring, a thiadiazole ring, an imidazole ring, a pyrazole ring, a triazole ring, a furazan ring, a tetrazole ring, a pyridine ring, a pyridazine ring, a pyrimidine ring, a pyrazine ring, a triazine ring, a tetrazine ring, a benzofuran ring, an isobenzofuran ring, a benzothiophene ring, an indole ring, an indoline ring, an isoindole ring, a benzoxazole ring, a benzothiazole ring, an indazole ring, a benzimidazole ring, a quinoline ring, an isoquinoline ring, an cinnoline ring, a phthalazine ring, a quinazoline ring, a quinoxaline ring, a dibenzofuran ring, a dibenzothiophene ring, a carbazole ring, an acridine ring, a phenanthridine ring, a phenanthroline ring, a phenazine ring, a naphthyridine ring, a purine ring, a pteridine ring, and the like. The aromatic heterocyclic ring constitutes the aromatic heterocyclic group by the removal of n hydrogen atoms from the ring.

In view of further increasing the refractive index of the film to be formed, in view of further improving the moisture resistance of the film to be formed, and/or in view of further improving the exterior characteristics of the film to be formed, as the aromatic heterocyclic ring, a triazine ring, a pyridine ring, a pyrimidine ring, a pyrazine ring, a thiophene ring, a thiazole ring, an imidazole ring, and a ring formed by the fusion of a partial structure represented by General Formula (II) with a benzene ring or a naphthalene ring are preferable.

In General Formula (II), X represents a nitrogen atom or $CR^d$. Y represents $-NR^e-$, $-S-$, or $-O-$. $R^d$ and $R^e$ each independently represent a hydrogen atom, an alkyl group, or an aryl group. * represents a position where General Formula (II) is bonded to a benzene ring or a naphthalene ring. That is, General Formula (II) forms a ring (preferably a 5-membered or 6-membered ring and more preferably a 5-membered ring) together with 2 different carbon atoms on a benzene ring or a naphthalene ring.

In General Formula (II), the alkyl group represented by $R^d$ and $R^e$ (the alkyl group may be linear, branched, or cyclic) is not particularly limited, and examples thereof include an alkyl group having 1 to 10 carbon atoms. As the alkyl group, an alkyl group having 1 to 6 carbon atoms is preferable, and an alkyl group having 1 to 3 carbon atoms is more preferable. The aryl group represented by $R^d$ and W is not particularly limited, and examples thereof include a phenyl group and the like.

As $R^d$ and $R^e$, among the above, a hydrogen atom or an alkyl group having 1 to 3 carbon atoms is preferable, and a hydrogen atom is more preferable.

The alkyl group and the aryl group represented by $R^d$ and $R^e$ may have a substituent (for example, a group exemplified in the group of substituents T).

In a case where A represents a ring formed by the fusion of the partial structure represented by General Formula (II) with a benzene ring or a naphthalene ring, examples of A include the following rings. X and Y in the following rings have the same definition as X and Y in General Formula (II) respectively.

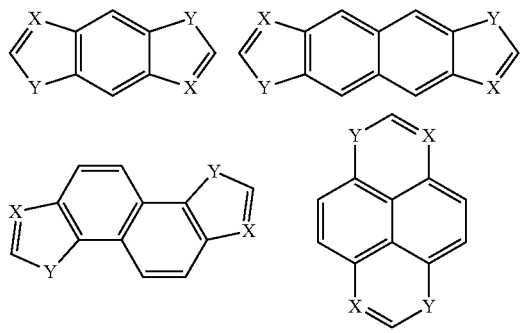

In view of further increasing the refractive index of the film to be formed, in view of further improving the moisture resistance of the film to be formed, and/or in view of further improving the exterior characteristics of the film to be formed, as A, among the above, a heterocyclic group is preferable, a triazine ring group, a pyridine ring group, a pyrimidine ring group, or a group formed by the fusion of the partial structure represented by General Formula (IIA) with a benzene ring or a naphthalene ring is more preferable, and a triazine ring group is even more preferable.

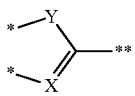
(IIA)

In General Formula (IIA), X and Y have the same definition as X and Y in General Formula (II) respectively, and preferred aspects thereof are also the same. * represents a position where General Formula (IIA) is bonded to a benzene ring or a naphthalene ring. ** represents a position where General Formula (IIA) is bonded to B.

A may further have a substituent (for example, a group exemplified in the group of substituents T).

In General Formula (I), B represents a single bond, —O—, —NR$^a$—, —S—, —CONR$^b$—, or —SO$_2$NR$^c$—.

R$^a$, R$^b$, and R$^c$ each independently represent a hydrogen atom, an alkyl group, or an aryl group. The alkyl group and the aryl group represented by R$^a$, R$^b$, and R$^c$ have the same definition as R$^d$ and R$^e$ in General Formula (II), and preferred aspects thereof are also the same.

A plurality of B's may be the same as or different from each other.

In view of further increasing the refractive index of the film to be formed, in view of further improving the moisture resistance of the film to be formed, and/or in view of further improving the exterior characteristics of the film to be formed, as B, —NR$^a$—, —CONR$^b$—, or —SO$_2$NR$^c$— is preferable, —NR$^a$— is more preferable, and —NH— is even more preferable.

C represents an alkyl group, an aryl group, or a heterocyclic group.

The alkyl group represented by C (the alkyl group may be linear, branched, or cyclic) is not particularly limited. As the alkyl group, an alkyl group having 1 to 10 carbon atoms preferable, an alkyl group having 1 to 6 carbon atoms is more preferable, and an alkyl group having 1 to 3 carbon atoms is even more preferable.

The aryl group represented by C is not particularly limited, and examples thereof include 6- to 10-membered rings or an aryl group formed of a fused ring of 6- to 10-membered rings.

Specific examples of rings constituting the aryl group are not particularly limited and include a benzene ring, a naphthalene ring, an anthracene ring, a phenanthrene ring, a triphenylene ring, a pyrene ring, and a naphthacene ring. Among these, benzene ring or naphthalene ring is preferable, and a benzene ring is more preferable. The aryl ring constitutes the aryl group by the removal of one hydrogen atom from the ring.

The heterocyclic group represented by C is not particularly limited, and examples thereof include an aliphatic heterocyclic group and an aromatic heterocyclic group.

The heterocyclic group represented by C has the same definition as the heterocyclic group represented by A.

In view of further increasing the refractive index of the film to be formed, in view of further improving the moisture resistance of the film to be formed, and/or in view of further improving the exterior characteristics of the film to be formed, as C, among the above, an aryl group or a heterocyclic group is preferable, and an aryl group or an aromatic heterocyclic group is more preferable.

A plurality of C's may be the same as or different from each other.

C may further have a substituent (for example, a group selected from the group of substituents T). In a case where C has a substituent, in view of further increasing refractive index, as the substituent, for example, —SR$^{11}$ (R$^{11}$ is preferably an alkyl group having 1 to 3 carbon atoms and more preferably a methyl group), a halogen atom (a fluorine atom, a chlorine atom, a bromine atom, or an iodine atom), a group having a conjugated double bond (for example, an aryl group and the like), a cyano group, a nitro group, an acetylamino group, or an alkyl group (preferably an alkyl group having 1 to 3 carbon atoms and more preferably a methyl group) is preferable.

n is not particularly limited as long as it is an integer equal to or greater than 2. The upper limit thereof is not particularly limited, but is preferably an integer equal to or smaller than 10. Particularly, in view of further improving dispersibility (such that the exterior characteristics are further improved), n is preferably 2 to 6, and more preferably 2 or 3.

The molecular weight of the specific compound is not particularly limited. For example, the molecular weight of the specific compound is preferably equal to or greater than 100, and more preferably equal to or greater than 200. Furthermore, the molecular weight of the specific compound is preferably equal to or smaller than 2,000, and more preferably equal to or smaller than 1,000.

The maximum absorption wavelength of the specific compound in a wavelength range of 300 to 800 nm is equal to or shorter than 450 nm, which in other words means that the aforementioned film substantially is not colored. From the viewpoint of further inhibiting coloring, the maximum absorption wavelength of the compound represented by General Formula (I) in a wavelength range of 300 to 800 nm is preferably equal to or shorter than 430 nm, more preferably equal to or shorter than 410 nm, even more preferably equal to or shorter than 400 nm, and particularly preferably equal to or shorter than 380 nm.

In a case where the specific compound substantially does not have absorption in a wavelength range of 300 to 800 nm (specifically, in a case where the form of the absorption wavelength of the specific compound in a wavelength range of 300 to 800 nm is substantially flat), the maximum absorption wavelength is regarded as being equal to or shorter than 450 nm.

For example, the maximum absorption wavelength of the specific compound in a wavelength range of 300 to 800 nm can be measured by the following method.

First, the specific compound, a solvent in which the specific compound has a solubility less than 0.5% by mass at 25° C., and a resin (as the resin, a resin of the same type as the resin used in the composition containing the specific compound is used; examples of the resin include dispersants which will be described later) are subjected to a dispersion treatment, thereby preparing a composition (hereinafter, referred to as "composition 1" as well). The composition is diluted 1,000× with a solvent. The maximum absorption wavelength of the obtained solution in a wavelength range of 300 to 800 nm is measured. Then, a composition (hereinafter, referred to as "composition 2" as well) containing components of the aforementioned composition except for the specific compound is prepared, and the maximum absorption wavelength of the composition in a wavelength range of 300 to 800 nm is measured.

Thereafter, from the absorption spectrum chart of the composition 1 obtained according to the procedure described above, the absorption spectrum chart of the composition 2 obtained according to the procedure described above is subtracted, thereby calculating the maximum absorption wavelength of the absorbance of the specific compound in a wavelength range of 300 to 800 nm.

For the measurement, Carry5000 (manufactured by Agilent Technologies, Inc.) and the like can be used.

Specific examples of the specific compound will be shown below, but the present invention is not limited thereto. In the following specific examples, "Ac" represents an acetyl group, and "Me" represents a methyl group.

A-1

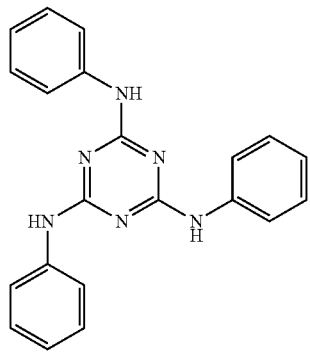

A-2

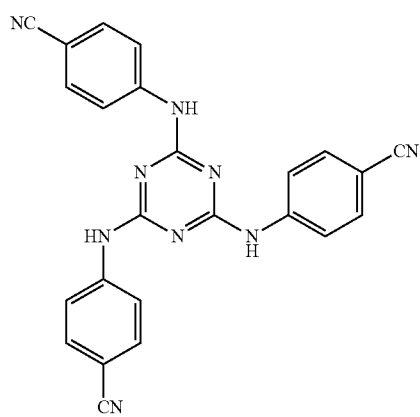

A-3

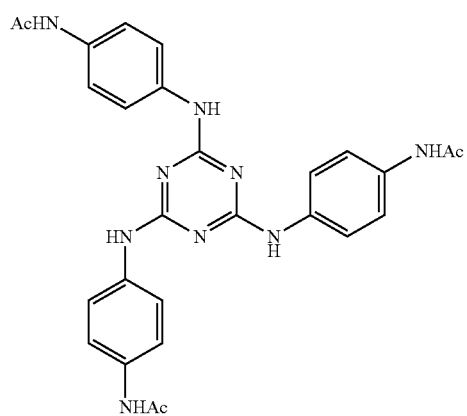

A-4

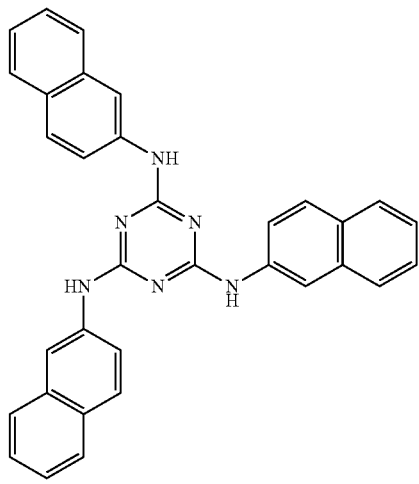

A-5

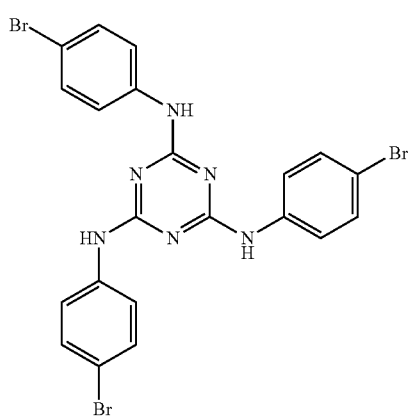

A-6

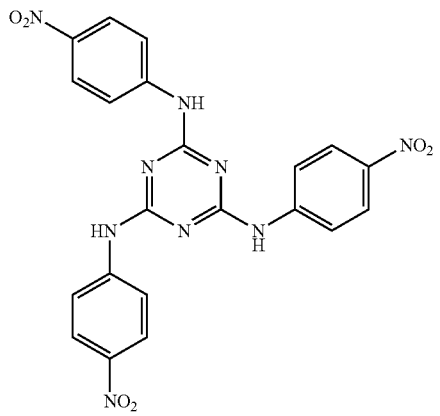

-continued
A-7
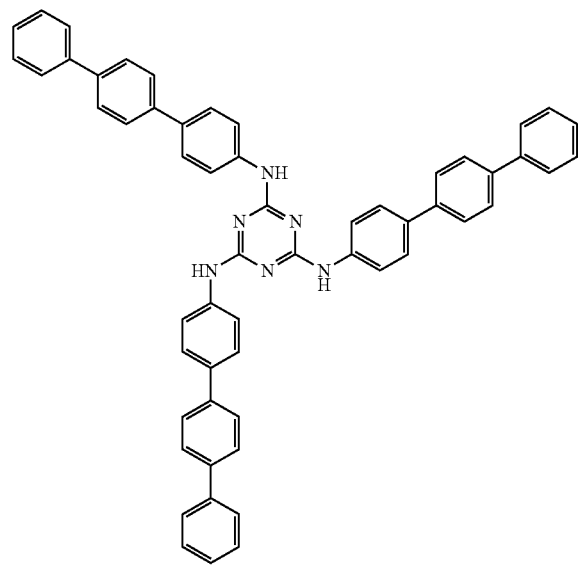
A-10
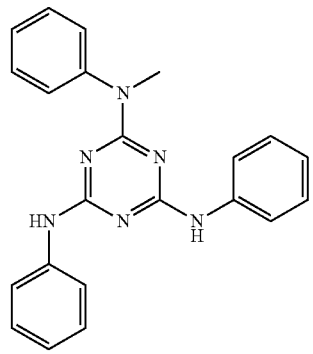
A-11
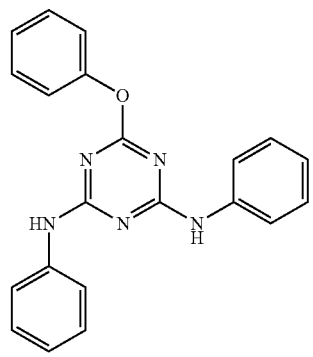
A-8
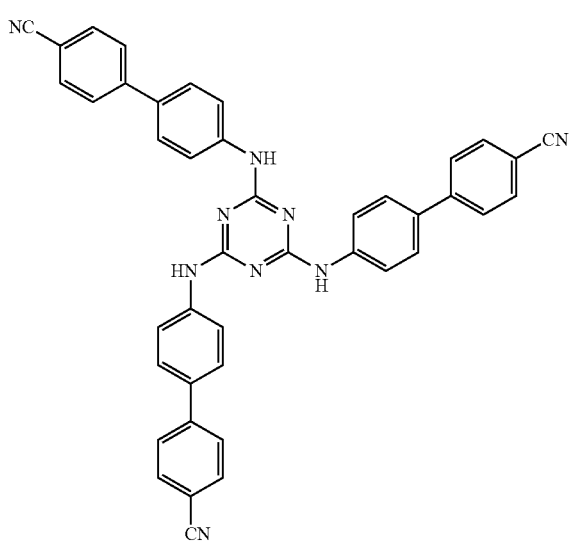
A-12
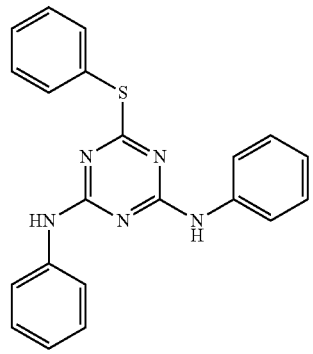
A-9
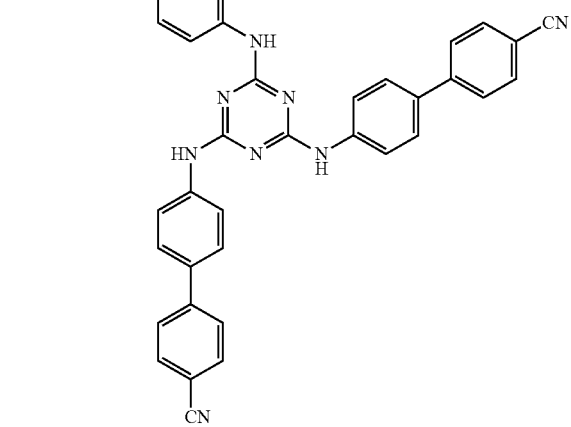
A-13
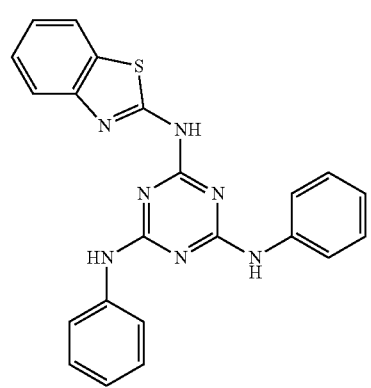

A-14
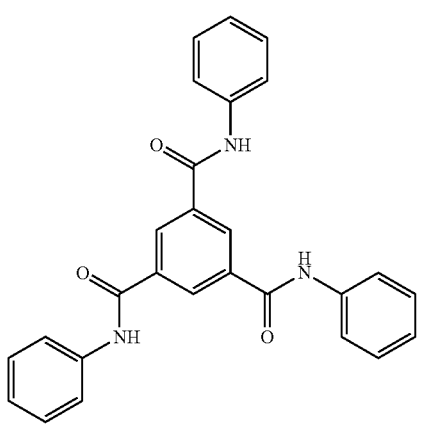
A-15
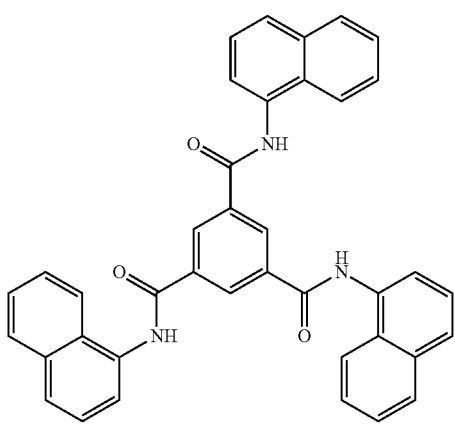
A-16
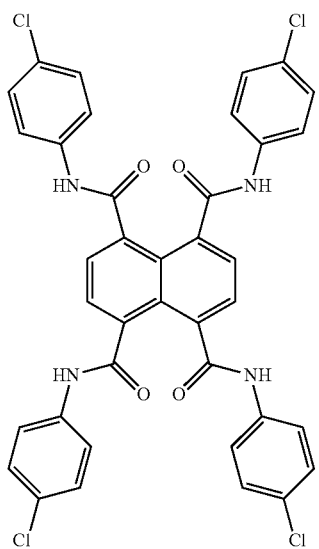
A-17
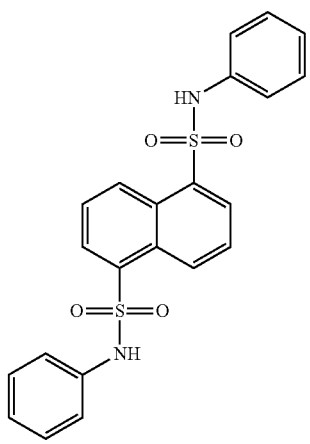
A-18
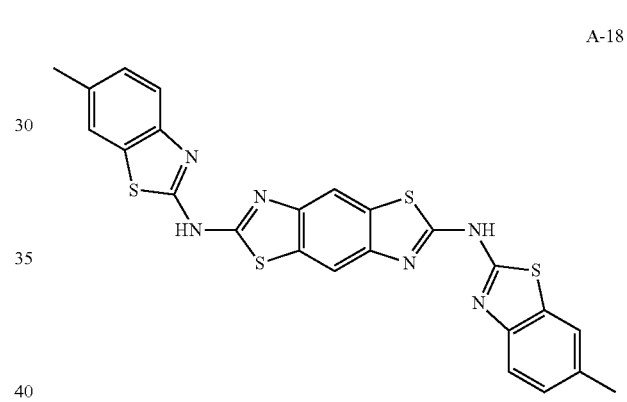
A-19
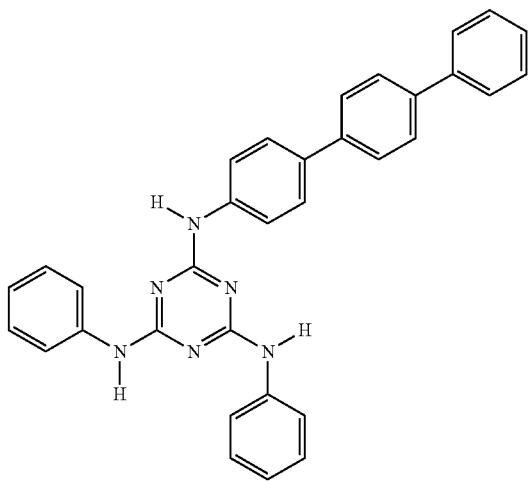

A-20
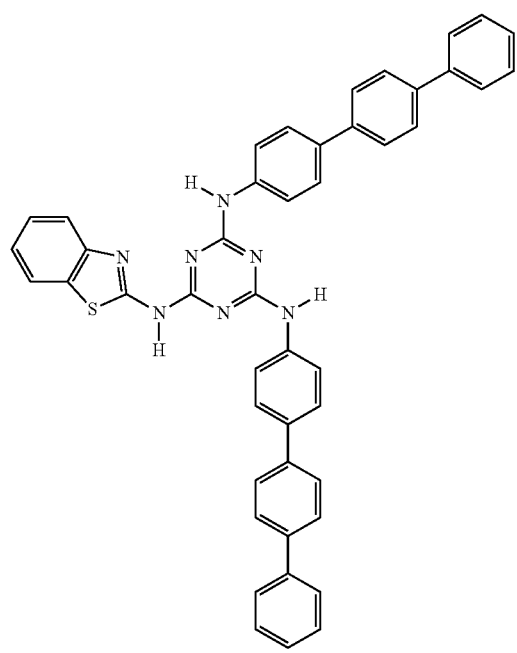
A-22
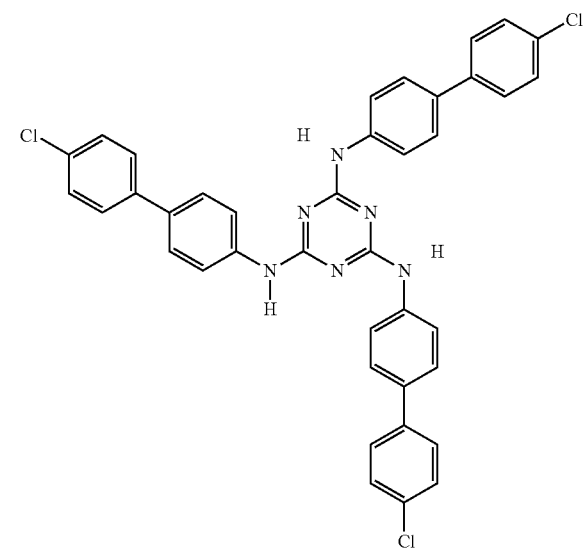
A-21
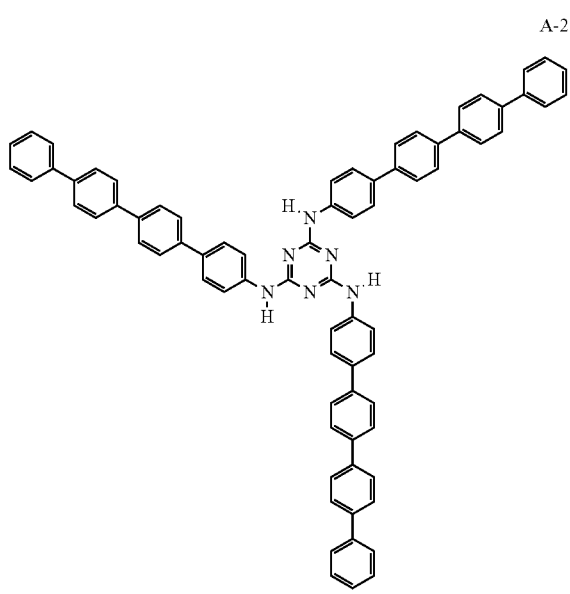
A-23
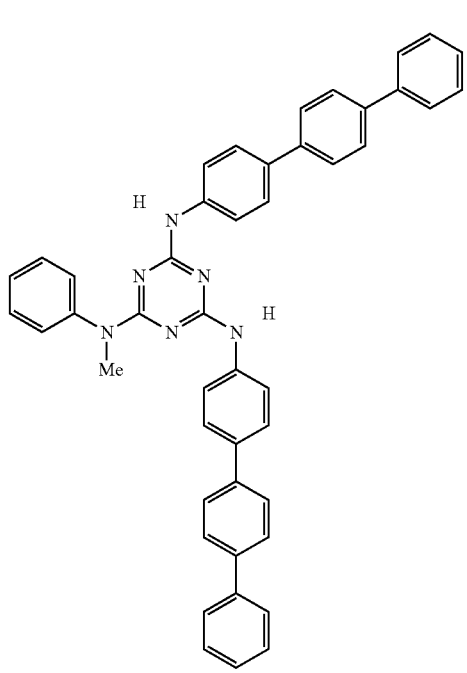

-continued

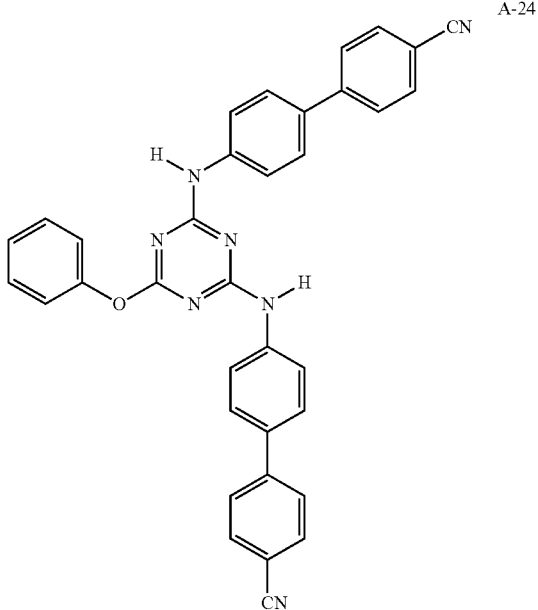

A-24

The specific compound can be synthesized by known methods. For example, the specific compound can be synthesized based on the description in JP2016-204493A and the like. As solvents for synthesis, it is preferable to use amides such as 3-methoxy-N,N-dimethylpropanamide and 3-butoxy-N,N-dimethylpropanamide.

The content of the specific compound in the composition is not particularly limited. Based on the total amount of the composition (including solvents), the content of the specific compound is preferably 1% to 30% by mass, more preferably 3% to 25% by mass, and even more preferably 5% to 20% by mass.

One kind of specific compound may be used singly, or two or more kinds of specific compounds may be used in combination. In a case where two or more kinds of specific compounds are used in combination, the total content thereof is preferably within the above range.

<Solvent>

The composition contains a solvent satisfying the following condition 1. In a case where the solvent (hereinafter, referred to as "specific solvent" as well) satisfying the following condition 1 is used in the composition, the specific compound as a material of high refractive index remains dispersed in the solvent.

Condition 1: a solvent in which the specific compound has a solubility less than 0.5% by mass at 25° C.

For example, the solubility of the specific compound in a solvent at 25° C. can be determined by the method described in Examples.

The type of the specific solvent is not particularly limited as long as the specific solvent satisfies the condition 1 described above.

Examples of the specific solvent include esters such as ethyl cellosolve acetate, ethyl carbitol acetate, butyl carbitol acetate, ethylene glycol monomethyl ether acetate, ethylene glycol monoethyl ether acetate, ethylene glycol monobutyl ether acetate, propylene glycol monomethyl ether acetate (PGMEA), propylene glycol monoethyl ether acetate, 3-methoxypropyl acetate, 3-methoxybutyl acetate, methyl 3-methoxypropionate, methyl 3-ethoxypropionate, ethyl 3-ethoxypropionate, propylene glycol diacetate, diethylene glycol monobutyl ether acetate, γ-butyrolactone, ethyl acetate, butyl acetate, methyl lactate, ethyl lactate, and cyclohexyl acetate; alcohols such as ethylene glycol monomethyl ether, ethylene glycol monoethyl ether, ethylene glycol dimethyl ether, propylene glycol monomethyl ether (PGME), propylene glycol monoethyl ether, ethylene glycol monoisopropyl ether, 3-methoxypropanol, methoxymethoxyethanol, dipropylene glycol dimethyl ether, diethylene glycol monomethyl ether, diethylene glycol monoethyl ether, diethylene glycol dimethyl ether, and diethylene glycol diethyl ether; aromatic hydrocarbons such as benzene, toluene, xylene, ethyl benzene, and anisole; aliphatic hydrocarbons such as cyclohexane; nitriles such as acetonitrile; ketones such as acetone, methyl ethyl ketone, acetyl acetone, cyclohexanone, 2-heptanone, cyclopentanone, and diacetone alcohol; halogen compounds such as ethylene dichloride; ethers such as cyclohexyl methyl ether and dibutyl ether; amides such as 3-methoxy-N,N-dimethylpropanamide and 3-butoxy-N,N-dimethylpropanamide; and the like.

For details of the specific solvent, the description in paragraph "0223" in WO2015/166779A can be referred to, and what is described in the paragraph is incorporated into the present specification. In some cases, for environmental reasons, it is better to further reduce the amount of aromatic hydrocarbons as the specific solvent (for example, the amount of the aromatic hydrocarbons can be set to be equal to or smaller than 50 mass parts per million (ppm), equal to or smaller than 10 mass ppm, or equal to or smaller than 1 mass ppm with respect to the total amount of solvents).

Particularly, in a case where developability is imparted to the composition, in view of further improving developability, esters, alcohols, or ketones are preferable.

One kind of specific solvent may be used singly, or two or more kinds of specific solvents may be used in combination. In a case where two or more kinds of specific solvents are used in combination, a mixed solution is preferable which is constituted with two or more kinds of solvents selected from methyl 3-ethoxypropionate, ethyl 3-ethoxypropionate, ethyl cellosolve acetate, ethyl lactate, diethylene glycol dimethyl ether, butyl acetate, methyl 3-methoxypropionate, 2-heptanone, cyclohexanone, ethyl carbitol acetate, butyl carbitol acetate, propylene glycol monomethyl ether (PGME), and propylene glycol monomethyl ether acetate (PGMEA).

In the present invention, it is preferable to use a specific solvent with a small metal content. The metal content in the specific solvent is preferably equal to or smaller than 10 mass parts per billion (ppb), for example. If necessary, a solvent with a metal content of a mass parts per trillion (ppt) level may be used, and such a high-purity solvent is provided from a Toyo Gosei Co., Ltd., for example (The Chemical Daily Co., Ltd., Nov. 13, 2015).

Examples of methods for removing impurities such as metals from the specific solvent include distillation (molecular distillation, thin film distillation, and the like) and filtration using a filter. The pore size of the filter used for filtration is preferably equal to or smaller than 10 nm, more preferably equal to or smaller than 5 nm, and even more preferably equal to or smaller than 3 nm. As materials of the filter, polytetrafluoroethylene, polyethylene, and nylon are preferable.

The specific solvent may contain isomers (compounds of the same atomic number that have different structures). The specific solvent may contain only one kind of isomer or a plurality of kinds of isomers.

In the present invention, the content rate of a peroxide in the specific solvent is preferably equal to or lower than 0.8 mmol/L. It is more preferable that the specific solvent substantially does not contain a peroxide.

It is preferable that the content of the specific solvent is set such that the concentration of solid contents in the composition becomes 1% to 90% by mass. The upper limit of the content of the specific solvent is more preferably equal to or smaller than 80% by mass, and the lower limit thereof is more preferably equal to or greater than 10% by mass.

The composition may contain a solvent other than the specific solvent.

The content of the specific solvent with respect to the total mass of solvents is equal to or greater than 50% by mass for example, preferably equal to or greater than 70% by mass, more preferably equal to or greater than 85% by mass, even more preferably equal to or greater than 95% by mass, particularly preferably equal to or greater than 98% by mass, and most preferably 100% by mass.

In a case where two or more kinds of specific compounds are used in combination, the total content thereof is preferably within the above range.

It is preferable that the composition substantially does not contain a polar solvent. The polar solvent refers to a solvent which is selected from an amide-based solvent, a sulfoxide-based solvent, and a nitrile-based solvent and has a solubility parameter equal to or higher than 21 $mPa^{1/2}$. Furthermore, "substantially does not contain a polar solvent" means that the content of the polar solvent with respect to the total amount of the composition is equal to or smaller than 1% by mass. The content of the polar solvent with respect to the total amount of the composition is preferably equal to or smaller than 0.5% by mass, and more preferably equal to or smaller than 0.1% by mass.

<Resin>

The composition contains a resin.

The resin is mixed with the composition so as to disperse the specific compound in the composition and mixed as a binder, for example. The resin which is used mainly for dispersing a component having properties of particles such as the specific compound in the composition is referred to as dispersant as well. The aforementioned use of the resin is merely an example, and the resin can also be used for purposes other than the aforementioned use.

The weight-average molecular weight (Mw) of the resin is preferably 2,000 to 2,000,000. The upper limit thereof is preferably equal to or smaller than 1,000,000, and more preferably equal to or smaller than 500,000. The lower limit thereof is preferably equal to or greater than 3,000, and more preferably equal to or greater than 5,000.

Examples of the resin include a (meth)acryl resin, a (meth)acrylamide resin, an epoxy resin, an ene-thiol resin, a polycarbonate resin, a polyether resin, a polyarylate resin, a polysulfone resin, a polyether sulfone resin, a polyvphenylene resin, a polyarylene ether phosphine oxide resin, a polyimide resin, a polyamide imide resin, a polyolefin resin, a cyclic olefin resin, a polyester resin, a styrene resin, a siloxane resin, and the like.

In the present invention, as the resin, a resin (hereinafter, referred to as resin of high refractive index as well) having a refractive index equal to or higher than 1.7 for near infrared rays may also be used. The refractive index of the resin for near infrared rays is preferably 1.7 to 4.0. The lower limit thereof is preferably equal to or higher than 1.75, more preferably equal to or higher than 1.8, and even more preferably equal to or higher than 1.85. The upper limit thereof is preferably equal to or lower than 3.9, more preferably equal to or lower than 3.5, and even more preferably equal to or lower than 3.0. The refractive index is preferably a value for light of any wavelength among 810 nm, 850 nm, and 940 nm. In a case where the film according to an embodiment of the present invention is used in an infrared sensor, the value of refractive index is preferably a value for near infrared rays of a wavelength used for detecting infrared by using the same infrared sensor. The resin of high refractive index can be used as a binder or a dispersant.

The refractive index of the resin can be measured in an uncured state by the following method. Specifically, in the measurement method, a film having a thickness of 300 nm that is formed only of a resin to be measured is prepared on a silicon wafer, and then the refractive index of the obtained film is measured using an ellipsometer (LAMBDA ACE RE-3300 (trade name), manufactured by Dainippon Screen Mfg. Co., Ltd.).

From the viewpoint of developability, the resin may contain an acid group. Examples of the acid group include a carboxy group, a phosphoric acid group, a sulfo group, a phenolic hydroxyl group, and the like. One kind of acid group may be used singly, or two or more kinds of acid groups may be used in combination. The resin having an acid group can also be used as an alkali-soluble resin or a dispersant.

The weight-average molecular weight (Mw) of the resin having an acid group is preferably 5,000 to 200,000. The upper limit thereof is preferably equal to or smaller than 100,000, and more preferably equal to or smaller than 20,000. The number-average molecular weight (Mn) of the resin having an acid group is preferably 1,000 to 20,000.

The acid value of the resin having an acid group is preferably 30 to 500 mgKOH/g. The lower limit thereof is more preferably equal to or greater than 50 mgKOH/g, and even more preferably equal to or greater than 70 mgKOH/g. The upper limit thereof is more preferably equal to or smaller than 400 mgKOH/g, and even more preferably equal to or smaller than 200 mgKOH/g, particularly preferably equal to or smaller than 150 mgKOH/g, and most preferably equal to or smaller than 120 mgKOH/g.

As the resin having an acid group, a polymer having a carboxy group on a side chain is preferable. Specific examples thereof include a methacrylic acid copolymer, an acrylic acid copolymer, an itaconic acid copolymer, a crotonic acid copolymer, a maleic acid copolymer, a partially esterified maleic acid copolymer, an alkali-soluble phenol resin such as a novolac resin, an acidic cellulose derivative having a carboxy group on a side chain, and a resin obtained by adding an acid anhydride to a polymer having a hydroxyl group. Particularly, a copolymer of (meth)acrylic acid and another monomer copolymerizable with the (meth)acrylic acid is suitable as an alkali-soluble resin.

Examples of another monomer copolymerizable with the (meth)acrylic acid include alkyl (meth)acrylate, aryl (meth)acrylate, a vinyl compound, and the like. Examples of the alkyl (meth)acrylate and the aryl (meth)acrylate include methyl (meth)acrylate, ethyl (meth)acrylate, propyl (meth)acrylate, butyl (meth)acrylate, isobutyl (meth)acrylate, pentyl (meth)acrylate, hexyl (meth)acrylate, octyl (meth)acrylate, phenyl (meth)acrylate, benzyl (meth)acrylate, tolyl (meth)acrylate, naphthyl (meth)acrylate, cyclohexyl (meth)acrylate, and the like. Examples of the vinyl compound include styrene, α-methyl styrene, vinyl toluene, glycidyl methacrylate, acrylonitrile, vinyl acetate, N-vinylpyrrolidone, tetrahydrofurfuryl methacrylate, a polystyrene macromonomer, a polymethyl methacrylate macromonomer, and the like. As another monomer described above, the N position-substituted maleimide monomer (for example, N-phenylmaleimide, N-cyclohexylmaleimide, and the like) described in JP1999-300922A (JP-H10-300922A) can also be used. As another monomer copolymerizable with (meth) acrylic acid, one kind of monomer may be used singly, or two or more kinds of monomers may be used in combination.

As the resin having an acid group, a benzyl (meth) acrylate/(meth)acrylic acid copolymer, a benzyl (meth)acrylate/(meth)acrylic acid/2-hydroxyethyl (meth)acrylate copolymer, or a multi-component copolymer formed of benzyl (meth)acrylate/(meth)acrylic acid/another monomer is preferable. Furthermore, a resin obtained by copolymerizing 2-hydroxyethyl (meth)acrylate, a 2-hydroxypropyl (meth) acrylate/polystyrene macromonomer/benzyl methacrylate/methacrylic acid copolymer, a 2-hydroxy-3-phenoxypropyl acrylate/polymethyl methacrylate macromonomer/benzyl methacrylate/methacrylic acid copolymer, a 2-hydroxyethyl methacrylate/polystyrene macromonomer/methyl methacrylate/methacrylic acid copolymer, or a 2-hydroxyethyl methacrylate/polystyrene macromonomer/benzyl methacrylate/methacrylic acid copolymer described in JP1995-140654A (JP-H07-140654A), and the like are also preferable.

It is also preferable that the resin having an acid group contains a polymer obtained by polymerizing a monomer component containing a compound represented by General Formula (ED1) and/or a compound represented by General Formula (ED2) (hereinafter, these compounds will be referred to as "ether dimers" in some cases).

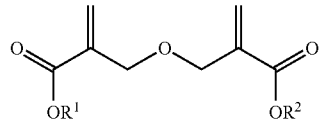

(ED1)

In General Formula (ED1), $R^1$ and $R^2$ each independently represent a hydrogen atom or a hydrocarbon group having 1 to 25 carbon atoms.

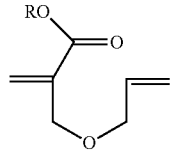

(ED2)

In General Formula (ED2), R represents a hydrogen atom or an organic group having 1 to 30 carbon atoms. Regarding specific examples of General Formula (ED2), the description in JP2010-168539A can be referred to.

Regarding specific examples of the ether dimers, for example, paragraph "0317" in JP2013-029760A can be referred to, and what is described in the paragraph is incorporated into the present specification. One kind of ether dimer may be used singly, or two or more kinds of ether dimers may be used.

The resin containing an acid group may contain a repeating unit derived from a compound represented by General Formula (X).

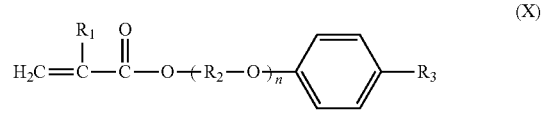

(X)

In General Formula (X), $R_1$ represents a hydrogen atom or a methyl group, $R_2$ represents an alkylene group having 2 to 10 carbon atoms, and $R_3$ represents a hydrogen atom or an alkyl group having 1 to 20 carbon atoms that may contain a benzene ring. n represents an integer of 1 to 15.

Regarding the resin having an acid group, the description in paragraphs "0558" to "0571" in JP2012-208494A (paragraphs "0685" to "0700" in US2012/0235099A corresponding to JP2012-208494A) and the description in paragraphs "0076" to "0099" in JP2012-198408A can be referred to, and what is described in the paragraphs is incorporated into the present specification.

The resin may have a curable group. Examples of the curable group include a group having an ethylenically unsaturated bond, an epoxy group, a methylol group, an alkoxysilyl group, and the like. Examples of the group having an ethylenically unsaturated bond include a vinyl group, a (meth)allyl group, an (meth)acryloyl group, a (meth)acryloyloxy group, and the like. Examples of the alkoxysilyl group include a monoalkoxysilyl group, a dialkoxysilyl group, and a trialkoxysilyl group. The resin having a curable group is also a curable compound.

Examples of the resin having a curable group include a DIANAL NR series (manufactured by Mitsubishi Rayon Co., Ltd.), Photomer 6173 (COOH-containing polyurethane acrylic oligomer, manufactured by Diamond Shamrock Co., Ltd.), VISCOAT R-264 and KS RESIST 106 (manufactured by OSAKA ORGANIC CHEMICAL INDUSTRY LTD), a CYCLOMER P series (for example, ACA 230AA) and a PLACCEL CF200 series (manufactured by Daicel Corporation), Ebecryl 3800 (manufactured by Daicel-UCB Company, Ltd.), ACRYCURE RD-F8 (manufactured by NIPPON SHOKUBAI CO., LTD.), and the like.

As the resin, it is also preferable to use MERPROOF G-0150M, G-0105SA, G-0130SP, G-0250SP, G-1005S, G-1005SA, G-1010S, G-2050M, G-01100, and G-01758 (manufactured by NOF CORPORATION, epoxy group-containing polymers), ARTON F4520 (manufactured by JSR Corporation), and the like.

The composition may contain a resin as a dispersant. Examples of the dispersant include polymer dispersants [for example, an amino group-containing resin (polyamide amine and a salt thereof), an oligoimine-based resin, a polycarboxylic acid and a salt thereof, a high-molecular-weight unsaturated acid ester, modified polyurethane, modified polyester, modified poly(meth)acrylate, a (meth)acrylic copolymer, and a naphthalene sulfonate formalin polycondensate] and the like. The polymer dispersants can be further classified into a linear polymer, a polymer having a modified terminal, a graft polymer, and a block polymer according to the structure.

The dispersant is preferably a resin having moieties (hereinafter, collectively referred to as "absorptive moiety") having an ability to be adsorbed onto the specific compound. Examples of the adsorptive moiety include a monovalent substituent having at least one kind of group selected from the group consisting of an acid group, a urea group, a urethane group, a group having a coordinating oxygen atom, a group having a basic nitrogen atom, a heterocyclic group, an alkyloxycarbonyl group, an alkylaminocarbonyl group, a carboxy group, a sulfonamide group, an alkoxysilyl group, an epoxy group, an isocyanate group, and a hydroxyl group, and the like. The adsorptive moiety is preferably an acid-based adsorptive moiety. Examples of the acid-based adsorptive moiety include an acid group and the like. Particularly, it is preferable that the acid-based adsorptive moiety has at least one of a phosphorus atom-containing group or a carboxy group. Examples of the phosphorus atom-containing group include a phosphoric acid ester group, a polyphosphoric acid ester group, a phosphoric acid group, and the like. For details of the adsorptive moiety, paragraphs "0073" to "0080" in JP2015-034961A can be referred to, and what is described in the paragraphs is incorporated into the present specification.

In the present invention, a dendrimer can be used in the resin as a dispersant. As the dendrimer, a resin represented by General Formula (111) is preferable.

In General Formula (111), $R^1$ represents an (m+n)-valent linking group, and $R^2$ represents a single bond or a divalent linking group. $A^1$ represents a monovalent substituent having at least one kind of group selected from the group consisting of an acid group, a urea group, a urethane group, a group having a coordinating oxygen atom, a group having a basic nitrogen atom, a heterocyclic group, an alkyloxycarbonyl group, an alkylaminocarbonyl group, a carboxy group, a sulfonamide group, an alkoxysilyl group, an epoxy group, an isocyanate group, and a hydroxyl group. n pieces of $A^1$'s and $R^2$'s may be the same as or different from each other respectively. m represents a positive number equal to or smaller than 8, n represents 1 to 9, and m+n equals 3 to 10. $P^1$ represents a monovalent polymer chain. m pieces of $P^1$'s may be the same as or different from each other.

Examples of the (m+n)-valent linking group represented by $R^1$ in General Formula (111) include groups constituted with 1 to 100 carbon atoms, 0 to 10 nitrogen atoms, 0 to 50 oxygen atoms, 1 to 200 hydrogen atoms, and 0 to 20 sulfur atoms. For details of the (m+n)-valent linking group, paragraphs "0076" to "0084" in JP2007-277514A can be referred to, and what is described in the paragraphs is incorporated into the present specification.

As the monovalent polymer chain represented by $P^1$ in General Formula (111), a monovalent polymer chain having a repeating unit derived from a vinyl compound is preferable. For details of the polymer chain, paragraphs "0087" to "0098" in JP2007-277514A can be referred to, and what is described in the paragraphs is incorporated into the present specification.

Examples of the divalent linking group represented by $R^2$ in General Formula (111) include groups constituted with 1 to 100 carbon atoms, 0 to 10 nitrogen atoms, 0 to 50 oxygen atoms, 1 to 200 hydrogen atoms, and 0 to 20 sulfur atoms. For details of the divalent linking group, paragraphs "0071" to "0075" in JP2007-277514A can be referred to, and what is described in the paragraphs is incorporated into the present specification.

For details of the monovalent substituent represented by $A^1$ in General Formula (111), paragraphs "0041" to "0070" in JP2007-277514A can be referred to, and what is described in the paragraphs is incorporated into the present specification.

Regarding the resin represented by General Formula (111), the description in paragraph "0039" in JP2007-277514A (paragraphs "0053" in WO2010/0233595A corresponding to JP2007-277514A), the description in paragraphs "0081" to "0117" in JP2015-034961A, and the description in Japanese Patent No. 5909468, Japanese Patent No. 5894943, and Japanese Patent No. 5894944 can be referred to, and what is described in the paragraphs is incorporated into the present specification. Furthermore, specific examples of the resin represented by General Formula (111) include the following resin.

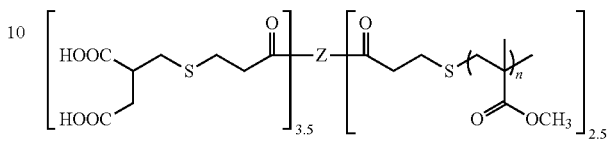

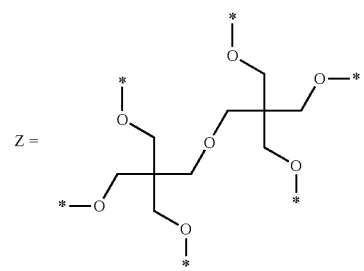

In the present invention, the resin as a dispersant is preferably a polymer containing a repeating unit having a polymer chain. More specifically, as the resin, a graft copolymer containing a repeating unit represented by any of General Formula (11) to General Formula (14) can also be used.

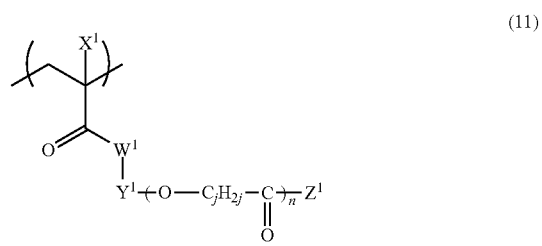

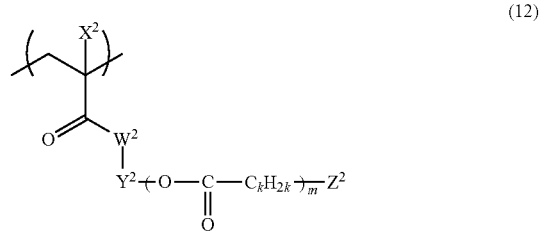

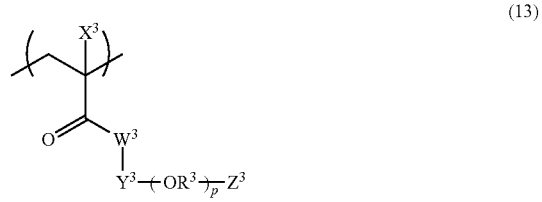

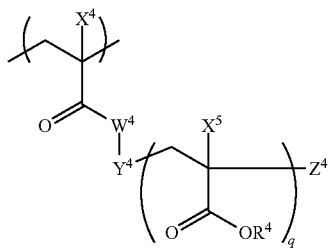

In General Formula (11) to General Formula (14), $W^1$, $W^2$, $W^3$, and $W^4$ each independently represent an oxygen atom or NH, $X^1$, $X^2$, $X^3$, $X^4$, and $X^5$ each independently represent a hydrogen atom or a monovalent group, $Y^1$, $Y^2$, $Y^3$, and $Y^4$ each independently represent a divalent linking group, $Z^1$, $Z^2$, $Z^3$, and $Z^4$ each independently represent a monovalent group, $R^3$ represents an alkylene group, $R^4$ represents a hydrogen atom or a monovalent group, n, m, p, and q each independently represent an integer of 1 to 500, and j and k each independently represent an integer of 2 to 8. In General Formula (13), in a case where p is 2 to 500, a plurality of $R^3$'s may be the same as or different from each other. In General Formula (14), in a case where q is 2 to 500, a plurality of $X^5$'s and $R^4$'s may be the same as or different from each other respectively.

Regarding the graft copolymer, the description in paragraphs "0025" to "0094" in JP2012-255128A can be referred to, and what is described in the paragraphs is incorporated into the present specification. Specific examples of the graft copolymer include the following resin and the resin described in paragraphs "0072" to "0094" in JP2012-255128A, and what is described in the paragraphs is incorporated into the present specification.

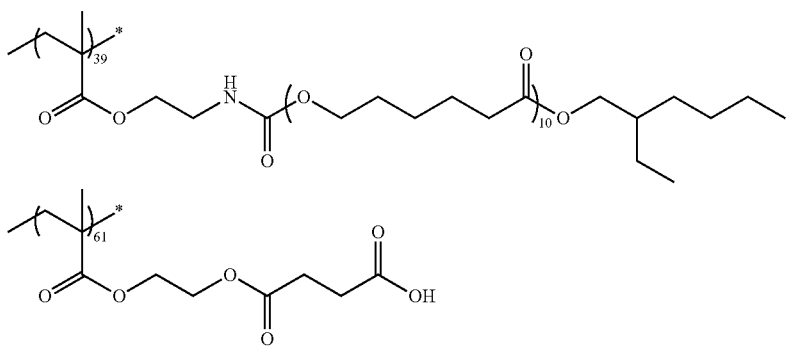

In the present invention, as the resin as a dispersant, it is also possible to use an oligoimine-based dispersant containing a basic nitrogen atom on at least one of a main chain or a side chain. As the oligoimine-based dispersant, a resin is preferable which has a repeating unit having a partial structure X containing a functional group with a pKa equal to or smaller than 14 and a side chain containing an oligomer chain or polymer chain Y constituted with 40 to 10,000 atoms, and has a basic nitrogen atom on at least one of a main chain or a side chain.

The basic nitrogen atom is not particularly limited as long as it is a nitrogen atom having basicity. The resin preferably contains a structure having a nitrogen atom with a pKb equal to or smaller than 14, and more preferably contains a structure having a nitrogen atom with a pKb equal to or smaller than 10. In the present invention, pKb (basic strength) refers to a pKb in water at 25° C. pKb is one of the parameters for quantitatively expressing the strength of a base, and has the same definition as the basicity constant. The basic strength pKb and the acidic strength pKa have a relationship of pKb=14−pKa.

Examples of the oligoimine-based dispersant include a resin containing a repeating unit represented by General Formula (I-1) and at least one of a repeating unit represented by General Formula (I-2) or a repeating unit represented by General Formula (I-2a), and the like.

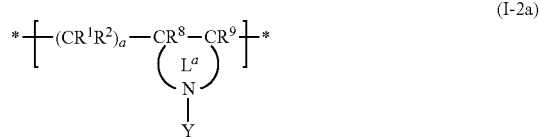

$R^1$, $R^2$, $R^8$, and $R^9$ each independently represent a hydrogen atom, a halogen atom, or an alkyl group (preferably having 1 to 6 carbon atoms).

a's each independently represent an integer of 1 to 5.

* represents a linking portion between repeating units.

L represents a single bond, an alkylene group (preferably having 1 to 6 carbon atoms), an alkenylene group (preferably having 2 to 6 carbon atoms), an arylene group (preferably having 6 to 24 carbon atoms), a heteroarylene group (preferably having 1 to 6 carbon atoms), an imino group (preferably having 0 to 6 carbon atoms), an ether group, a thioether group, a carbonyl group, or a linking group formed of a combination of these. L is preferably a single bond or —$CR^5R^6$—$NR^7$— (an imino group is on X or Y). $R^5$ and $R^6$ each independently represent a hydrogen atom, a halogen atom, or an alkyl group (preferably having 1 to 6 carbon atoms), and $R^7$ represents a hydrogen atom or an alkyl group having 1 to 6 carbon atoms.

$L^a$ is a structural moiety forming a ring structure together with $CR^8CR^9$ and N. $L^a$ is preferably a structural moiety forming a non-aromatic heterocyclic ring having 3 to 7 carbon atoms together with carbon atoms in $CR^8CR^9$.

X represents a group having a functional group with a pKa equal to or smaller than 14.

Y represents an oligomer chain or a polymer chain constituted with 40 to 10,000 atoms.

The dispersant (oligoimine-based dispersant) may further contain, as a copolymer component, one or more kinds of repeating units selected from the repeating units represented by General Formula (I-3), General Formula (I-4), and General Formula (I-5). In a case where the dispersant contains such repeating units, the dispersibility of the compound represented by General Formula (I) can be further improved.

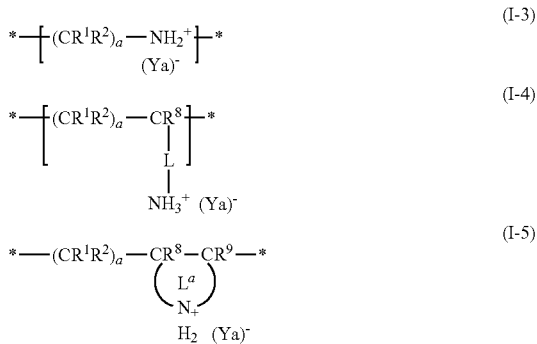

$R^1$, $R^2$, $R^8$, $R^9$, L, $L^a$, a, and * have the same definition as $R^1$, $R^2$, $R^8$, $R^9$, L, $L^a$, a, and * in General Formulae (I-1), (I-2), and (I-2a). Ya represents an anion group-containing side chain constituted with 40 to 10,000 atoms.

Regarding the oligoimine-based dispersant, the description in paragraphs "0118" to "0190" in JP2015-034961A can be referred to, and what is described in the paragraphs is incorporated into the present specification. Specifically, as the oligoimine-based dispersant, for example, it is possible to use the following resin and the resins described in paragraphs "0169" to "0190" in JP2015-034961A.

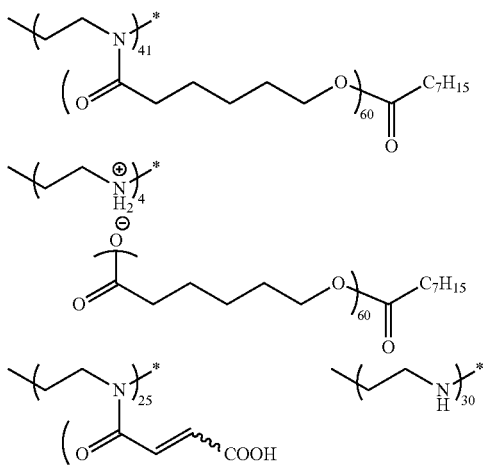

The dispersant is also available as a commercial product. Specifically, examples thereof include a DISPERBYK series (for example, DISPERBYK 103 and 111) manufactured by BYK-Chemie GmbH, and the like. Furthermore, the pigment dispersants described in paragraphs "0041" to "0130" in JP2014-130338A can also be used, and what is described in the paragraphs is incorporated into the present specification. In addition, the resin having an acid group described above and the like can also be used as the dispersant.

It is preferable that the resin (a dispersant and a binder) has a carbon-carbon double bond group in a molecule. This is because in a case where the resin (a dispersant and a binder) has a carbon-carbon double bond group in a molecule, the light fastness of the obtained film is further improved.

In the composition, the content of the resin with respect to the total solid content in the composition is preferably 1% to 99.9% by mass. The lower limit thereof is more preferably equal to or greater than 10% by mass, even more preferably equal to or greater than 20% by mass, and particularly preferably equal to or greater than 30% by mass. The upper limit thereof is more preferably equal to or smaller than 90% by mass, and even more preferably equal to or smaller than 80% by mass.

In a case where the aforementioned resin of high refractive index is used as a resin, only the resin of high refractive index may be used as a resin, or the resin of high refractive index and a resin having a refractive index less than 1.7 for near infrared rays may be used in combination. Furthermore, the content of the resin of high refractive index in the total amount of resins is preferably 1% to 100% by mass, and more preferably 10% to 100% by mass.

In the composition, the content of the dispersant with respect to the total solid content in the composition is preferably 1% to 80% by mass. The upper limit thereof is more preferably equal to or smaller than 70% by mass, and even more preferably equal to or smaller than 60% by mass. The lower limit thereof is more preferably equal to or greater than 3% by mass, and even more preferably equal to or greater than 4% by mass. Furthermore, the content of the dispersant with respect to 100 parts by mass of the compound represented by General Formula (I) is preferably 1 to 200 parts by mass. The upper limit thereof is more preferably equal to or smaller than 100 parts by mass, and even more preferably equal to or smaller than 50 parts by mass. The lower limit thereof is more preferably equal to or greater than 3 parts by mass, and even more preferably equal to or greater than 5 parts by mass.

The composition may contain one kind of resin or two or more kinds of resins.

<Other Components>

The composition may contain other components in addition to the components described above. The composition may contain, as other components, various additives such as a curable compound (including a polymerizable compound), a photopolymerizable compound, an antioxidant, a silane coupling agent, a polymerization inhibitor, a surfactant, an ultraviolet absorber, a filler (for example, inorganic particles), a curing accelerator, a thermal polymerization initiator, a thermal polymerization component, a plasticizer, a developability enhancer such as low-molecular-weight organic carboxylic acid, and an aggregation inhibitor.

(Curable Compound)

It is preferable that the composition contains a curable compound.

As the curable compound, it is possible to use known compounds that can be cured by a radical, an acid, or heat. Examples thereof include a compound that has a group having an ethylenically unsaturated bond, a compound having an epoxy group, a compound having a methylol group, and the like. Examples of the group having an ethylenically unsaturated bond include a vinyl group, a (meth)allyl group, a (meth)acryloyl group, a (meth)acryloyloxy group, and the like. Among these, a (meth)acryloyl group or a (meth) acryloyloxy group is preferable. The curable compound is preferably a polymerizable compound, and more preferably a radically polymerizable compound. Examples of the polymerizable compound include a compound that has a group having an ethylenically unsaturated bond, and the like.

The content of the curable compound with respect to the total solid content in the composition is preferably 1% to 80% by mass. The lower limit thereof is more preferably equal to or greater than 3% by mass, and even more preferably equal to or greater than 5% by mass. The upper limit thereof is more preferably equal to or smaller than 70% by mass, even more preferably equal to or smaller than 60% by mass, and particularly preferably equal to or smaller than 30% by mass.

One kind of curable compound may be used singly, or two or more kinds of curable compounds may be used in combination. In a case where the composition contains two or more kinds of curable compounds, the total content thereof is preferably within the above range.

Compound that has Group Having Ethylenically Unsaturated Bond (Polymerizable Compound)

In the present invention, as the curable compound, it is possible to use a compound (hereinafter, referred to as polymerizable compound as well) that has a group having an ethylenically unsaturated bond. The polymerizable compound is preferably a monomer. The molecular weight of the polymerizable compound is preferably 100 to 3,000. The upper limit thereof is more preferably equal to or smaller than 2,000, and even more preferably equal to or smaller than 1,500. The lower limit thereof is more preferably equal to or greater than 150, and even more preferably equal to or greater than 250. The polymerizable compound is preferably a (meth)acrylate compound having 3 to 15 functional groups, and more preferably a (meth)acrylate compound having 3 to 6 functional groups.

Regarding examples of the polymerizable compound, the description in paragraphs "0033" and "0034" in JP2013-253224A can be referred to, and what is described in the paragraphs is incorporated into the present specification. As the polymerizable compound, an ethylene oxy-modified pentaerythritol tetraacrylate (NK ESTER ATM-35E as a commercial product; manufactured by SHIN-NAKAMURA CHEMICAL CO., LTD.), a dipentaerythritol triacrylate (KAYARAD D-330 as a commercial product; manufactured by Nippon Kayaku Co., Ltd.), dipentaerythritol tetraacrylate (KAYARAD D-320 as a commercial product; manufactured by Nippon Kayaku Co., Ltd.), dipentaerythritol penta(meth) acrylate (KAYARAD D-310 as a commercial product; manufactured by Nippon Kayaku Co., Ltd, dipentaerythritol hexa(meth)acrylate (KAYARAD DPHA as a commercial product; manufactured by Nippon Kayaku Co., Ltd., A-DPH-12E; manufactured by SHIN-NAKAMURA CHEMICAL CO., LTD.), and a structure in which these (meth)acryloyl groups are bonded to each other through an ethylene glycol residue and/or a propylene glycol residue are preferable. Furthermore, oligomer-types of these can also be used. In addition, the description in paragraphs "0034" to "0038" in JP2013-253224A can be referred to, and what is described in the paragraphs is incorporated into the present specification. Examples of the polymerizable compound also include the polymerizable monomers described in paragraph "0477" in JP2012-208494A (paragraph "0585" in WO2012/0235099A corresponding to JP2012-208494A), and what is described in the paragraph is incorporated into the present specification. Moreover, diglycerin ethylene oxide (EO)-modified (meth)acrylate (M-460 as a commercial product; manufactured by TOAGOSEI CO., LTD.), dipentaerythritol tetraacrylate (manufactured by SHIN-NAKAMURA CHEMICAL CO., LTD., A-TMMT), and 1,6-hexanediol diacrylate (manufactured by Nippon Kayaku Co., Ltd., KAYARAD HDDA) are also preferable. Oligomer types of these can also be used. Examples thereof include RP-1040 (manufactured by Nippon Kayaku Co., Ltd.), and the like.

The polymerizable compound may have an acid group such as a carboxy group, a sulfo group, or a phosphoric acid group. Examples of the polymerizable compound having an acid group include an ester of an aliphatic polyhydroxy compound and an unsaturated carboxylic acid, and the like. The polymerizable compound having an acid group is preferably a polymerizable compound obtained by causing a non-aromatic carboxylic acid anhydride to react with an unreacted hydroxyl group of an aliphatic polyhydroxy compound so as to introduce an acid group into the compound, and more preferably an ester of the aforementioned polymerizable compound containing pentaerythritol and/or dipentaerythritol as the aliphatic polyhydroxy compound. Examples of commercial products thereof include polybasic acid-modified acryl oligomers manufactured by TOAGOSEI CO., LTD., such as M-305, M-510, M-520 in an ARONIX series, and the like. The acid value of the polymerizable compound having an acid group is preferably 0.1 to 40 mgKOH/g. The lower limit thereof is more preferably equal to or greater than 5 mgKOH/g. The upper limit thereof is more preferably equal to or smaller than 30 mgKOH/g.

In a preferred aspect, the polymerizable compound is a compound having a caprolactone structure. The polymerizable compound having a caprolactone structure is not particularly limited as long as the compound has a caprolactone structure in a molecule. Examples thereof include ε-caprolactone-modified polyfunctional (meth)acrylate obtained by esterifying a polyhydric alcohol, such as trimethylolethane, ditrimethylolethane, trimethylolpropane, ditrimethylolpropane, pentaerythritol, dipentaerythritol, tripentaerythritol, glycerin, diglycerol, or trimethylol melamine, (meth)acrylic acid, and ε-caprolactone. Regarding the polymerizable compound having a caprolactone structure, the description in paragraphs "0042" to "0045" in JP2013-253224A can be referred to, and what is described in the paragraphs is incorporated into the present specification. Examples of the polymerizable compound having a caprolactone structure include DPCA-20, DPCA-30, DPCA-60, and DPCA-120 marketed as a KAYARAD DPCA series from Nippon Kayaku Co., Ltd., SR-494 as tetrafunctional acrylate having 4 ethylene oxy chains and TPA-330 as trifunctional acrylate having 3 isobutylene oxy chains manufactured by Sartomer, and the like.

As the polymerizable compound, the urethane acrylates described in JP1973-041708B (JP-S48-041708B), JP1976-037193A (JP-H51-037193A), JP1990-032293B (JP-H02-032293B), and JP1990-016765B (JP-H02-016765B) and the urethane compounds having an ethylene oxide-based skeleton described in JP1983-049860B (JP-S58-049860B), JP1981-017654B (JP-S56-017654B), JP1987-039417B (JP-S62-039417B), and JP1987-039418B (JP-S62-039418B) are also suitable. Furthermore, it is possible to use addition-polymerizable compounds having an amino structure and/or a sulfide structure in a molecule described in JP1988-277653A (JP-S63-277653A), JP1988-260909A (JP-S63-

260909A), and JP1989-105238A (JP-H01-105238A). Examples of commercial products thereof include urethane oligomers UAS-10 and UAB-140 (manufactured by Sanyo-Kokusaku Pulp Co., Ltd.), UA-7200 (manufactured by SHIN-NAKAMURA CHEMICAL CO., LTD.), DPHA-40H (manufactured by Nippon Kayaku Co., Ltd.), UA-306H, UA-306T, UA-306I, AH-600, T-600, AI-600 (manufactured by KYOEISHA CHEMICAL Co., LTD), and the like.

The content of the polymerizable compound with respect to the total solid content in the composition is preferably 1% to 80% by mass. The lower limit thereof is more preferably equal to or greater than 3% by mass, and even more preferably equal to or greater than 5% by mass. The upper limit thereof is more preferably equal to or smaller than 70% by mass, and even more preferably equal to or smaller than 60% by mass.

Epoxy Group-Containing Compound

In the present invention, as the curable compound, an epoxy group-containing compound can also be used. Examples of the epoxy group-containing compound include a compound having one or more epoxy groups in one molecule. The epoxy group-containing compound is preferably a compound having 2 or more epoxy groups in one molecule. The number of epoxy groups in one molecule is preferably 1 to 100. For example, the upper limit thereof can be equal to or smaller than 10 or equal to or smaller than 5. The lower limit thereof is preferably equal to or greater than 2.

In the epoxy group-containing compound, an epoxy equivalent (=molecular weight of epoxy group-containing compound/number of epoxy groups) is preferably equal to or smaller than 500 g/equivalent, more preferably 100 to 400 g/equivalent, and even more preferably 100 to 300 g/equivalent.

The epoxy group-containing compound may be any of a low-molecular-weight compound (for example, a compound having a molecular weight less than 1,000) or a high-molecular-weight compound (macromolecule) (for example, a compound having a molecular weight equal to or greater than 1,000; in the case of polymer, the weight-average molecular weight thereof is equal to or greater than 1,000). The weight-average molecular weight of the epoxy group-containing compound is preferably 200 to 100,000, and more preferably 500 to 50,000. The upper limit of the weight-average molecular weight is more preferably equal to or smaller than 10,000, even more preferably equal to or smaller than 5,000, and particularly preferably equal to or smaller than 3,000.

As the epoxy group-containing compound, commercial products can also be used. Examples thereof include EHPE 3150 (manufactured by Daicel Corporation), EPICLON N-695 (manufactured by DIC Corporation), and the like. Furthermore, as the epoxy group-containing compound, it is possible to use the compounds described in paragraphs "0034" to "0036" in JP2013-011869A, paragraphs "0147" to "0156" in JP2014-043556A, and paragraphs "0085" to "0092" in JP2014-089408A. What is described in the paragraphs is incorporated into the present specification.

The content of the epoxy group-containing compound with respect to the total solid content in the composition is preferably 1% to 80% by mass. The lower limit thereof is more preferably equal to or greater than 3% by mass, and even more preferably equal to or greater than 5% by mass. The upper limit thereof is more preferably equal to or smaller than 70% by mass, and even more preferably equal to or smaller than 60% by mass. Only one kind of epoxy group-containing compound may be used, or two or more kinds of epoxy group-containing compounds may be used. In a case where the composition contains two or more kinds of epoxy group-containing compounds, the total content thereof is preferably within the above range.

(Photopolymerization Initiator)

The composition may contain a photopolymerization initiator.

Particularly, in a case where the composition contains a radically polymerizable compound, it is preferable that the composition contains a photopolymerization initiator. The photopolymerization initiator is not particularly limited and can be appropriately selected from known photopolymerization initiators. For example, as the photopolymerization initiator, a compound is preferable which exhibits photosensitivity to light rays in a range of ultraviolet rays to visible light. As the photopolymerization initiator, a photo-radical polymerization initiator is preferable.

Examples of the photopolymerization initiator include a halogenated hydrocarbon derivative (for example, a compound having a triazine skeleton, a compound having an oxadiazole skeleton, and the like), an acyl phosphine compound such as acyl phosphine oxide, hexaarylbiimidazole, an oxime compound such as an oxime derivative, an organic peroxide, a thio compound, a ketone compound, an aromatic onium salt, ketoxime ether, an aminoacetophenone compound, hydroxyacetophenone, and the like. As the photopolymerization initiator, from the viewpoint of exposure sensitivity, a compound is preferable which is selected from the group consisting of a trihalomethyl triazine compound, a benzyl dimethyl ketal compound, an α-hydroxyketone compound, an α-aminoketone compound, an acyl phosphine compound, a phosphine oxide compound, a metallocene compound, an oxime compound, a triarylimidazole dimer, an onium compound, a benzothiazole compound, a benzophenone compound, an acetophenone compound, a cyclopentadiene-benzene-iron complex, a halomethyl oxadiazole compound, and a 3-aryl-substituted coumarin compound, and a compound is more preferable which is selected from the group consisting of an oxime compound, an α-hydroxyketone compound, an α-aminoketone compound, and an acyl phosphine compound. In view of obtaining a better film, among the above, an oxime compound is even more preferable. Regarding the photopolymerization initiator, the description in paragraphs "0065" to "0111" in JP2014-130173A can be referred to, and what is described in the paragraphs is incorporated into the present specification.

As the photopolymerization initiator, an α-hydroxyketone compound, an α-aminoketone compound, and an acyl phosphine compound can also be suitably used. For example, the α-aminoketone compound described in 1998-291969A (JP-H10-291969A) and the acyl phosphine compound described in Japanese Patent No. 4225898 can also be used. Examples of commercial products of the α-hydroxyketone compound include IRGACURE-184, DAROCUR-1173, IRGACURE-500, IRGACURE-2959, and IRGACURE-127 (manufactured by BASF SE). Examples of commercial products of the α-aminoketone compound include IRGACURE-907, IRGACURE-369, IRGACURE-379, and IRGACURE-379EG (manufactured by BASF SE). Examples of commercial products of the acyl phosphine compound include IRGACURE-819 and DAROCUR-TPO (manufactured by BASF SE). Examples of commercial products of the oxime compound include IRGACURE-OXE01, IRGACURE-OXE02, IRGACURE-OXE03, and IRGACURE-OXE04 (manufactured by BASF SE), TR-PBG-304 (manufactured By Changzhou Tronly New Electronic Materials Co., Ltd.), ADEKA ARKLS NCI-831 (manufactured by ADEKA COR- PORATION), ADEKA ARKLS NCI-930 (manufactured by ADEKA CORPORATION), ADEKA OPTOMER N-1919 (manufactured by ADEKA CORPORATION, photopolymerization initiator 2 described in JP2012-014052A), and the like.

In the present invention, as the photopolymerization initiator, an oxime compound having a fluorene ring can also be used. Specific examples of the oxime compound having a fluorene ring include the compounds described in JP2014-137466A. What is described in the document is incorporated into the present specification.

In the present invention, as the photopolymerization initiator, an oxime compound having a fluorine atom can also be used. Specific examples of the oxime compound having a fluorine atom include the compound described in JP2010-262028A, the compounds 24 and 36 to 40 described in JP2014-500852A, the compound (C-3) described in JP2013-164471A, and the like. What is described in the documents is incorporated into the present specification.

In the present invention, as the photopolymerization initiator, an oxime compound having a nitro group can be used. It is also preferable that the oxime compound having a nitro group is made into a dimer. Specific examples of the oxime compound having a nitro group include the compounds described in paragraphs "0031" to "0047" in JP2013-114249A and paragraphs "0008" to "0012" and "0070" to "0079" in JP2014-137466A, the compounds described in paragraphs "0007" to "0025" in Japanese Patent No. 4223071, and ADEKA ARKLS NCI-831 (manufactured by ADEKA CORPORATION).

Specific examples of the oxime compound preferably used in the present invention will be shown below, but the present invention is not limited thereto.

(C-1)
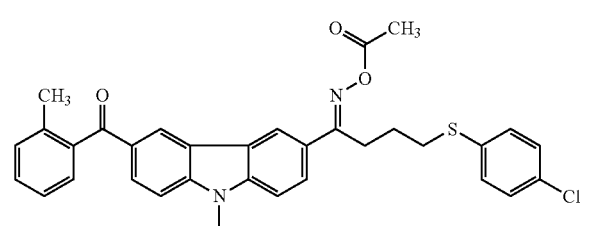

(C-2)
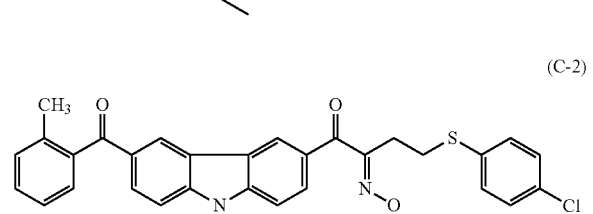

(C-3)
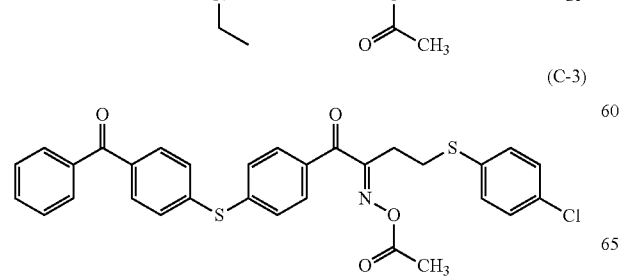

(C-4)
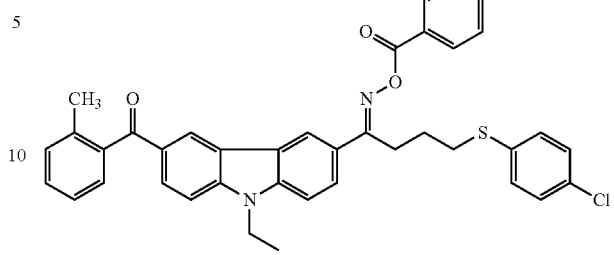

(C-5)
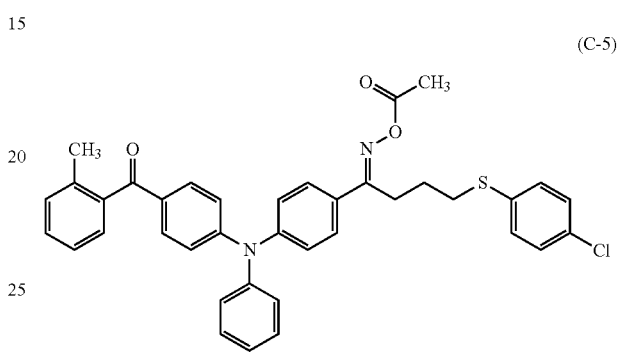

(C-6)
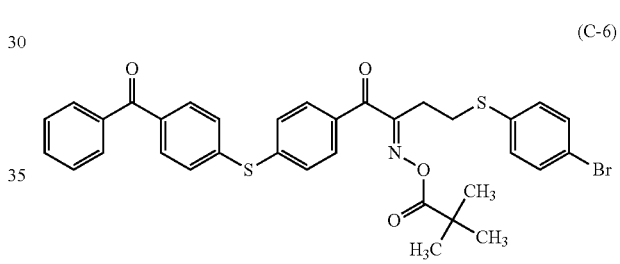

(C-7)

(C-8)
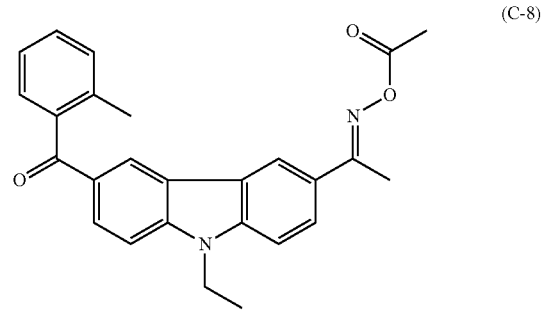

(C-9)
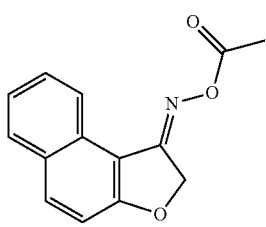

(C-14)
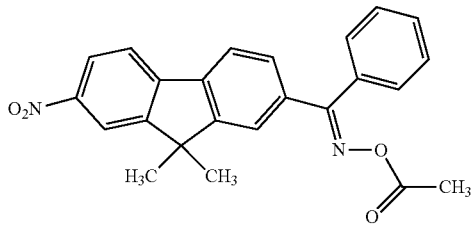

(C-10)
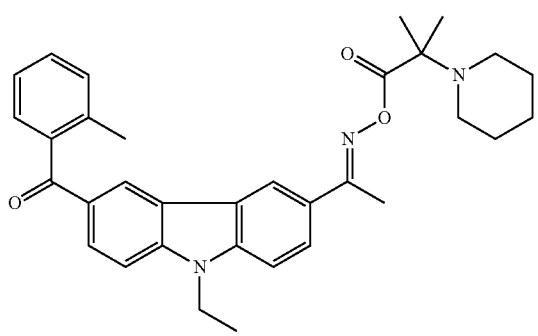

(C-11)
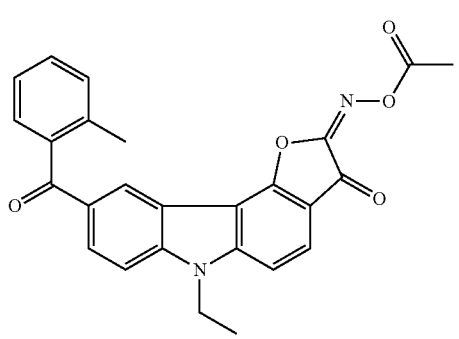

(C-12)
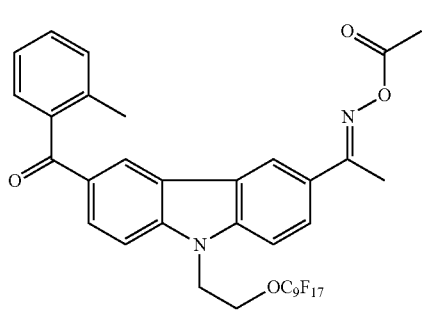

(C-13)
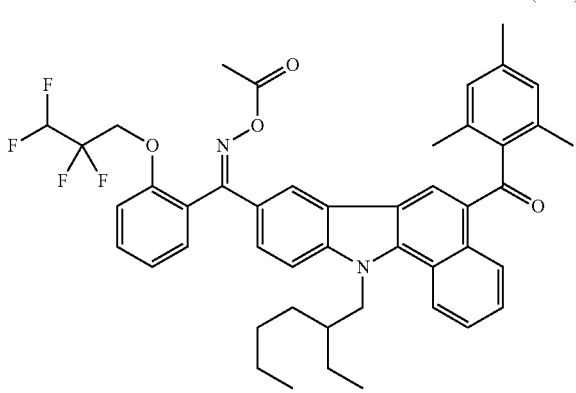

As the oxime compound, a compound having maximum absorption in a wavelength range of 350 nm to 500 nm is preferable, and a compound having maximum absorption in a wavelength range of 360 nm to 480 nm is more preferable. Furthermore, as the oxime compound, a compound having high absorbance at 365 nm and 405 nm is preferable.

From the viewpoint of sensitivity, a molar absorption coefficient of the oxime compound at 365 nm or 405 nm is preferably 1,000 to 300,000, more preferably 2,000 to 300,000, and even more preferably 5,000 to 200,000.

The molar absorption coefficient of a compound can be measured using known methods. For example, it is preferable to measure the molar absorption coefficient by using an ultraviolet-visible spectrophotometer (Cary-5 spectrophotometer manufactured by Varian Medical Systems, Inc.) and an ethyl acetate solvent at a concentration of 0.01 g/L.

It is also preferable that the photopolymerization initiator contains an oxime compound and an α-aminoketone compound. In a case where the compounds are used in combination, developability is improved, and it is easy to form a pattern having excellent rectangularity. In a case where the oxime compound and the α-aminoketone compound are used in combination, the content of the α-aminoketone compound with respect to 100 parts by mass of the oxime compound is preferably 50 to 600 parts by mass, and more preferably 150 to 400 parts by mass.

The content of the photopolymerization initiator with respect to the total solid content in the composition is preferably 0.1% to 50% by mass, more preferably 0.5% to 30% by mass, even more preferably 1% to 20% by mass, and particularly preferably 1% to 10% by mass.

In a case where the content of the photopolymerization initiator is within the above range, it is easy to form a pattern having excellent sensitivity and excellent rectangularity. The composition may contain only one kind of photopolymerization initiator or two or more kinds of photopolymerization initiators. In a case where the composition contains two or more kinds of photopolymerization initiators, the total content thereof is preferably within the above range.

(Antioxidant)

The composition may contain an antioxidant.

Examples of the antioxidant include a phenol compound, a phosphorous acid ester compound, a thioether compound, and the like. As the antioxidant, a phenol compound having a molecular weight equal to or greater than 500, a phosphorous acid ester compound having a molecular weight equal to or greater than 500, or a thioether compound having a molecular weight equal to or greater than 500 is preferable. Two or more kinds of the above compounds may be used by being mixed together. As the phenol compound, it is possible to use any phenol compound known as a phenol-based antioxidant, and a multi-substituted phenol-based compound is preferable. The multi-substituted phenol-based compound is roughly classified into three types (a hindered type, a semi-hindered type, and a less-hindered type) having different substitution positions and structures. As the antioxidant, a compound having a phenol group and a phosphorous acid ester group in the same molecule is preferably used. Furthermore, as the antioxidant, a phosphorous-based antioxidant is also preferably used. As the antioxidant, commercial products can also be used. Examples of commercial products of the antioxidant include ADEKA STAB AO-20, ADEKA STAB AO-30, ADEKA STAB AO-40, ADEKA STAB AO-50, ADEKA STAB AO-50F, ADEKA STAB AO-60, ADEKA STAB AO-60G, ADEKA STAB AO-80, and ADEKA STAB AO-330 (manufactured by ADEKA CORPORATION), and the like. In addition, regarding the antioxidant, the description in paragraphs "0033" to "0043" in JP2014-032380A can be referred to, and what is described in the paragraphs is incorporated into the present specification.

The content of the antioxidant with respect to the total solid content in the composition is preferably 0.01% to 20% by mass, and more preferably 0.3% to 15% by mass. Only one kind of antioxidant may be used, or two or more kinds of antioxidants may be used. In a case where the composition contains two or more kinds of antioxidants, the total content thereof is preferably within the above range.

(Silane Coupling Agent)

The composition may contain a silane coupling agent. In the present invention, the silane coupling agent means a silane compound having a hydrolyzable group and a functional group other than this. The hydrolyzable group refers to a substituent which is directly bonded to a silicon atom and can form a siloxane bond by at least any one of a hydrolysis reaction or a condensation reaction. Examples of the hydrolyzable group include a halogen atom, an alkoxy group, an acyloxy group, and the like. Among these, an alkoxy group is preferable. That is, as the silane coupling agent, a compound having an alkoxysilyl group is preferable. Furthermore, as the functional group other than the hydrolyzable group, a group expressing affinity by interacting or forming a bond with a resin is preferable. Examples of the functional group include a vinyl group, a styryl group, a (meth)acryloyl group, a mercapto group, an epoxy group, an oxetanyl group, an amino group, a ureide group, a sulfide group, an isocyanate group, a phenyl group, and the like. Among these, a (meth)acryloyl group or an epoxy group is preferable.

Specific examples of the silane coupling agent include 3-methacryloxypropyl methyl dimethoxysilane and the like. Examples of the silane coupling agent include the compounds described in paragraphs "0018" to "0036" in JP2009-288703A and the compounds described in paragraphs "0056" to "0066" in JP2009-242604A, and what is described in the paragraphs is incorporated into the present specification. As the silane coupling agent, commercial products can also be used. Examples of commercial products of the silane coupling agent include KBM-13, KBM-22, KBM-103, KBE-13, KBE-22, KBE-103, KBM-3033, KBE-3033, KBM-3063, KBM-3066, KBM-3086, KBE-3063, KBE-3083, KBM-3103, KBM-3066, KBM-7103, SZ-31, KPN-3504, KBM-1003, KBE-1003, KBM-303, KBM-402, KBM-403, KBE-402, KBE-403, KBM-1403, KBM-502, KBM-503, KBE-502, KBE-503, KBM-5103, KBM-602, KBM-603, KBM-903, KBE-903, KBE-9103, KBM-573, KBM-575, KBM-9659, KBE-585, KBM-802, KBM-803, KBE-846, KBE-9007, X-40-1053, X-41-1059A, X-41-1056, X-41-1805, X-41-1818, X-41-1810, X-40-2651, X-40-2655A, KR-513, KC-89S, KR-500, KR-516, KR-517, X-40-9296, X-40-9225, X-40-9246, X-40-9250, KR-401N, X-40-9227, X-40-9247, KR-510, KR-9218, KR-213, X-40-2308, and X-40-9238 manufactured by Shin-Etsu Silicones, and the like.

The content of the silane coupling agent with respect to the total solid content in the composition is preferably 0.01% to 15.0% by mass, and more preferably 0.05% to 10.0% by mass. Only one kind of silane coupling agent may be used, or two or more kinds of silane coupling agents may be used. In a case where the composition contains two or more kinds of silane coupling agents, the total content thereof is preferably within the above range.

(Polymerization Inhibitor)

The composition may contain a polymerization inhibitor.

Examples of the polymerization inhibitor include hydroquinone, p-methoxyphenol, di-tert-butyl-p-cresol, pyrogallol, tert-butylcatechol, benzoquinone, 4,4'-thiobis(3-methyl-6-tert-butylphenol), 2,2'-methylenebis(4-methyl-6-tert-butylphenol), and N-nitrosophenylhydroxyamine salt (an ammonium salt, a primary cerium salt, and the like). Among these, p-methoxyphenol is preferable. In some cases, the polymerization inhibitor functions as an antioxidant.

The content of the polymerization inhibitor with respect to 100 parts by mass of the photopolymerization initiator is preferably 0.01 parts by mass to 10 parts by mass, more preferably 0.01 to 8 parts by mass, and even more preferably 0.01 to 5 parts by mass.

(Surfactant)

From the viewpoint of further improving coating properties, the composition may contain various surfactants.

As the surfactants, it is possible to use various surfactants such as a fluorine-based surfactant, a nonionic surfactant, a cationic surfactant, an anionic surfactant, and a silicone-based surfactant. Regarding the surfactants, paragraphs "0238" to "0245" in WO2015/166779A can be referred to, and what is described in the paragraphs is incorporated into the present specification.

In a case where a fluorine-based surfactant is incorporated into the composition according to the embodiment of the present invention, the liquid characteristics (particularly, fluidity) of the composition prepared as a coating solution can be further improved, and the uniformity of coating thickness and the liquid saving properties can be further improved. In a case where a film is formed using a coating solution in which the composition containing a fluorine-based surfactant is used, the surface tension between a surface to be coated and the coating solution is reduced, wettability with respect to a surface to be coated is improved, and coating properties with respect to a surface to be coated are improved. Therefore, it is possible to more suitably form a film having a uniform thickness with a small thickness unevenness.

In the fluorine-based surfactant, a suitable fluorine content rate is 3% to 40% by mass. The fluorine content rate is more preferably 5% to 30% by mass, and particularly preferably 7% to 25% by mass. The fluorine-based surfactant in which the fluorine content rate is within the above range is effective in terms of the thickness uniformity of the coating film and liquid saving properties and exhibits excellent solubility in the composition.

Specific examples of the fluorine-based surfactant include the surfactants described in paragraphs "0060" to "0064" in JP2014-041318A (paragraphs "0060" to "0064" in WO2014/017669A corresponding to JP2014-041318A) and the like and the surfactants described in paragraphs "0117" to "0132" in JP2011-132503A, and what is described in the paragraphs is incorporated into the present specification.

Examples of commercial products of the fluorine-based surfactant include MEGAFACE F171, MEGAFACE F172, MEGAFACE F173, MEGAFACE F176, MEGAFACE F177, MEGAFACE F141, MEGAFACE F142, MEGAFACE F143, MEGAFACE F144, MEGAFACE R30, MEGAFACE F437, MEGAFACE F475, MEGAFACE F479, MEGAFACE F482, MEGAFACE F554, and MEGAFACE F780 (manufactured by DIC Corporation), FLUORAD FC430, FLUORAD FC431, and FLUORAD FC171 (manufactured by Sumitomo 3M Ltd.), SURFLON S-382, SURFLON SC-101, SURFLON SC-103, SURFLON SC-104, SURFLON SC-105, SURFLON SC1068, SURFLON SC-381, SURFLON SC-383, SURFLON S393, and SURFLON KH-40 (manufactured by ACG Inc.), PolyFox PF636, PF656, PF6320, PF6520, and PF7002 (manufactured by OMNOVA Solutions Inc.), and the like.

As the fluorine-based surfactant, an acrylic compound can also be suitably used which has a molecular structure having a functional group containing a fluorine atom that is volatilized due to the cleavage of the portion of the functional group containing the fluorine atom in a case where heat is applied to the compound. Examples of such a fluorine-based surfactant include a MEGAFACE DS series manufactured by DIC Corporation (The Chemical Daily Co., Ltd., Feb. 22, 2016), (Nikkei Inc, Feb. 23, 2016) such as MEGAFACE DS-21.

As the fluorine-based surfactant, a block copolymer can also be used. Examples thereof include the compounds described in JP2011-089090A. As the fluorine-based surfactant, a fluorine-containing polymer compound, which contains a repeating unit derived from a fluorine atom-containing (meth)acrylate compound and a repeating unit derived from a (meth)acrylate compound having 2 or more (preferably 5 or more) alkyleneoxy groups (preferably ethyleneoxy groups or propyleneoxy groups), can also be preferably used. The following compound is also an example of the fluorine-based surfactant used in the present invention.

Examples of the nonionic surfactant include glycerol, trimethylolpropane, trimethylolethane, ethoxylate and propoxylate of these (for example, glycerol propoxylate and glycerol ethoxylate), and the like. Examples thereof also include polyoxyethylene lauryl ether, polyoxyethylene stearyl ether, polyoxyethylene oleyl ether, polyoxyethylene octyl phenyl ether, polyoxyethylene nonyl phenyl ehter, polyethylene glycol dilaurate, polyethylene glycol distearate, a sorbitan fatty acid ester, PLURONIC L10, L31, L61, L62, 10R5, 17R2, and 25R2 (manufactured by BASF SE), TETRONIC 304, 701, 704, 901, 904, and 150R1 (manufactured by BASF SE), SOLSPERSE 20000 (manufactured by Lubrizol Japan Ltd.), NCW-101, NCW-1001, and NCW-1002 (manufactured by Wako Pure Chemical Industries, Ltd.), PIONIN D-6112, D-6112-W, and D-6315 (manufactured by TAKEMOTO OIL & FAT Co., Ltd.), OLFINE E1010, SURFYNOL 104, 400, and 440 (manufactured by Nissin Chemical Co., Ltd.), and the like.

As the fluorine-based surfactant, a vinyl ether polymerization-type fluorine-based surfactant can also be used. Examples of the vinyl ether polymerization-type fluorine-based surfactant include those described in Examples in JP2016-216602A (for example, a fluorine-based surfactant (1)) and the like.

The content of the surfactant with respect to the total solid content in the composition is preferably 0.001% to 5.0% by mass, and more preferably 0.005% to 3.0% by mass. Only one kind of surfactant may be used, or two or more kinds of fluorine-based surfactants may be used. In a case where the composition contains two or more kinds of surfactants, the total content thereof is preferably within the above range.

(Ultraviolet Absorber)

The composition may contain an ultraviolet absorber.

Examples of the ultraviolet absorber include a conjugated diene compound, an aminodiene compound, a salicylate compound, a benzophenone compound, a benzotriazole compound, an acrylonitrile compound, a hydroxyphenyl

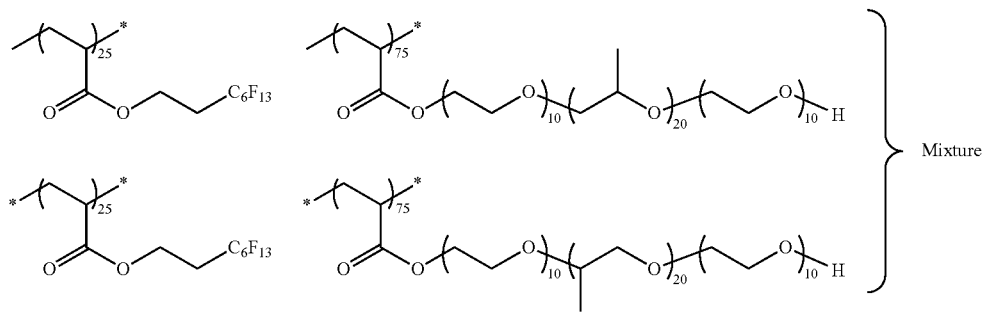

The weight-average molecular weight of the above compound is preferably 3,000 to 50,000. For example, the weight-average molecular weight of the above compound is 14,000. The proportion of repeating units in the above compound is expressed as "% by mass".

As the fluorine-based surfactant, it is also possible to use a fluorine-containing polymer having an ethylenically unsaturated group on a side chain. Specifically, examples thereof include the compounds described in paragraphs "0050" to "0090" and paragraphs "0289" to "0295" in JP2010-164965A, such as MEGAFACE RS-101, RS-102, RS-718K, and RS-72-K manufactured by DIC Corporation, and the like. As the fluorine-based surfactant, it is also possible to use the compounds described in paragraphs "0015" to "0158" in JP2015-117327A.

triazine compound, and the like. For details of these, the description in paragraphs "0052" to "0072" in JP2012-208374A and paragraphs "0317" to "0334" in JP2013-068814A can be referred to, and what is described in the paragraphs is incorporated into the present specification. Examples of commercial products of the conjugated diene compound include UV-503 (manufactured by DAITO CHEMICAL CO., LTD.), and the like. Furthermore, as the benzotriazole compound, a MYUA series manufactured by MIYOSHI OIL & FAT CO., LTD. (The Chemical Daily Co., Ltd., Feb. 1, 2016) may also be used.

The content of the ultraviolet absorber with respect to the total solid content in the composition is preferably 0.1% to 10% by mass, more preferably 0.1% to 5% by mass, and even more preferably 0.1% to 3% by mass. Only one kind of ultraviolet absorber may be used, or two or more kinds of ultraviolet absorbers may be used. In a case where the composition contains two or more kinds of ultraviolet absorbers, the total content thereof is preferably within the above range.

(Filler)

Examples of the filler include inorganic particles. As the inorganic particles, colorless, white, or transparent inorganic particles having a high refractive index are preferable. As the inorganic particles, oxide particles of titanium (Ti), zirconium (Zr), aluminum (Al), silicon (Si), zinc (Zn), or magnesium (Mg) are preferable, and titanium dioxide ($TiO_2$) particles, zirconium oxide ($ZrO_2$) particles, or silicon dioxide ($SiO_2$) particles are more preferable.

The primary particle diameter of the inorganic particles is not particularly limited, but is preferably 1 to 100 nm, more preferably 1 to 80 nm, and even more preferably 1 to 50 nm. In a case where the primary particle diameter of the inorganic particles is within the above range, dispersibility is further improved, and a refractive index and a transmittance are further improved.

The refractive index of the inorganic particles is not particularly limited. However, from the viewpoint of obtaining a high refractive index, the refractive index of the inorganic particles is preferably 1.75 to 2.70, and more preferably 1.90 to 2.70.

The specific surface area of the inorganic particles is not particularly limited, but is preferably 10 to 400 $m^2/g$, more preferably 20 to 200 $m^2/g$, and even more preferably 30 to 150 $m^2/g$.

The shape of the inorganic particles is not particularly limited, and examples thereof include a rice grain shape, a spherical shape, a cubical shape, a spindle shape, and an amorphous shape.

The surface of the inorganic particles may be treated with an organic compound. Examples of the organic compound used for the surface treatment include polyol, alkanolamine, stearic acid, a silane coupling agent, and a titanate coupling agent. Among these, stearic acid or a silane coupling agent is preferable.

In view of further improving weather fastness, it is also preferable that the surface of the inorganic particles is coated with an oxide of aluminum, silicon, zirconia, and the like.

As the inorganic particles, commercial products can also be preferably used.

One kind of inorganic particles may be used singly, or two or more kinds of inorganic particles may be used in combination.

(Curing Accelerator)

In a case where the composition contains a compound containing a cationically polymerizable group (for example, an epoxy group-containing compound) as a curable compound, it is preferable that the composition contains a curing accelerator.

Examples of the curing accelerator improving a curing speed include an acid anhydride, a base (aliphatic amine, aromatic amine, modified amine, and the like), an acid (sulfonic acid, phosphoric acid, carboxylic acid, and the like), polymercaptan, and the like. Among these, an acid anhydride is preferable, and an aliphatic acid anhydride is more preferable.

(Synergist)

In order to improve dispersibility, it is preferable to add a synergist, which is for adjusting the surface characteristics of the compound represented by General Formula (I), to the composition.

As the synergist, known dispersants can be used. As the synergist, dispersants that substantially do not have absorption at a wavelength of 400 to 700 nm are preferable. Among these, a compound is preferable which has the compound represented by General Formula (I) as a skeleton and contains an acidic group (a sulfonic acid group, a phosphoric acid group, or the like) and/or a basic group (an amino group or the like). In a case where the composition contains the synergist, the content of the synergist with respect to the compound represented by General Formula (I) is preferably 1% to 50% by mass, more preferably 3% to 30% by mass, and even more preferably 5% to 20% by mass.

<Method for Preparing Composition>

The composition can be prepared by mixing together the components described above. For preparing the composition, the components may be mixed together at once, or the components may be dissolved or dispersed in a solvent and then sequentially mixed together. For example, the composition may be prepared by simultaneously dissolving or dispersing all the components in a solvent. Furthermore, a composition may be prepared by dispersing components exhibiting the properties of particles (for example, the specific compound and the like) in a solvent and a resin, and the obtained composition and other components (for example, a binder, a curable compound, and the like) may be mixed together.

It is preferable that the manufacturing method of the composition includes a process of dispersing components (hereinafter, referred to as "particles" as well) exhibiting the properties of particles such as the specific compound. In the process of dispersing the particles, as mechanical force used for dispersing particles, for example, compression, squeezing, impact, shearing, cavitation, and the like are used. Specifically, examples of the process include a beads mill, a sand mill, a roll mill, a ball mill, a paint shaker, a microfluidizer, a high-speed impeller, a sand grinder, a flow jet mixer, a high-pressure wet atomization, ultrasonic dispersion, and the like. For pulverizing the particles in a sand mill (beads mill), it is preferable to treat the particles under the condition increasing a pulverization efficiency by means of using beads having a small diameter, increasing a filling rate of beads, and the like. Furthermore, after the pulverization treatment, it is preferable to remove coarse particles by filtration, centrifugation, and the like. In addition, as the particle dispersion process and dispersion machines, it is possible to suitably use the processes and dispersion machines described in "Complete Works of Dispersion Technique, JOHOKIKO CO., LTD., Jul. 15, 2005", "Dispersion Technique Focused on Suspension (Solid/Liquid Dispersion System) and Practice of Industrial Application Thereof, Comprehensive Data Package, publishing department of KEIEI KAIHATSU CENTER, Oct. 10, 1978", and paragraph "0022" in JP2015-157893A. Furthermore, in the process of dispersing the particles, the particles may be subjected to an atomization treatment through a salt milling step. Regarding materials, instruments, treatment conditions used in the salt milling step, and the like, for example, the description in JP2015-194521A and JP2012-046629A can be referred to.

At the time of preparing the composition, for the purpose of removing foreign substances, reducing defects, and the like, it is preferable to filter the composition by using a filter. As the filter, filters that have been conventionally used for filtration can be used without particular limitation. Examples thereof include filters using materials including a fluororesin such as polytetrafluoroethylene (PTFE), a polyamide-based resin such as nylon (for example, nylon-6 and nylon-6,6), and a polyolefin resin (including a high-density polyolefin resin and/or an ultra-high-molecular-weight polyolefin resin) such as polyethylene and polypropylene (PP). Among these materials, polypropylene (including high-density polypropylene) and nylon are preferable.

The pore size of the filter is preferably about 0.01 to 7.0 more preferably about 0.01 to 3.0 µm, and even more preferably about 0.05 to 0.5 µm. In a case where the pore size of the filter is within the above range, fine foreign substances can be reliably removed. It is also preferable to use fibrous filter materials. Examples of the fibrous filter materials include polypropylene fiber, nylon fiber, glass fiber, and the like. Specifically, examples thereof include filter cartridges such as an SBP type series (SBP008 and the like), a TPR type series (TPR002, TPR005, and the like), and an SHPX type series (SHPX003 and the like) manufactured by ROKI TECHNO CO., LTD.

In a case where a filter is used, different filters (for example, a first filter, a second filter, and the like) may be combined. At this time, the particles may be filtered only once or twice or more through each filter. In addition, filters having different pore sizes within the above range may be combined. Regarding the pore size, nominal values from filter makers can be referred to. Commercial filters can be selected from various filters provided from Pall Corporation (DFA4201NXEY and the like), ADVANTECH, Entegris Japan Co., Ltd. (former Micronics Japan Co., Ltd.), KITZ MICRO FILTER CORPORATION, and the like. As the second filter, a filter formed of the same material as the first filter and the like can be used. Furthermore, a mixed solution obtained by mixing together only the specific compound, a resin, and a solvent may be filtered through the first filter, other components may be mixed with the filtered solution, and then the obtained mixed solution may be filtered through the second filter.

[Compound]

The specific compound according to an embodiment of the present invention is preferably a compound represented by General Formula (III) or General Formula (V).

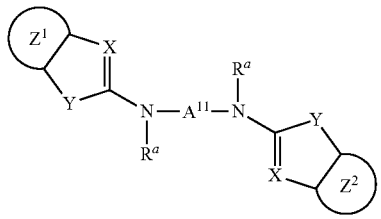

(III)

In General Formula (III), $A^{11}$ represents a heterocyclic group. X's each independently represent a nitrogen atom or $CR^d$. Y's each independently represent $—NR^e—$, $—S—$, or $—O—$. $R^a$, $R^d$, and $R^e$ each independently represent a hydrogen atom, an alkyl group, or an aryl group. $Z^1$ and $Z^2$ each independently represent a benzene ring or a naphthalene ring.

The heterocyclic group represented by $A^{11}$ has the same definition as the heterocyclic group represented by A in the compound represented by General Formula (I). As the heterocyclic group represented by $A^{11}$, particularly, a triazine ring group, a pyridine ring group, a pyrimidine ring group, or a group formed by the fusion of the partial structure represented by General Formula (IIA) with a benzene ring or a naphthalene ring is preferable, and a group formed by the fusion of the partial structure represented by General Formula (IIA) with a benzene ring or a naphthalene ring is more preferable.

$A^{11}$ may further have a substituent (for example, a group exemplified in the group of substituents T).

$R^a$ has the same definition as $R^a$ in General Formula (I), and preferred aspects thereof are also the same.

X and Y have the same definition as X and Y in General Formula (II) respectively, and preferred aspects thereof are also the same. Particularly, it is preferable that X represents a nitrogen atom and Y represents $—S—$.

$Z^1$ and $Z^2$ each independently represent a benzene ring or a naphthalene ring. Particularly, it is preferable that $Z^1$ and $Z^2$ represent a benzene ring. Furthermore, $Z^1$ and $Z^2$ may have a substituent (for example, a group exemplified in the group of substituents T).

The compound represented by General Formula (III) is preferably a compound represented by General Formula (IV).

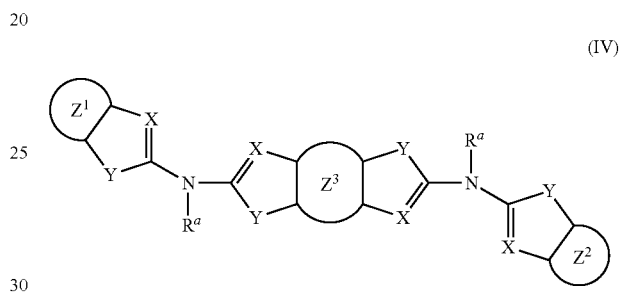

(IV)

$R^a$, $Z^1$, $Z^2$, X, and Y have the same definition as $R^a$, $Z^1$, $Z^2$, X, and Y in General Formula (III) respectively, and preferred aspects thereof are also the same.

$Z^3$ represents a benzene ring or a naphthalene ring. Particularly, it is preferable that $Z^3$ represents a benzene ring. Furthermore, $Z^3$ may have a substituent (for example, a group exemplified in the group of substituents T).

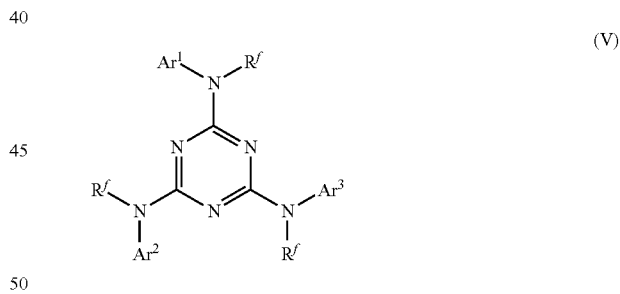

(V)

In General Formula (V), $R^f$ represents a hydrogen atom or an alkyl group. $Ar^1$ to $Ar^3$ each independently represent an aryl group or a heterocyclic group. Here, at least one of $Ar^1$, $Ar^2$, or $Ar^3$ represents a group represented by General Formula (VI).

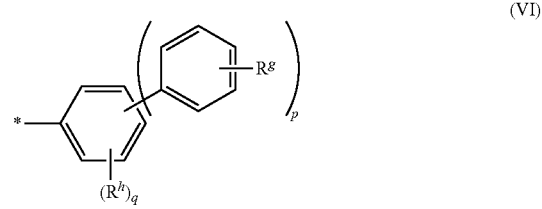

(VI)

In General Formula (VI), $R^g$ and $R^h$ each independently represent a substituent. p represents an integer of 1 to 5. q represents an integer of 0 to 4. * represents a binding position. In a case where there is a plurality of $R^g$'s and a plurality of $R^h$'s, the plurality of $R^g$'s may be the same as or different from each other, and the plurality of $R^h$'s may be the same as or different from each other.

In General Formula (V), the alkyl group represented by $R^f$ has the same definition as the alkyl group represented by $R^d$ and $R^e$ in General Formula (II), and preferred aspects thereof are also the same.

As $R^f$, particularly, a hydrogen atom is preferable.

The aryl group and the heterocyclic group represented by $Ar^1$ to $Ar^3$ have the same definition as the aryl group and the heterocyclic group represented by C in General Formula (I), and preferred aspects thereof are also the same.

in General Formula (VI), $R^g$ and $R^h$ each independently represent a substituent.

Examples of the substituent include the groups exemplified in the group of substituents T. As the substituent, particularly, in view of further increasing refractive index, for example, $-SR^{11}$ ($R^{11}$ is preferably an alkyl group having 1 to 3 carbon atoms, and more preferably a methyl group), a halogen atom (a fluorine atom, a chlorine atom, a bromine atom, or an iodine atom), a group having a conjugated double bond (for example, an aryl group which may further have a substituent; examples of the substituent include the groups exemplified in the group of substituents T, and among these, a phenyl group is preferable), a cyano group, a nitro group, an acetylamino group, or an alkyl group (preferably an alkyl group having 1 to 3 carbon atoms and more preferably a methyl group) is preferable.

As the substituent represented by $R^g$, particularly, a halogen atom, a group having a conjugated double bond, or a cyano group is more preferable, a halogen atom, an aryl group, or a cyano group is even more preferable, and a phenyl group, a biphenyl group, or a cyano group is most preferable.

p represents an integer of 1 to 5.

As p, in view of further increasing refractive index, 1 is preferable.

Furthermore, in view of further increasing refractive index, in a benzene ring substituted with $R^g$, the substitution position of $R^g$ is preferably para position for the position linked to a benzene ring that $R^h$ can substitute.

In a case where $R^g$ represents a phenyl group having a substituent, the substitution position of the substituent is preferably para position for a position linked to a phenylene group adjacent to $R^g$ in the phenyl group represented by $R^g$.

q represents an integer of 0 to 4. q is preferably 0 or 1, and more preferably 0.

* represents a position in which General Formula (VI) is bonded to a nitrogen atom indicated in General Formula (V).

In a case where there is a plurality of $R^g$'s and a plurality of $R^h$'s, the plurality of $R^g$'s may be the same as or different from each other, and the plurality of $R^h$'s may be the same as or different from each other.

[Use]

The use of the compound and the composition according to the embodiment of the present invention is not particularly limited. For example, the compound and the composition are useful as a member of high refractive index in a solid-state imaging element (a transparent film such as an undercoat layer or an adjacent layer of a microlens and a color filter and a white pixel of a color filter), a lens (a lens of eyeglasses, a lens for a digital camera, a Fresnel lens, a prism lens, and the like), an optical overcoating agent, a hardcoating agent, an antireflection film, optical fiber, a waveguide, a sealing material for a Light Emitting Diode (LED), a flattening material for LED, and a coating material for a solar cell.

<Film>

The film according to an embodiment of the present invention is a film obtained from the composition according to the embodiment of the present invention. In a case where the composition contains a curable compound (for example, a polymerizable compound), by performing a curing treatment on the composition, a cured film can be obtained.

The refractive index of the film is not particularly limited, but is preferably equal to or higher than 1.55, and more preferably 1.6 to 2.0.

The light transmittance of the film is not particularly limited. In the entire wavelength range of 400 to 700 nm, the light transmittance of the film is preferably equal to or higher than 90%, more preferably equal to or higher than 95%, and even more preferably 100%.

The thickness of the film is not particularly limited, but is preferably 0.1 to 20 μm, more preferably 0.1 to 10 μmm, and even more preferably 0.5 to 4 μm.

The method for curing the composition according to the embodiment of the present invention is not particularly limited, and examples thereof include heating, exposure, and the like. As devices used for heating, a blast dryer, an oven, an infrared dryer, a heating drum, and the like can be used without particular limitation. As devices used for exposure, a mercury lamp, a metal halide lamp, a xenon (Xe) lamp, a chemical lamp, a carbon arc lamp, and the like can be used without particular limitation.

(Manufacturing Method of Pattern-Type Cured Film)

Hereinafter, as one of the examples of the manufacturing method of a cured film, a method for manufacturing a pattern-type cured film will be specifically described.

The manufacturing method of a pattern-type cured film includes a step of forming a composition layer (coating film) by coating a substrate with the composition (hereinafter, simply referred to as "composition layer forming step" as appropriate), a step of exposing the composition layer through a mask (hereinafter, simply referred to as "exposure step" as appropriate), and a step of forming a pattern-type cured film by developing the exposed composition layer (hereinafter, simply referred to as "development step" as appropriate).

Generally, the composition used in the above manufacturing method contains a polymerizable compound and a photopolymerization initiator.

Specifically, by forming a composition layer by means of coating a substrate with the composition according to the embodiment of the present invention directly or through another layer (composition layer forming step), exposing the composition layer through a predetermined mask pattern such that only a portion of the composition layer irradiated with light is cured (exposure step), and developing the composition layer by using a developer (development step), a pattern-type cured film including pixels can be formed.

Hereinafter, each of the steps will be specifically described.

Composition Layer Forming Step

In the composition layer forming step, a composition layer (coating film) is formed by coating a substrate with the composition according to the embodiment of the present invention.

The substrate is not particularly limited, and examples thereof include alkali-free glass used in a liquid crystal display device and the like, soda-lime glass, Pyrex (registered trademark) glass, quartz glass, substrates obtained by attaching a transparent electrode film to these, a photoelectric conversion element substituent used in a solid-state imaging element and the like (for example, a silicon substrate and the like), a Charge Coupled Device (CCD) substrate, a Complementary Metal Oxide Semiconductor (CMOS) substrate, and the like.

As the method for coating a substrate with the composition according to the embodiment of the present invention, it is possible to use various coating methods such as slit coating, an ink jet method, spin coating, cast coating, roll coating, and a screen printing method.

The coating film thickness of the composition can be appropriately selected according to the use. For example, the coating film thickness is 0.1 to 20 μm, more preferably 0.1 to 10 μm, and even more preferably 0.5 to 4 μm.

Generally, the composition applied to a substrate is dried under the condition of 70° C. to 110° C. for about 2 to 4 minutes. In this way, the composition layer can be formed.

Exposure Step

In the exposure step, the composition layer (coating film) formed in the composition layer forming step is exposed through a mask such that only the portion of the coating film irradiated with light is cured.

It is preferable that the exposure is performed by the irradiation with actinic rays or radiation. Particularly, ultraviolet rays such as g-line, h-line, and i-line are more preferable. The irradiance is preferably 5 to 1,500 mJ/cm$^2$, and more preferably 10 to 1,000 mJ/cm$^2$.

Development Step

After the exposure step, an alkali development treatment (development step) is performed such that the portion not being irradiated with light in the exposure step is eluted into an aqueous alkaline solution. In this way, only the portion cured by light (the portion of the coating film irradiated with light) remains.

As a developer, an organic alkali developer which does not damage the circuit as the underlayer is desirable. Generally, the development temperature is 20° C. to 30° C., and the development time is 20 to 90 seconds.

Examples of the aqueous alkaline solution include an inorganic developer and an organic developer. Examples of the inorganic developer include an aqueous alkaline solution in which sodium hydroxide, potassium hydroxide, sodium carbonate, sodium hydrogen carbonate, sodium silicate, or sodium metasilicate is dissolved at a concentration of 0.001% to 10% by mass and preferably at a concentration of 0.01% to 1% by mass. Examples of the organic developer include an aqueous alkaline solution in which an alkaline compound such as aqueous ammonia, ethyl amine, diethyl amine, dimethylethanolamine, tetramethylammonium hydroxide (TMAH), tetraethylammonium hydroxide, choline, pyrrole, piperidine, or 1,8-diazabicyclo-[5.4.0]-7-undecene is dissolved at a concentration of 0.001% to 10% by mass and preferably at a concentration of 0.01% to 1% by mass. For example, an appropriate amount of water-soluble organic solvent such as methanol or ethanol and/or a surfactant can be added to the aqueous alkaline solution. In a case where a developer formed of such an aqueous alkaline solution is used, generally, the film is rinsed with pure water after development.

As the development method, for example, a puddle development method, a shower development method, and the like can be used.

<Lens>

The film (preferably the cured film) according to the embodiment of the present invention can also be used as a lens. Particularly, the lens can be suitably used in a microlens of the solid-state imaging element described above.

<Solid-State Imaging Element>

The film (preferably the cured film) according to the embodiment of the present invention can be suitably used in a solid-state imaging element.

The solid-state imaging element according to an embodiment of the present invention is constituted with, for example, a plurality of photodiodes and light receiving elements formed of polysilicon or the like constituting a light-receiving area of a solid-state imaging element (a CCD image sensor, a CMOS image sensor, and the like), and an undercoat film as the film according to the embodiment of the present invention under a color filter that are provided on a substrate.

EXAMPLES

Hereinafter, the present invention will be more specifically described based on examples. The materials, the amounts of the materials used, the proportion of the materials, the contents of treatments, the procedure of treatments, and the like shown in the following examples can be appropriately changed as long as the gist of the present invention is maintained. Accordingly, the scope of the present invention is not limited to the following examples.

[1] Synthesis of Compound Represented by General Formula (I)

(Synthesis Example 1) Synthesis of Compound (A-1)

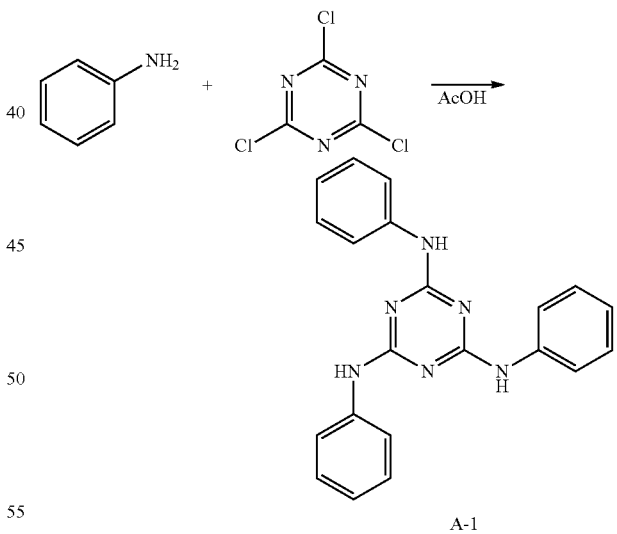

Cyanuric acid chloride (10.0 g) and 192 g of acetic acid were put into a three-neck flask and stirred under a nitrogen stream. Aniline (16.7 g) was added dropwise to the solution, and the solution was stirred for 2 hours while being heated at an external temperature of 110° C. Then, the obtained solution was cooled to 50° C., and 192 g of water was added thereto. The obtained solution was ice-cooled and stirred for 1 hour at an internal temperature of 0° C. to 5° C., and then the precipitated solids were collected by filtration, and the materials obtained by filtration were rinsed with 100 g of water. By using a vacuum dryer, the materials obtained by filtration were dried for 24 hours at 60° C., thereby obtaining 17.1 g of a compound (A-1).

(Synthesis Examples 2 to 8) Synthesis of Compounds (A-2) to (A-9)

Compounds (A-2) to (A-9) were synthesized by performing the same operation as in Synthesis Example 1, except that aniline (an amino compound) as a raw material was changed to amino compounds corresponding to the compounds (A-2) to (A-9).

The compound (A-1) and compounds (A-2) to (A-9) will be shown below. "Ac" represents an acetyl group, and "Me" represents a methyl group.

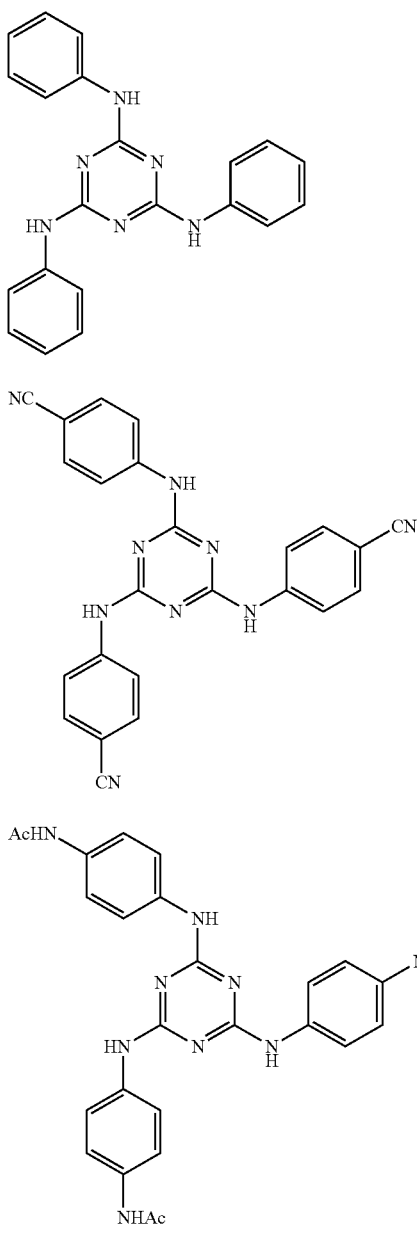

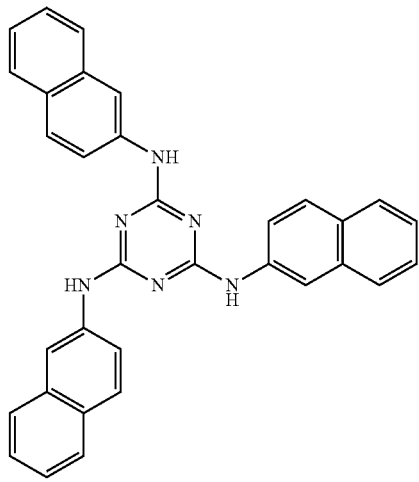

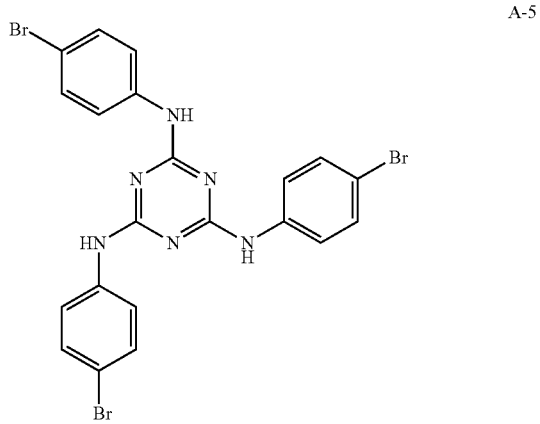

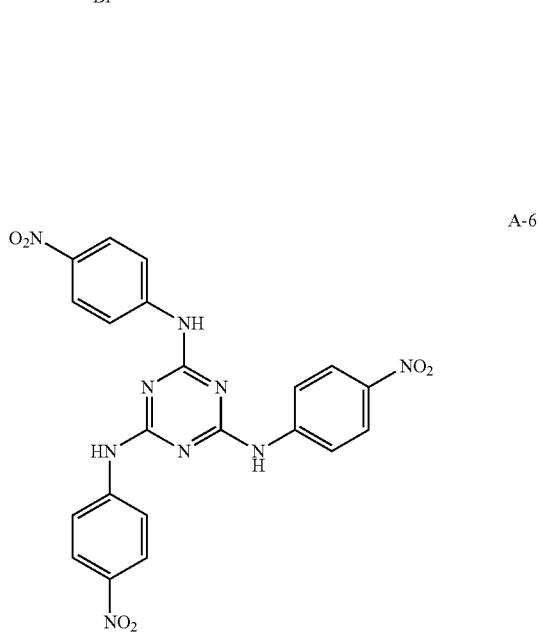

-continued

A-7
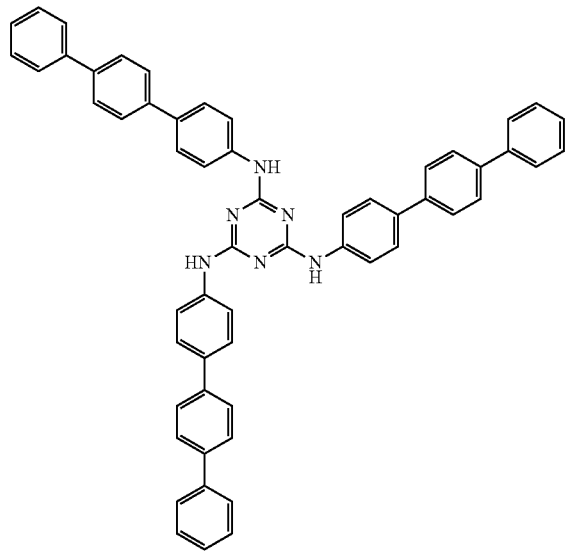

A-8
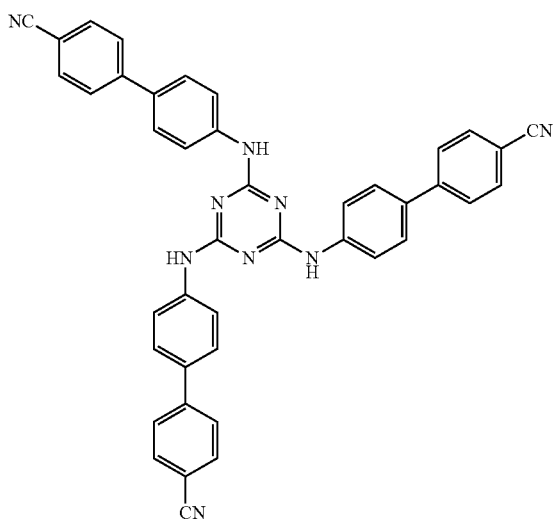

A-9
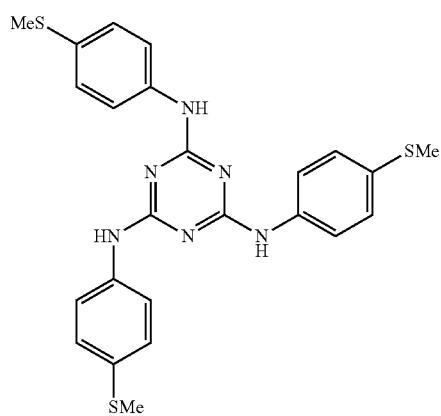

(Synthesis Example 10) Synthesis of Compound (A-10)

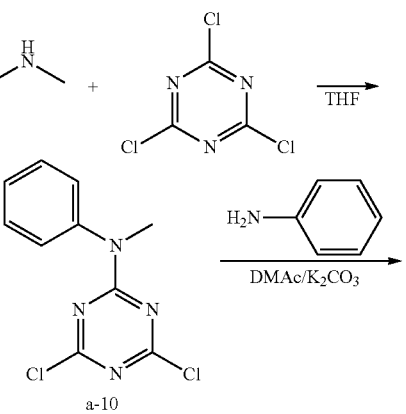

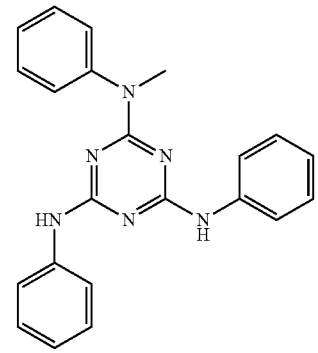

A-10

Cyanuric acid chloride (5.0 g) and 50 g of tetrahydrofuran were put into a three-neck flask. Then, the three-neck flask was cooled in an ice bath obtained by adding ice to methanol, and in this state, the solution in the three-neck flask was stirred under a nitrogen stream. A solution, which was prepared by dissolving 3.2 g of N-methylaniline in 32.3 g of tetrahydrofuran, was added dropwise to the aforementioned solution for 1.5 hours, and the obtained solution was further stirred for 2 hours. Water (100 g) was put into the three-neck flask, the solution in the flask was stirred for 1 hour at an internal temperature of 0° C. to 5° C., then the precipitated solids were collected by filtration, and the materials obtained by filtration were rinsed with 100 g of water. By using a vacuum dryer, the materials obtained by filtration were dried for 24 hours at 60° C., thereby obtaining 12.1 g of an intermediate (a-10).

The intermediate (a-10) (11.0 g), 10.5 g of aniline, 5.0 g of potassium carbonate, and 100 mL of N,N-dimethylacetamide were put into a three-neck flask and stirred for 2 hours while being heated at an external temperature of 110° C. under a nitrogen stream. Thereafter, the obtained solution was cooled to an internal temperature of 5° C., and 250 g of 1N hydrochloric acid was added dropwise to the three-neck flask. The three-neck flask was ice-cooled, the solution in the flask was stirred for 1 hour at an internal temperature of 0° C. to 5° C., the precipitated solids were collected by filtration, and the materials obtained by filtration were rinsed with 100 g of water. The materials obtained by filtration were dried for 24 hours at 60° C. by using a vacuum dryer, thereby obtaining 10.0 g of a compound (A-10).

(Synthesis Examples 11 to 13) Synthesis of Compounds (A-11) to (A-13)

Compounds (A-11) to (A-13) were obtained by performing the same operation as in Synthesis Example 10, except that N-methylaniline in Synthesis Example 10 was changed to phenol, thiophenol, or 2-aminobenzimidazole.

The compound (A-10) and compounds (A-11) to (A-13) will be shown below.

A-10

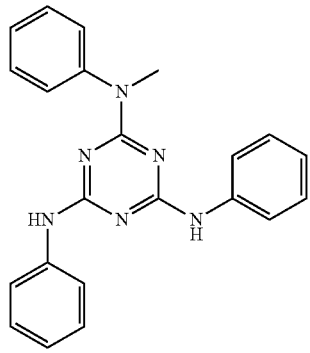

A-11

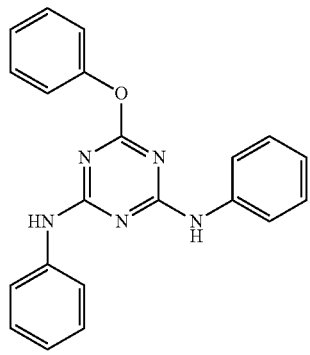

A-12

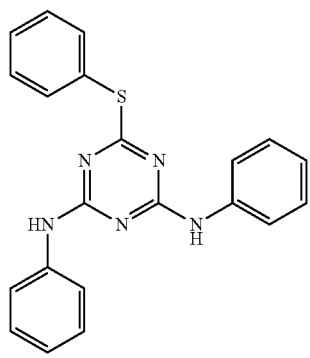

A-13

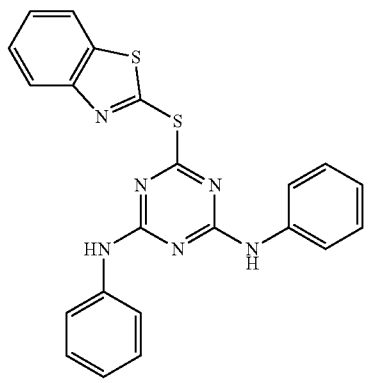

(Synthesis Example 14) Synthesis of Compound (A-14)

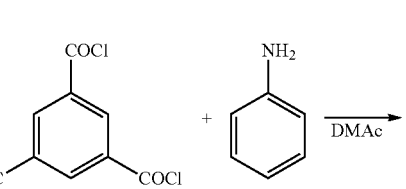

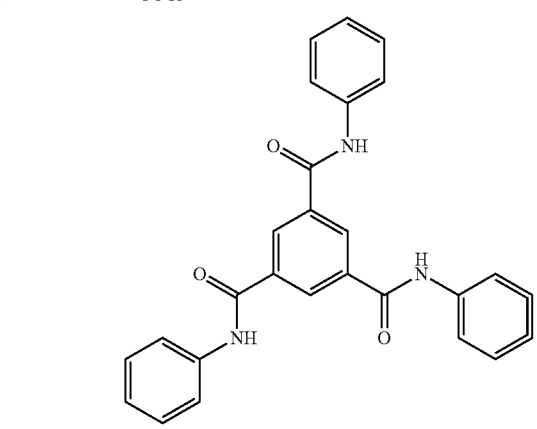

A-14

Trimellitic acid chloride (10.0 g) and 100 mL of N,N-dimethylacetamide were put into a three-neck flask, and the flask was ice-cooled under a nitrogen stream. Then, 21.0 g of aniline was slowly added dropwise to the three-neck flask, and the flask was kept at an internal temperature equal to or lower than 10° C. After aniline was completely added dropwise to the flask, the internal temperature of the flask was increased to 25° C., and the solution in the flask was stirred for 2 hours. Thereafter, 250 g of 1N hydrochloric acid was added dropwise to the three-neck flask. The flask was ice-cooled, the solution in the flask was stirred for 1 hour at an internal temperature of 0° C. to 5° C., the precipitated solids were collected by filtration, and the materials obtained by filtration were rinsed with 100 g of water. The materials obtained by filtration were dried for 24 hours at 60° C. by using a vacuum dryer, thereby obtaining 12.3 g of a compound (A-14).

(Synthesis Examples 15 to 17) Synthesis of Compounds (A-15) to (A-17)

Compounds (A-15) to (A-17) were obtained by performing the same operation as Synthesis Example 14, except that either or both of the acid chloride and aniline (an amino compound) in Synthesis Example 14 were changed to either or both of the acid chloride and amino compound corresponding to the compounds (A-15) to (A-17).

The compound (A-14) and the compounds (A-15) to (A-17) will be shown below.

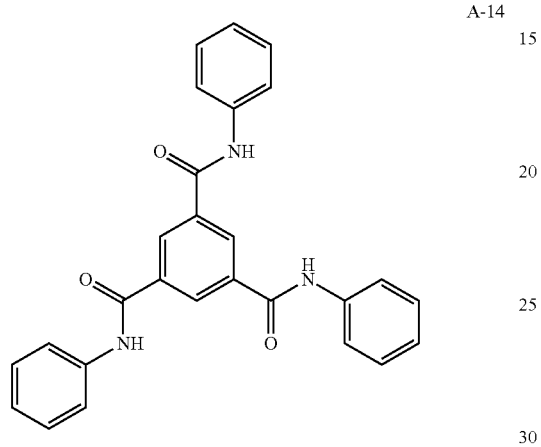

A-14

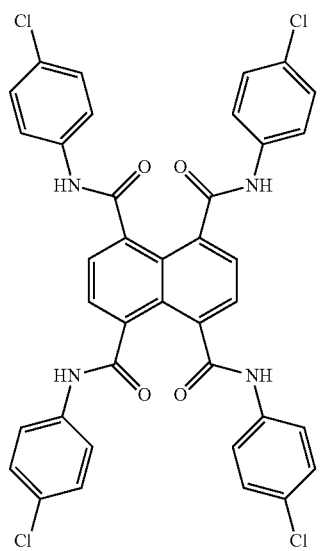

A-16

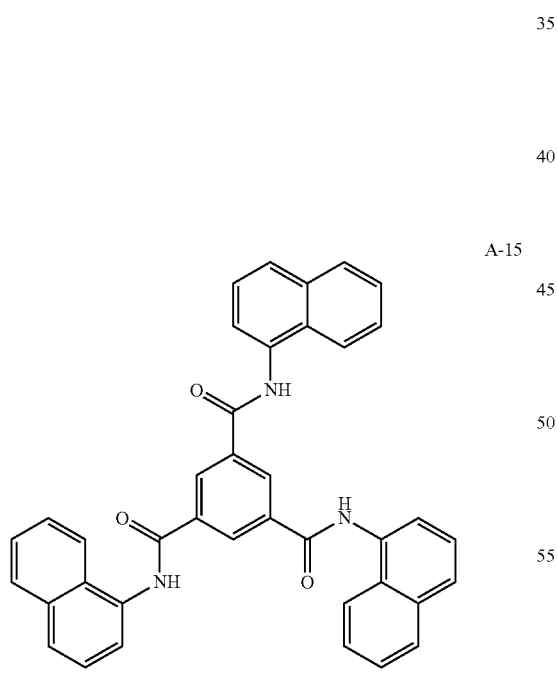

A-15

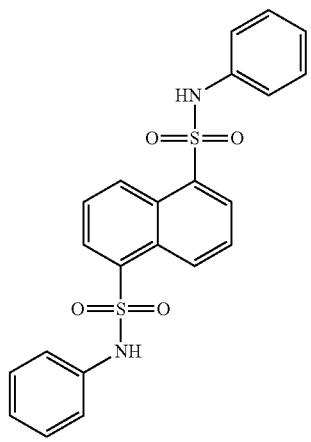

A-17

(Synthesis Example 18) Synthesis of Compound (A-18)

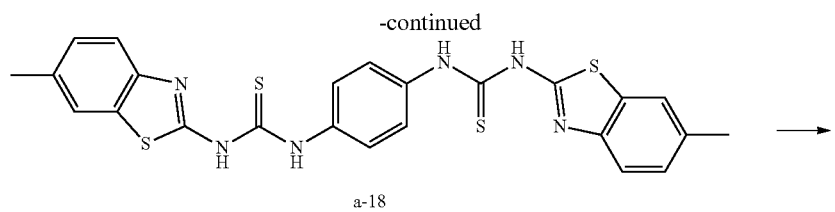

a-18

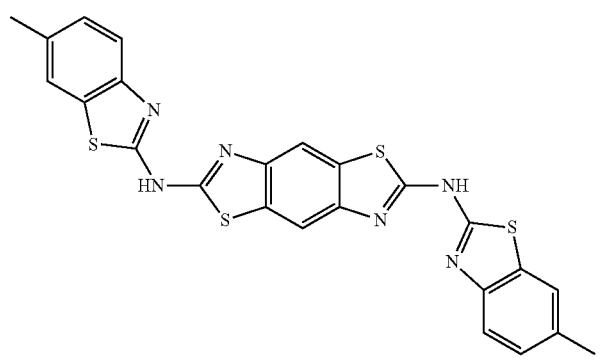

A-18

2-Amino-6-methyl benzothiazole (33 g), 0.5 g of 4-dimethylaminopyridine, and 177 g of N,N-dimethylformamide were put into a three-neck flask. Then, 17 g of 1,4-phenylenediisothiocyanate was put into the three-neck flask, and the solution in the flask was stirred for 1 hour and then heated for 2 hours at an external temperature of 105° C. Thereafter, the solution was cooled to 50° C., and 100 mL of 1N hydrochloric acid was put into the three-neck flask. The flask was ice-cooled, the solution in the flask was stirred for 1 hour at an internal temperature of 0° C. to 5° C., the precipitated solids were then collected by filtration, and the materials obtained by filtration were rinsed with 500 g of water. By using a vacuum dryer, the materials obtained by filtration were dried for 24 hours at 60° C., thereby obtaining 10.7 g of an intermediate (a-18).

The intermediate (a-18) (10 g) and 80 g of N-methylpyrrolidone were put into a three-neck flask and stirred. Tetrabutylammonium bromide (20 g) was slowly added thereto in divided portions. The precipitated solids were filtered and washed with 100 mL of acetone, 100 mL of 5% by mass aqueous sodium bicarbonate, and 100 mL of water in this order. By using a vacuum dryer, the materials obtained by filtration were dried for 24 hours at 60° C., thereby obtaining 8.7 g of a compound (A-18).

(Synthesis Examples 19 and 20) Synthesis of Compounds (A-19) and (A-20)

Based on the synthesis method for the compound (A-10), compounds (A-19) and (A-20) were synthesized.

The compounds (A-19) and (A-20) will be shown below.

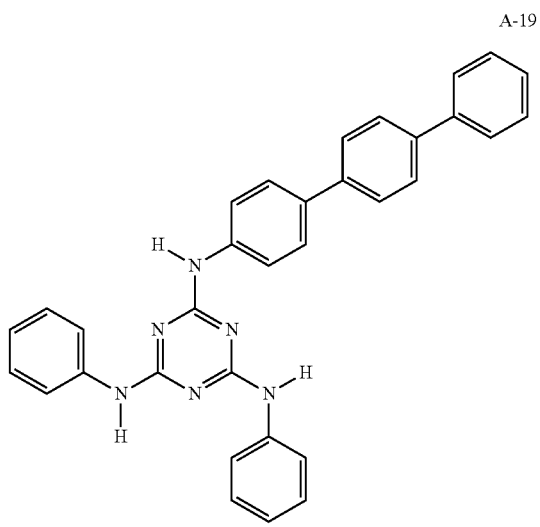

A-19

A-20
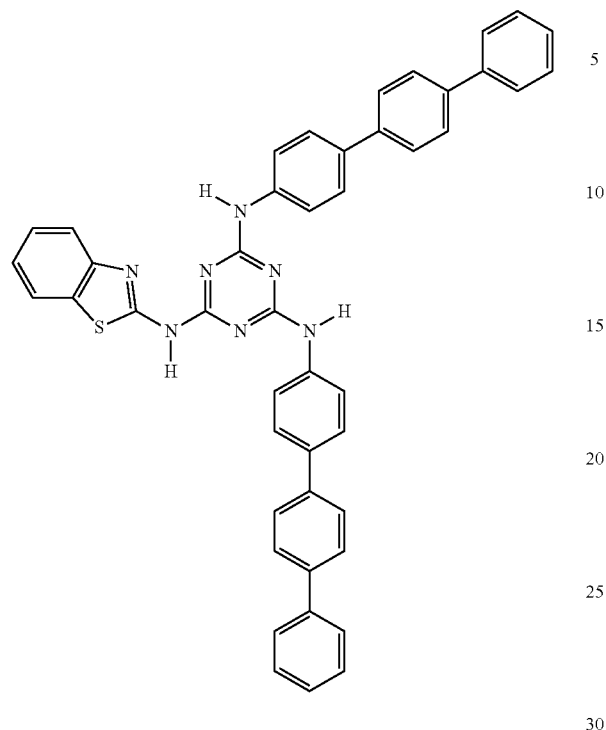
(Synthesis Examples 21 and 22) Synthesis of Compounds (A-21) and (A-22)
Based on the synthesis method for the compound (A-1), compounds (A-21) and (A-22) were synthesized.
The compounds (A-21) and (A-22) will be shown below.
A-21
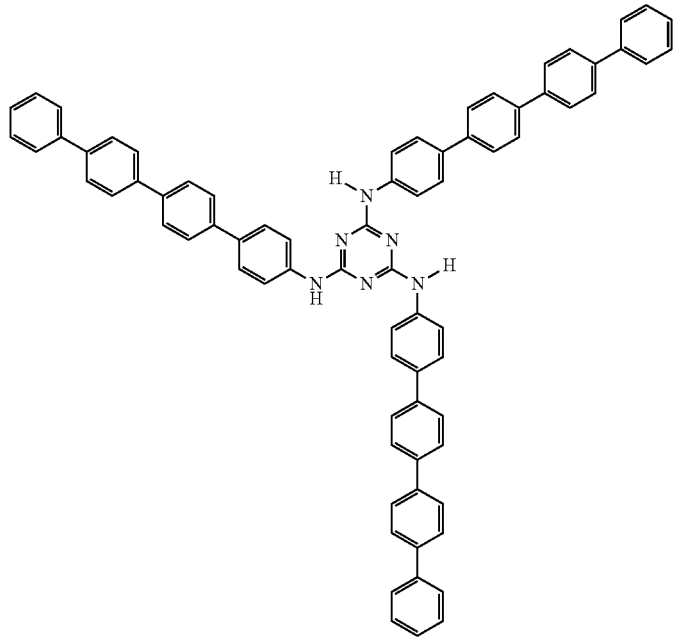

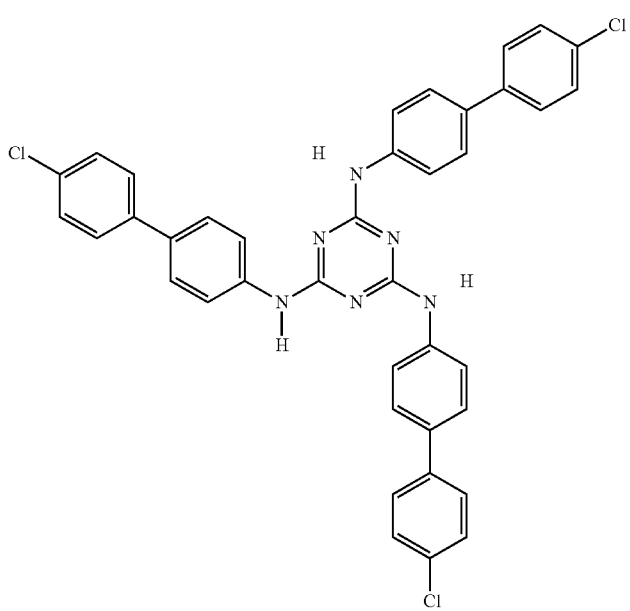

A-22

(Synthesis Examples 23 and 24) Synthesis of Compounds (A-23) and (A-24)

Based on the synthesis method for the compound (A-10), compounds (A-23) and (A-24) were synthesized.

The compounds (A-23) and (A-24) will be shown below.

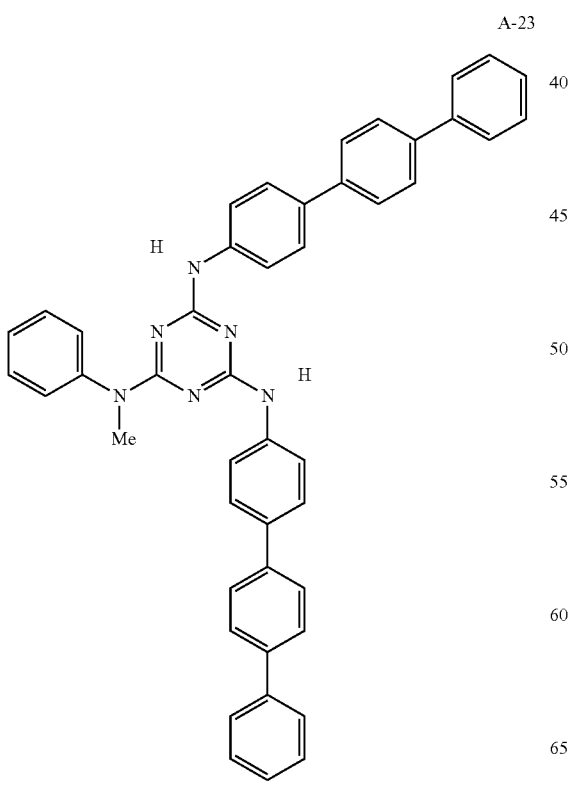

A-23

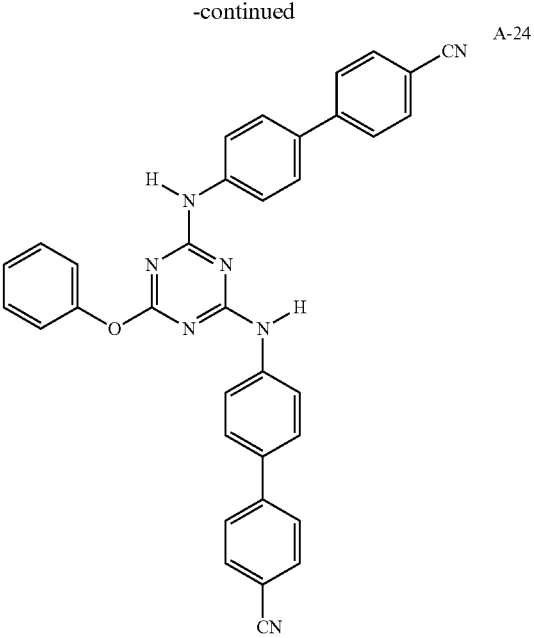

A-24

Each of the compound (A-7), the compound (A-8), and the compounds (A-19) to (A-24) was identified by measuring a Mass Spectrum (MS).

Specifically, a sample was dissolved (suspended) in dimethyl sulfoxide and mixed with a dimethyl sulfoxide solution containing α-cyano-4-hydroxycinnamic acid (CHCA) matrix, a Matrix Assisted Laser Desorption/Ionization (MALDI) plate was coated with the obtained mixture, and a mass spectrum was measured. The mass spectrum was measured using autoflex manufactured by Bruker in a positive mode. The results will be shown below.

Compound (A-7) detected M$^+$+1 (posi): 811
Compound (A-8) detected M$^+$+1 (posi): 658
Compound (A-19) detected M$^+$+1 (posi): 504

Compound (A-20) detected M$^+$+1 (posi): 713
Compound (A-21) detected M$^+$+1 (posi): 1036
Compound (A-22) detected M$^+$+1 (posi): 682
Compound (A-23) detected M$^+$+1 (posi): 670
Compound (A-24) detected M$^+$+1 (posi): 555

Furthermore, the obtained compound (A-18) was also identified by MS measurement.

Specifically, a sample was dissolved (suspended) in acetone and mixed with a CHCA matrix solution (acetone), and a MALDI plate was coated with the obtained mixture. MS was measured using autoflex from Bruker in a positive mode.

Compound (A-18) detected M$^+$+1 (posi): 571.10

[2] Dissolution Test (Dissolution Test 1)

By the following method, the solubility of the compound represented by General Formula (I) in a solvent was investigated.

The compound represented by General Formula (I) (compound (A-1), 1 g) was added to 50 g of a solvent (PGMEA) shown in Table 1, and the obtained solution was stirred for 1 hour at 25° C. Then, solids were removed using a 0.5 μm TEFLON (registered trademark) filter. Thereafter, the obtained filtrate was caused to volatilize for 3 hours at 150° C. in a vacuum, and the content of residues was measured, thereby quantifying the content of solids dissolved in the solvent.

As a result, the solubility of the compound (A-1) in the solvent PGMEA was found to be less than 0.5% by mass.

(Dissolution Tests 2 to 54)

Dissolution tests 2 to 54 were carried out by performing the same operation as in the dissolution test 1, except that the compound represented by General Formula (I) and the solvent were changed to those described in Table 1.

As a result, the solubility of the compounds (A-1) to (A-24) in the solvents shown in Table 1 was found to be less than 0.5% by mass.

Table 1 shows the results of the dissolution tests 1 to 54.

In Table 1, "PGMEA" means propylene glycol monomethyl ether acetate, and "PGME" means propylene glycol monomethyl ether.

TABLE 1

|  | Compound represented by General Formula (I) | Solvent | Solubility |
|---|---|---|---|
| Dissolution test 1 | A-1 | PGMEA | Less than 0.5% by mass |
| Dissolution test 2 | A-2 | PGMEA | Less than 0.5% by mass |
| Dissolution test 3 | A-3 | PGMEA | Less than 0.5% by mass |
| Dissolution test 4 | A-4 | PGMEA | Less than 0.5% by mass |
| Dissolution test 5 | A-5 | PGMEA | Less than 0.5% by mass |
| Dissolution test 6 | A-6 | PGMEA | Less than 0.5% by mass |
| Dissolution test 7 | A-7 | PGMEA | Less than 0.5% by mass |
| Dissolution test 8 | A-8 | PGMEA | Less than 0.5% by mass |
| Dissolution test 9 | A-9 | PGMEA | Less than 0.5% by mass |
| Dissolution test 10 | A-10 | PGMEA | Less than 0.5% by mass |
| Dissolution test 11 | A-11 | PGMEA | Less than 0.5% by mass |
| Dissolution test 12 | A-12 | PGMEA | Less than 0.5% by mass |
| Dissolution test 13 | A-13 | PGMEA | Less than 0.5% by mass |
| Dissolution test 14 | A-14 | PGMEA | Less than 0.5% by mass |
| Dissolution test 15 | A-15 | PGMEA | Less than 0.5% by mass |
| Dissolution test 16 | A-16 | PGMEA | Less than 0.5% by mass |
| Dissolution test 17 | A-17 | PGMEA | Less than 0.5% by mass |
| Dissolution test 18 | A-18 | PGMEA | Less than 0.5% by mass |

TABLE 2

Continued from Table 1

|  | Compound represented by General Formula (I) | Solvent | Solubility |
|---|---|---|---|
| Dissolution test 19 | A-1 | Toluene | Less than 0.5% by mass |
| Dissolution test 20 | A-2 | Cyclohexyl methyl ether | Less than 0.5% by mass |
| Dissolution test 21 | A-3 | PGME | Less than 0.5% by mass |
| Dissolution test 22 | A-4 | Butyl acetate | Less than 0.5% by mass |
| Dissolution test 23 | A-5 | 3-methoxybutyl acetate | Less than 0.5% by mass |
| Dissolution test 24 | A-6 | Cyclohexyl acetate | Less than 0.5% by mass |
| Dissolution test 25 | A-7 | PGMEA/PGME (90% by mass/10% by mass) | Less than 0.5% by mass |
| Dissolution test 26 | A-8 | Cyclopentanone | Less than 0.5% by mass |
| Dissolution test 27 | A-9 | Cyclobutyl ether | Less than 0.5% by mass |
| Dissolution test 28 | A-10 | Propylene glycol diacetate | Less than 0.5% by mass |
| Dissolution test 29 | A-11 | Dipropylene glycol dimethyl ether | Less than 0.5% by mass |
| Dissolution test 30 | A-12 | Diethylene glycol monobutyl ether acetate | Less than 0.5% by mass |
| Dissolution test 31 | A-13 | Xylene | Less than 0.5% by mass |
| Dissolution test 32 | A-14 | Ethyl lactate | Less than 0.5% by mass |
| Dissolution test 33 | A-15 | PGMEA/PGME (90% by mass/10% by mass) | Less than 0.5% by mass |
| Dissolution test 34 | A-16 | PGMEA/PGME (80% by mass/20% by mass) | Less than 0.5% by mass |
| Dissolution test 35 | A-17 | Cyclopentanone/PGME (90% by mass/10% by mass) | Less than 0.5% by mass |
| Dissolution test 36 | A-18 | PGMEA/butyl acetate (70% by mass/30% by mass) | Less than 0.5% by mass |

TABLE 2-continued

Continued from Table 1

| | Compound represented by General Formula (I) | Solvent | Solubility |
|---|---|---|---|
| Dissolution test 37 | A-3 | Cyclohexanone | Less than 0.5% by mass |
| Dissolution test 38 | A-4 | PGME | Less than 0.5% by mass |
| Dissolution test 39 | A-7 | PGMEA/PGME (70% by mass/30% by mass) | Less than 0.5% by mass |
| Dissolution test 40 | A-9 | Diethylene glycol monobutyl ether acetate | Less than 0.5% by mass |
| Dissolution test 41 | A-10 | Anisole | Less than 0.5% by mass |
| Dissolution test 42 | A-12 | 3-Methoxybutyl acetate | Less than 0.5% by mass |
| Dissolution test 43 | A-13 | Propylene glycol diacetate | Less than 0.5% by mass |
| Dissolution test 44 | A-15 | Cyclohexyl acetate | Less than 0.5% by mass |
| Dissolution test 45 | A-16 | 3-Methoxybutyl acetate | Less than 0.5% by mass |
| Dissolution test 46 | A-18 | Dipropylene glycol dimethyl ether | Less than 0.5% by mass |
| Dissolution test 47 | A-7 | PGMEA/PGME (70% by mass/30% by mass) | Less than 0.5% by mass |
| Dissolution test 48 | A-10 | Anisole | Less than 0.5% by mass |

TABLE 3

Continued from Table 1

| | Compound represented by General Formula (I) | Solvent | Solubility |
|---|---|---|---|
| Dissolution test 49 | A-19 | PGMEA | Less than 0.5% by mass |
| Dissolution test 50 | A-20 | PGMEA | Less than 0.5% by mass |
| Dissolution test 51 | A-21 | PGMEA | Less than 0.5% by mass |
| Dissolution test 52 | A-22 | PGMEA | Less than 0.5% by mass |
| Dissolution test 53 | A-23 | PGMEA | Less than 0.5% by mass |
| Dissolution test 54 | A-24 | PGMEA | Less than 0.5% by mass |

[3] Preparation of Dispersion Liquid (Dispersion Composition)

A solution obtained by mixing together the following components was mixed and dispersed for 3 hours by using a beads mill (zirconia beads having a diameter of 0.3 mm), thereby preparing a dispersion liquid (dispersion composition). Table 4 shows the maximum absorption wavelength of the compound represented by General Formula (I) in a wavelength range of 300 to 800 nm. The method for measuring the maximum absorption wavelength will be described later as "spectral characteristics".

Components

| | |
|---|---|
| Compound represented by General Formula (I) shown in Table 2 (any of compounds (A-1) to (A-24)) | 20 parts by mass |
| Dispersant shown in Table 2 (any of resins 1 to 3) | 5 parts by mass |
| Solvent shown in Table 2 | 80 parts by mass |

The structures of the dispersants (resins 1 to 3) will be shown below.

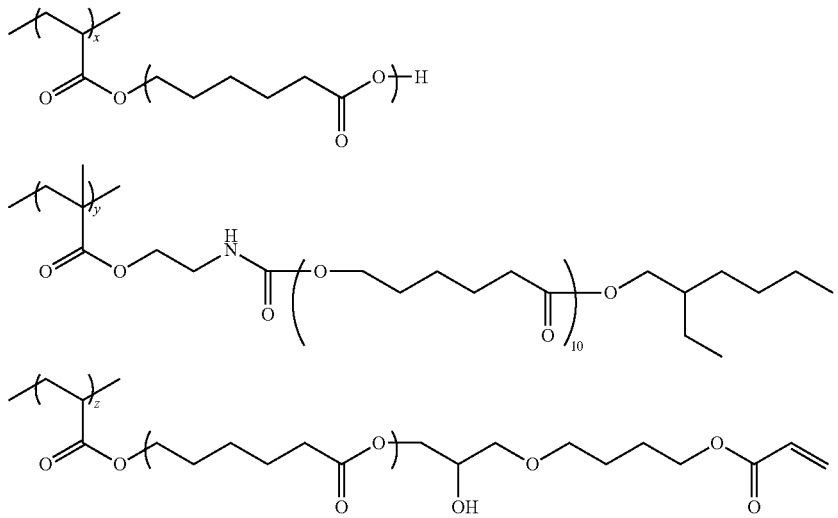

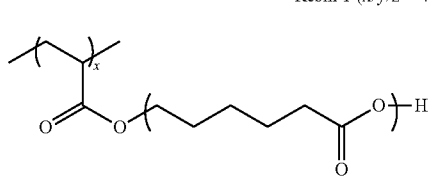

Resin 1 (x/y/z = 40/50/10 (wt %)) Mw 20,000

-continued

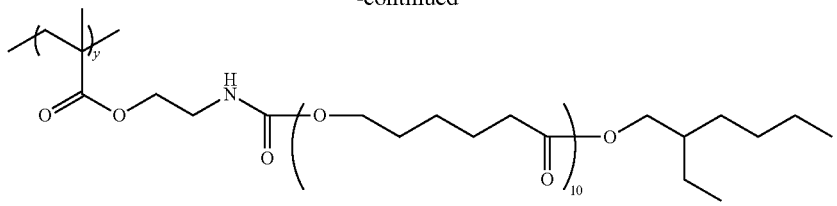

Resin 2 (x/y = 40/60 (wt %)) Mw 18,000

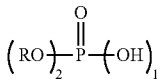

Resin 3 Mw 7,000

R =

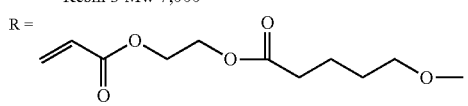

TABLE 4

Table 2

Makeup of dispersion liquid

| | Compound represented by General Formula (I) | Solvent | Dispersed resin |
|---|---|---|---|
| Dispersion liquid 1 | A-1 | Toluene | Resin 1 |
| Dispersion liquid 2 | A-2 | PGMEA | Resin 1 |
| Dispersion liquid 3 | A-3 | Cyclohexanone | Resin 1 |
| Dispersion liquid 4 | A-4 | PGME | Resin 1 |
| Dispersion liquid 5 | A-5 | 3-Methoxybutyl acetate | Resin 1 |
| Dispersion liquid 6 | A-6 | Cyclohexyl acetate | Resin 1 |
| Dispersion liquid 7 | A-7 | PGMEA/PGME (70/30: mass ratio) | Resin 1 |
| Dispersion liquid 8 | A-8 | Cyclopentanone | Resin 1/Resin 3 (80/20: mass ratio) |
| Dispersion liquid 9 | A-9 | Diethylene glycol monobutyl ether acetate | Resin 1 |
| Dispersion liquid 10 | A-10 | Anisole | Resin 1 |
| Dispersion liquid 11 | A-11 | PGMEA | Resin 1 |
| Dispersion liquid 12 | A-12 | 3-Methoxybutyl acetate | Resin 1 |
| Dispersion liquid 13 | A-13 | Propylene glycol diacetate | Resin 1 |
| Dispersion liquid 14 | A-14 | PGMEA | Resin 1 |
| Dispersion liquid 15 | A-15 | Cyclohexyl acetate | Resin 1 |
| Dispersion liquid 16 | A-16 | 3-Methoxybutyl acetate | Resin 1 |
| Dispersion liquid 17 | A-17 | PGMEA | Resin 1 |
| Dispersion liquid 18 | A-18 | Dipropylene glycol dimethyl ether | Resin 1 |
| Dispersion liquid 19 | A-2/A-8 = 50/50 (mass ratio) | PGMEA | Resin 1 |
| Dispersion liquid 20 | A-2 | PGMEA | Resin 2 |
| Dispersion liquid 21 | A-7 | PGMEA/PGME (70/30: mass ratio) | Resin 2 |
| Dispersion liquid 22 | A-10 | Anisole | Resin 2 |
| Dispersion liquid 23 | A-19 | PGMEA | Resin 1 |
| Dispersion liquid 24 | A-20 | PGMEA | Resin 1 |
| Dispersion liquid 25 | A-21 | PGMEA | Resin 1 |
| Dispersion liquid 26 | A-22 | PGMEA | Resin 1 |
| Dispersion liquid 27 | A-23 | PGMEA | Resin 1 |
| Dispersion liquid 28 | A-24 | PGMEA | Resin 1 |

[4] Preparation of Composition (Curable Composition) (Examples 1 to 31)

Compositions (curable compositions) were prepared by mixing together the following components. The prepared compositions 1 to 31 were named Examples 1 to 31 respectively and evaluated as will be described later.

Components

Dispersion liquid shown in Table 3 (any of dispersion liquids 1 to 28) 100 parts by mass Polymerizable compound shown in Table 3 mixing amount shown in Table 3 (part by mass)

Binder shown in Table 3 mixing amount shown in Table 3 (part by mass)

Photopolymerization initiator shown in Table 3 mixing amount shown in Table 3 (part by mass)

Surfactant MEGAFACE R-40 (DIC Corporation) shown in Table 3 0.1 parts by mass

The structure of each of the polymerizable compounds (M-1 to M-6), the binders (J-1 to J-3), and the photopolymerization initiators (I-1 to I-10) will be shown below. x, y, z, and w shown in the binder J-2 mean mass ratio.

M-1
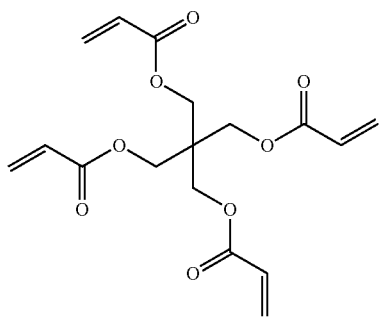
M-2
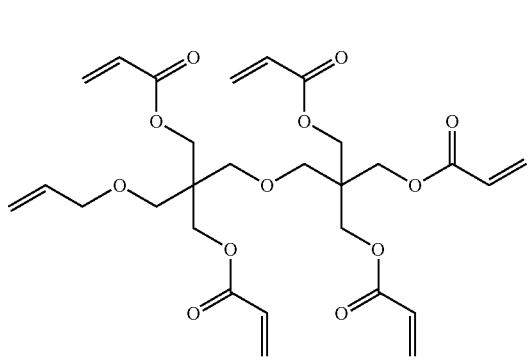
M-3
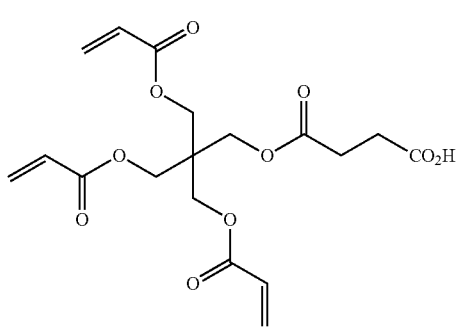
M-4
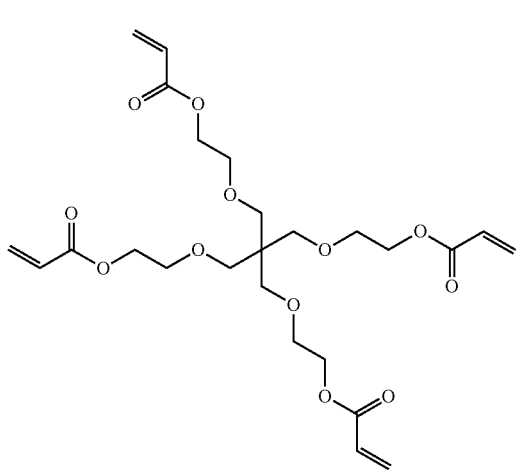
M-5
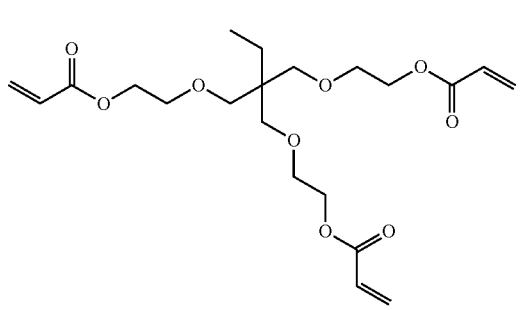
M-6
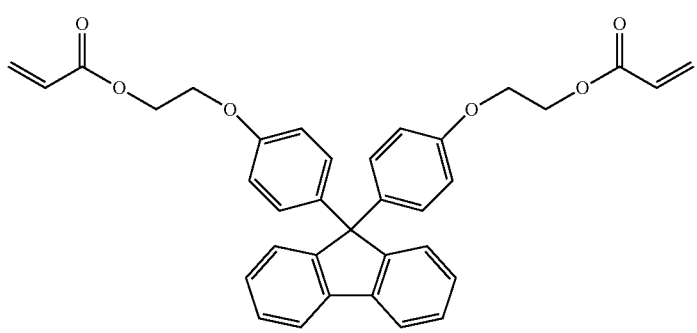

-continued
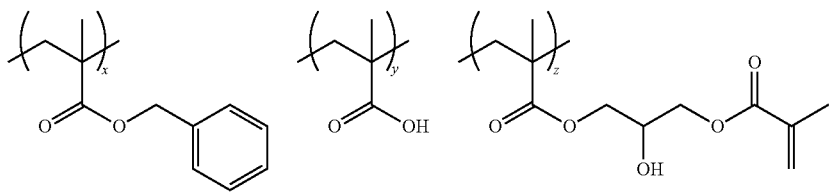
J-1
x/y/z = 50/10/40 (Mass ratio)
Mw 15,000
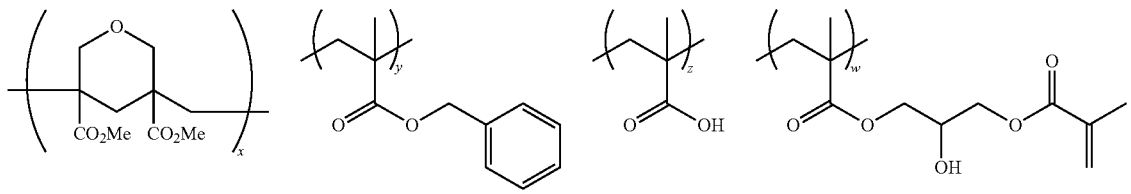
J-2
x/y/z/w = 10/40/10/40
Mw 12,000
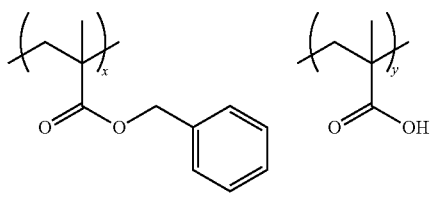
J-3
x/y = 60/40 (Mass ratio)
Mw 17,000
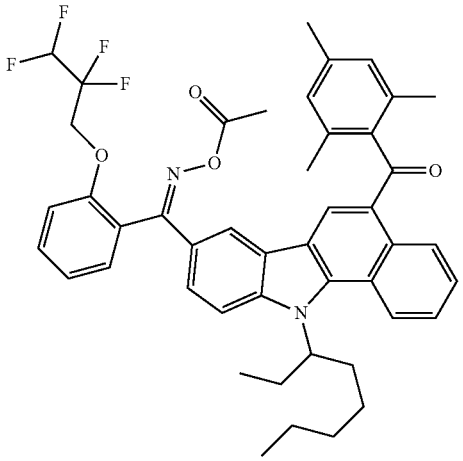
I-1
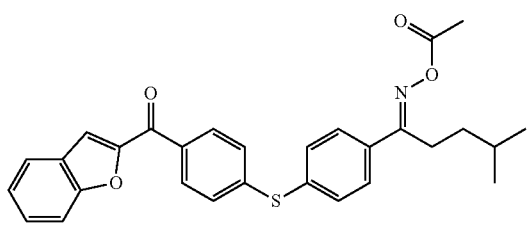
I-2
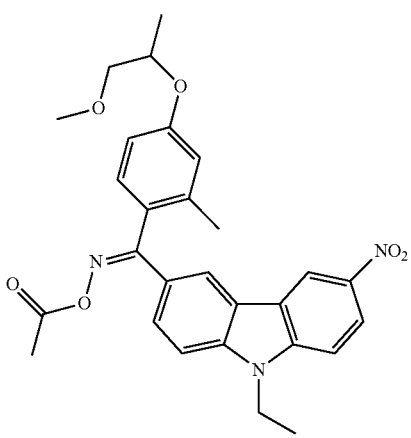
I-3

-continued

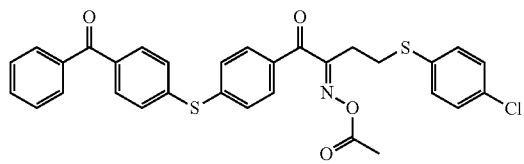 I-4

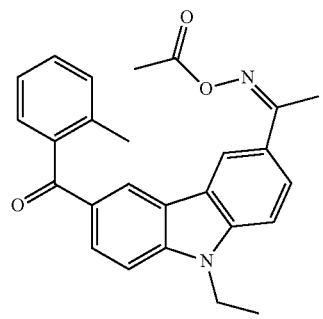 I-5

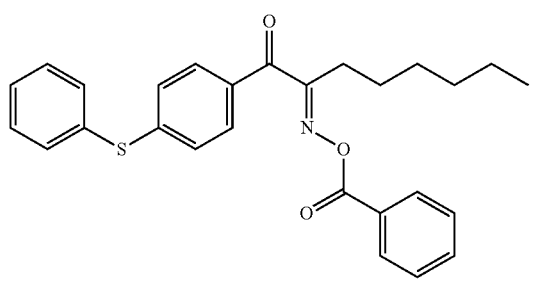 I-6

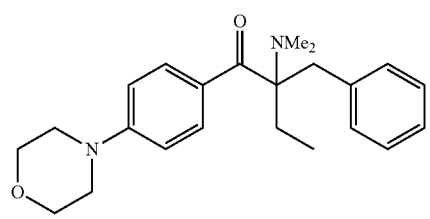 I-7

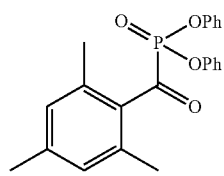 I-8

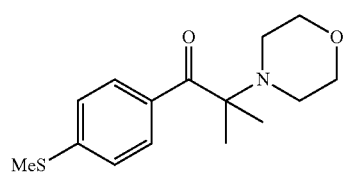 I-9

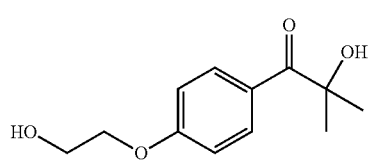 I-10

TABLE 5

| | | Makeup of composition (curable composition) | | | | | |
|---|---|---|---|---|---|---|---|
| | | Polymerizable compound | | Binder | | Photopolymerization initiator | |
| Table 3 | Dispersion liquid | Type | Added amount | Type | Added amount | Type | Added amount |
| Composition 1 | Dispersion liquid 1 | M-1 | 2 | J-1 | 1 | I-1 | 1 |
| Composition 2 | Dispersion liquid 2 | M-1 | 2 | J-1 | 1 | I-2 | 1 |
| Composition 3 | Dispersion liquid 3 | M-3 | 1 | J-2 | 2 | I-3 | 1 |
| Composition 4 | Dispersion liquid 4 | M-4 | 2 | J-2 | 1 | I-1/I-4 | 0.5/0.5 |
| Composition 5 | Dispersion liquid 5 | M-5 | 2 | J-2 | 1 | I-1 | 1 |
| Composition 6 | Dispersion liquid 6 | M-1 | 2 | J-1 | 1 | I-2 | 1 |
| Composition 7 | Dispersion liquid 7 | M-1/M-3 | 1/1 | J-2 | 1 | I-3 | 1 |
| Composition 8 | Dispersion liquid 8 | M-2 | 2 | J-2 | 1 | I-4 | I |
| Composition 9 | Dispersion liquid 9 | M-4 | 1 | J-1/J-2 | 1/1 | I-2 | 1 |
| Composition 10 | Dispersion liquid 10 | M-5 | 2 | J-1 | 1 | I-7 | 1 |
| Composition 11 | Dispersion liquid 11 | M-1 | 2 | J-2 | 1 | I-8 | 1 |

TABLE 5-continued

| | | Polymerizable compound | | Binder | | Photopolymerization initiator | |
|---|---|---|---|---|---|---|---|
| Table 3 | Dispersion liquid | Type | Added amount | Type | Added amount | Type | Added amount |
| Composition 12 | Dispersion liquid 12 | M-2 | 2 | J-1 | 1 | I-9 | 1 |
| Composition 13 | Dispersion liquid 13 | M-1 | 2 | J-1 | 1 | I-1 | 1 |
| Composition 14 | Dispersion liquid 14 | M-2 | 2 | J-1 | 1 | I-9 | 1 |
| Composition 15 | Dispersion liquid 15 | M-5 | 1 | J-2 | 2 | I-8 | 1 |
| Composition 16 | Dispersion liquid 16 | M-6 | 2 | J-2 | 1 | I-10 | 1 |
| Composition 17 | Dispersion liquid 17 | M-3 | 2 | J-1 | 1 | I-10 | 1 |
| Composition 18 | Dispersion liquid 18 | M-2 | 2 | J-2 | 1 | I-2 | 1 |
| Composition 19 | Dispersion liquid 19 | M-6 | 1 | J-1 | 2 | I-5 | 1 |
| Composition 20 | Dispersion liquid 20 | M-1 | 1 | J-2 | 2 | I-7 | 1 |
| Composition 21 | Dispersion liquid 21 | M-2 | 2 | J-1 | 1 | I-9 | 1 |
| Composition 22 | Dispersion liquid 22 | M-4 | 2 | J-2 | 1 | I-8 | 1 |
| Composition 23 | Dispersion liquid 1 | M-1 | 1 | J-2 | 1 | I-7 | 1 |
| Composition 24 | Dispersion liquid 1 | M-2 | 1 | J-3 | 1 | I-6 | 1 |
| Composition 25 | Dispersion liquid 1 | M-4 | 1 | J-3 | 1 | I-8 | 1 |
| Composition 26 | Dispersion liquid 23 | M-1 | 2 | J-1 | 1 | I-1 | 1 |
| Composition 27 | Dispersion liquid 24 | M-1 | 2 | J-1 | 1 | I-1 | 1 |
| Composition 28 | Dispersion liquid 25 | M-1 | 2 | J-1 | I | I-1 | 1 |
| Composition 29 | Dispersion liquid 26 | M-I | 2 | J-1 | 1 | I-1 | 1 |
| Composition 30 | Dispersion liquid 27 | M-1 | 2 | J-1 | 1 | I-1 | 1 |
| Composition 31 | Dispersion liquid 28 | M-1 | 2 | J-1 | 1 | I-1 | 1 |

[5] Evaluation of Composition

Each of the obtained compositions 1 to 31 was evaluated in terms of spectral characteristics, refractive index, exterior characteristics (dispersibility), moisture resistance, light fastness, developability, and pattern shape.

<Evaluation of Spectral Characteristics>

Each of the dispersion liquids 1 to 28 was diluted 1,000× with the solvent used for dispersion. By using Carry 5000 (manufactured by Agilent Technologies, Inc.), spectrometry was performed on the obtained solution at 300 to 800 nm. As references, samples containing the resin and the solvent used in the dispersion liquids 1 to 28 (samples that did not contain the compound represented by General Formula (I)) were used. The maximum absorption wavelength in the obtained optical spectrum was measured. The results are shown in Table 4. The evaluation result from the dispersion liquid 1 corresponds to Examples 1 and 23 to 25, the evaluation results from the dispersion liquids 2 to 22 correspond to Examples 2 to 22, and the evaluation results from the dispersion liquids 23 to 28 correspond to Examples 26 to 31.

(Evaluation Standards)

"A": The maximum absorption wavelength of the material of high refractive index is less than 450 nm.

"B": The maximum absorption wavelength of the material of high refractive index is equal to or longer than 450 nm.

The material of high refractive index means the compound represented by General Formula (I).

<Measurement of Refractive Index>

A 5 cm×5 cm glass substrate, on which an epoxy resin layer was formed using an epoxy resin (JER-827, manufactured by Japan Epoxy Resins Co., Ltd.), was spin-coated with each of the compositions 1 to 31, and then the obtained coating film was baked for 3 minutes at 100° C. Then, by using a high-pressure mercury lamp, the coating film was exposed such that the cumulative exposure amount became 200 mJ/cm$^2$.

By using VASE manufactured by J. A. Woollam, the refractive index of the obtained cured film at a wavelength of 300 to 1,500 nm was measured, and a refractive index $n_{589\ nm}$ at a wavelength 589 nm was measured. Based on the measured refractive index ($n_{589\ nm}$), the compositions were evaluated according to the following evaluation standards. The results are shown in Table 4.

(Evaluation Standards)

"A": The refractive index ($n_{589\ nm}$) is equal to or higher than 1.70.

"B": The refractive index ($n_{589\ nm}$) is equal to or higher than 1.65 and less than 1.70.

"C": The refractive index ($n_{589\ nm}$) is equal to or higher than 1.60 and less than 1.65.

"D": The refractive index ($n_{589\ nm}$) is less than 1.60.

<Evaluation of Exterior Characteristics (Dispersibility)>

The surface of the glass substrate with a cured film obtained in the process of evaluating refractive index characteristics described above was observed with an optical microscope, and the exterior characteristics thereof were evaluated based on the following evaluation standards. The results are shown in Table 4.

(Evaluation Standards)

"A": The surface is smooth and has no problem such as a crack.

"B": Asperities are observed in a portion of the surface but are on a level that is unproblematic for practical use.

"C": Asperities and cracks are observed in a portion of the surface but are on a level that is unproblematic for practical use.

"D": Asperities or cracks are observed in a portion of the surface and are on a level that is problematic for practical use.

<Evaluation of Moisture Resistance>

The glass substrate with a cured film obtained in the process of evaluating refractive index characteristics described above was stored for 720 hours in an atmosphere with a temperature of 85° C. and a relative humidity of 85%. After the storage, the surface condition of the cured film was observed using a Scanning Electron Microscope (SEM) and evaluated based on the following evaluation standards. The results are shown in Table 4.

(Evaluation Standards)

"A": The surface condition does not change before and after the moisture resistance test.

"B": One to five abnormalities (cracking, swelling, and the like) are observed within the surface after the moisture resistance test but are on a level that is unproblematic for practical use.

"C": Six to ten abnormalities (cracking, swelling, and the like) are observed within the surface after the moisture resistance test but are on a level that is unproblematic for practical use.

"D": More than ten abnormalities (cracking, swelling, and the like) are observed within the surface after the moisture resistance test.

<Evaluation of Light Fastness>

By using a xenon lamp, the glass substrate with a cured film obtained in the process of evaluating the refractive index characteristics described above was irradiated with light for 20 hours at 100,000 lux (equivalent to 2,000,000 lux·h), and then the film thickness of the cured film was measured. The smaller the rate of change in film thickness, the better the performance.

The rate of change in film thickness was determined by the following equation based on the film thickness before the light fastness test. Furthermore, based on the rate of change in film thickness, light fastness was evaluated according to the following evaluation standards. The results are shown in Table 4.

(Rate of change in film thickness)={(film thickness before light fastness test)−(film thickness after light fastness test)/(film thickness before light fastness test)}×100

(Evaluation Standards)

"A": The rate of change in film thickness is less than 5%.

"B": The rate of change in film thickness is equal to or higher than 5% and less than 10%.

"C": The rate of change in film thickness is equal to or higher than 10%.

<Developability-Pattern Shape>

A 5 cm×5 cm glass substrate, on which an epoxy resin layer was formed using an epoxy resin (JER-827, manufactured by Japan Epoxy Resins Co., Ltd.), was spin-coated with each of the compositions 1 to 31, and the obtained coating film was baked for 3 minutes at 100° C. Then, by using an i-line stepper exposure machine FPA-3000i5+ (manufactured by Canon Inc.), the coating film was exposed at a wavelength of 365 nm through a mask having a 1 µM island pattern in various exposure amounts within a range of 50 to 1,200 mJ/cm². Thereafter, the glass substrate having the exposed coating film was placed on a horizontal rotating table of a spin-shower developing machine (DW-30 model, manufactured by Chemitronics Co., Ltd.,) and subjected to puddle exposure for 60 seconds at 23° C. by using a developer CD-2000 (manufactured by FUJIFILM Electronic Materials Co., Ltd.), thereby forming a pattern on the glass substrate.

The glass substrate with a pattern formed thereon was fixed on the aforementioned horizontal rotating table by a vacuum chucking method, and the table was caused to rotate at a rotation speed of 50 r.p.m. In this state, a rinsing treatment was performed by supplying pure water thereon in the form of shower from a spray nozzle from above the center of rotation, and then the substrate was spray-dried.

Subsequently, by using a critical dimension SEM "S-9260A" (manufactured by Hitachi High-Technologies Corporation), 100 patterns and 100 developed portions were observed, and the pattern shape and the developability were evaluated based on the following evaluation standards. The results are shown in Table 4.

(Evaluation Standards for Developability)

"A": No residue is checked in developed portions.

"B": Although residues are checked in 1 to 10 developed portions, the developability is unproblematic for practical use.

"C": Residues are checked in 11 or more developed portions.

(Pattern Shape)

"A": A rectangular pattern is formed.

"B": Although 1 to 10 defectively developed portions (non-rectangular portions) are checked at the edge of the pattern, the pattern shape is unproblematic for practical use.

"C": Eleven or more defectively developed portions (non-rectangular portions) are checked at the edge of the pattern.

TABLE 6

| Table 4 | Composition | Spectral characteristics | refractive index | Exterior characteristics (Dispersibility) | Moisture resistance | Light fastness | Develop-ability | Pattern shape |
|---|---|---|---|---|---|---|---|---|
| Example 1 | Composition 1 | A | A | A | A | A | B | A |
| Example 2 | Composition 2 | A | A | A | A | A | A | A |
| Example 3 | Composition 3 | A | A | A | A | A | A | A |

TABLE 6-continued

| Table 4 | Composition | Spectral characteristics | refractive index | Exterior characteristics (Dispersibility) | Moisture resistance | Light fastness | Developability | Pattern shape |
|---|---|---|---|---|---|---|---|---|
| Example 4 | Composition 4 | A | A | A | A | A | A | A |
| Example 5 | Composition 5 | A | A | A | A | A | A | A |
| Example 6 | Composition 6 | A | A | A | A | A | A | A |
| Example 7 | Composition 7 | A | A | A | A | A | A | A |
| Example 8 | Composition 8 | A | A | A | A | A | A | A |
| Example 9 | Composition 9 | A | A | A | A | A | A | A |
| Example 10 | Composition 10 | A | B | B | B | B | B | A |
| Example 11 | Composition 11 | A | B | C | B | B | A | A |
| Example 12 | Composition 12 | A | B | C | B | B | A | A |
| Example 13 | Composition 13 | A | A | A | A | A | A | A |
| Example 14 | Composition 14 | A | C | B | C | B | A | A |
| Example 15 | Composition 15 | A | C | B | C | B | A | A |
| Example 16 | Composition 16 | A | C | B | C | B | A | A |
| Example 17 | Composition 17 | A | C | B | C | B | A | A |
| Example 18 | Composition 18 | A | B | B | B | A | A | A |
| Example 19 | Composition 19 | A | A | A | A | A | A | A |
| Example 20 | Composition 20 | A | A | A | A | B | A | B |
| Example 21 | Composition 21 | A | A | A | A | B | A | B |
| Example 22 | Composition 22 | A | B | B | B | B | B | B |
| Example 23 | Composition 23 | A | A | A | A | B | B | A |
| Example 24 | Composition 24 | A | A | A | A | B | B | A |
| Example 25 | Composition 25 | A | A | A | A | B | B | A |
| Example 26 | Composition 26 | A | A | A | A | A | A | A |
| Example 27 | Composition 27 | A | A | A | A | A | A | A |
| Example 28 | Composition 28 | A | A | A | A | A | A | A |
| Example 29 | Composition 29 | A | A | A | A | A | A | A |
| Example 30 | Composition 30 | A | A | B | B | A | A | A |
| Example 31 | Composition 31 | A | A | B | B | A | A | A |

As is evident from the results in Table 4, according to the composition of the according to the embodiment of the present invention, it is possible to form a film which has a high refractive index and excellent external exterior characteristics.

Furthermore, by comparing Examples 2 to 9, Example 13, Example 19, and Examples 26 to 29 (corresponding to examples graded A in terms of all the evaluation items) with Examples 10 to 12, Examples 14 to 18, Example 22, Example 30, and Example 31, it was confirmed that in a case where A in the compound represented General Formula (I) is a heterocyclic group or in a case where B in the compound represented by General Formula (I) is —$NR^a$—, —$CONR^b$—, or —$SO_2NR^c$—, at least one of refractive index, exterior characteristics, or moisture resistance is further improved. It was confirmed that especially in a case where A in the compound represented by General Formula (I) is a triazine ring group and B in the compound represented by General Formula (I) is —NH—, refractive index, exterior characteristics, and moisture resistance are particularly excellent.

By comparing Examples 2 to 9, Example 13, Example 19, and Examples 26 to 29 (corresponding to examples graded A in terms of all the evaluation items) with Example 1, Example 10, and Examples 22 to 25, it was confirmed that in a case where esters, ketones, or alcohols are used as a solvent, developability is further improved.

By comparing Examples 2 to 9, Example 13, Example 19, and Examples 26 to 29 (corresponding to examples graded A in terms of all the evaluation items) with Examples 20 to 22, it was confirmed that in a case where the dispersant contains a carbon-carbon double bond group, the pattern shape is further improved.

By comparing Examples 2 to 9, Example 13, Example 19, and Examples 26 to 29 (corresponding to examples graded A in terms of all the evaluation items) with Examples 10 to 12, Examples 14 to 17, and Examples 20 to 25, it was confirmed that in a case where an oxime-based initiator is contained as the photopolymerization initiator and/or in a case where a carbon-carbon double bond group is contained in the binder, light fastness is further improved.

What is claimed is:

1. A composition comprising:
a compound represented by General Formula (I);
a solvent; and
a resin
wherein a solubility of the compound represented by General Formula (I) in the solvent is less than 0.5% by mass at 25° C.,
a maximum absorption wavelength of the compound represented by General Formula (I) at a wavelength range of 300 to 800 nm is equal to or shorter than 450 nm, and
the resin is selected from the group consisting of a graft copolymer containing a repeating unit represented by any of General Formula (11) to General Formula (14), and a resin having phosphorus atom-containing group, $$A\text{-}(\text{B-C})_n \qquad (I)$$

in General Formula (I), n represents 2 or 3, A represents a triazine ring group, B represents a single bond, —O—, —NR$^a$—, or —S—, R$^a$ represents a hydrogen atom, an alkyl group, or an aryl group, C represents an alkyl group, an aryl group, or a heterocyclic group, a plurality of B's may be the same as or different from each other, and a plurality of C's may be the same as or different from each other,

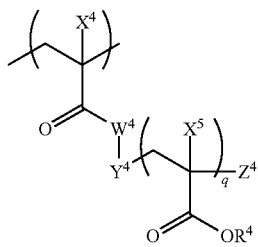

in General Formula (11) to General Formula (14), $W^1$, $W^2$, $W^3$, and $W^4$ each independently represent an oxygen atom or NH, $X^1$, $X^2$, $X^3$, $X^4$, and $X^5$ each independently represent a hydrogen atom or a monovalent group, $Y^1$, $Y^2$, $Y^3$, and $Y^4$ each independently represent a divalent linking group, $Z^1$, $Z^2$, $Z^3$, and $Z^4$ each independently represent a monovalent group, $R^3$ represents an alkylene group, $R^4$ represents a hydrogen atom or a monovalent group, n, m, p, and q each independently represent an integer of 1 to 500, and j and k each independently represent an integer of 2 to 8; in General Formula (13), in a case where p is 2 to 500, a plurality of R3'S may be the same as or different from each other; in General Formula (14), in a case where q is 2 to 500, a plurality of $X^5$'s and R4'S may be the same as or different from each other respectively.

2. The composition according to claim 1,
wherein B is —NR$^a$.

3. The composition according to claim 2,
wherein B is —NH—.

4. The composition according to claim 1,
wherein C is an aryl group or a heterocyclic group.

5. The composition according to claim 1,
wherein the solvent is one or more kinds of solvents selected from the group consisting of esters, alcohols, aromatic hydrocarbons, aliphatic hydrocarbons, nitriles, ketones, and halogen compounds.

6. The composition according to claim 1, further comprising:
a polymerizable compound.

7. The composition according to claim 1, further comprising:
a photopolymerization initiator.

8. The composition according to claim 7,
wherein the photopolymerization initiator is an oxime compound.

9. The composition according to claim 1,
wherein the graft copolymer further contains a carbon-carbon double bond group in a molecule, and the resin having phosphorus atom-containing group further contains a carbon-carbon double bond group in a molecule.

10. A film formed of the composition according to claim 1.

11. A lens formed of the film according to claim 10.

12. A solid-state imaging element comprising:
the lens according to claim 11.

13. A compound represented by General Formula (V),

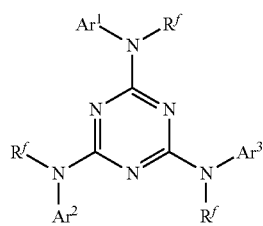
(V)

in General Formula (V), $R^f$ represents a hydrogen atom or an alkyl group, $Ar^1$ to $Ar^3$ each independently represent an aryl group or a heterocyclic group, and at least one of $Ar^1$, $Ar^2$, or $Ar^3$ represents a group represented by General Formula (VI),

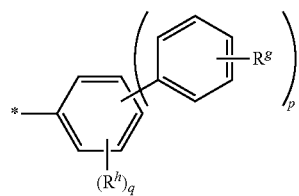
(VI)

in General Formula (VI), $R^g$ represents a phenyl group, a biphenyl group, or a cyano group, $R^h$ represents a substituent, p represents an integer of 1 to 5, q represents an integer of 0 to 4, * represents a binding position, and in a case where there is a plurality of $R^g$'s and a plurality of $R^h$'s, the plurality of $R^g$'s may be the same as or different from each other, and the plurality of $R^h$'s may be the same as or different from each other.

14. A composition comprising:
a compound represented by General Formula (I);
a solvent; and
a resin
wherein a solubility of the compound represented by General Formula (I) in the solvent is less than 0.5% by mass at 25° C.,
a maximum absorption wavelength of the compound represented by General Formula (I) at a wavelength range of 300 to 800 nm is equal to or shorter than 450 nm, and
the resin is selected from the group consisting of a graft copolymer containing a repeating unit represented by any of General Formula (11) to General Formula (14), and a resin having phosphorus atom-containing group,

A—(B-C)$_n$ (I)

in General Formula (I), n represents 3, A represents a triazine ring group, B represents a single bond, —O—, —NR$^a$—, or —S—, R$^a$ represents a hydrogen atom, an alkyl group, or an aryl group, C represents an aryl group, a plurality of B's may be the same as or different from each other, and a plurality of C's may be the same as or different from each other,

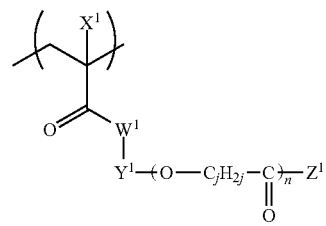
(11)

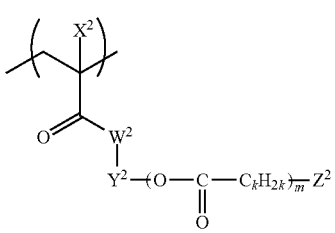
(12)

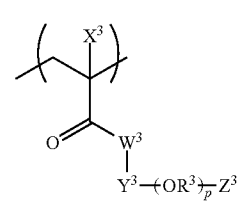
(13)

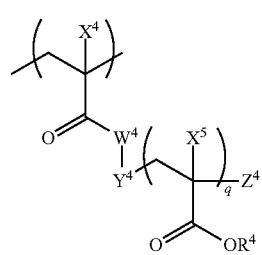
(14)

in General Formula (11) to General Formula (14), $W^1$, $W^2$, $W^3$, and $W^4$ each independently represent an oxygen atom or NH, $X^1$, $X^2$, $X^3$, $X^4$, and $X^5$ each independently represent a hydrogen atom or a monovalent group, $Y^1$, $Y^2$, $Y^3$, and $Y^4$ each independently represent a divalent linking group, $Z^1$, $Z^2$, $Z^3$, and $Z^4$ each independently represent a monovalent group, $R^3$ represents an alkylene group, $R^4$ represents a hydrogen atom or a monovalent group, n, m, p, and q each independently represent an integer of 1 to 500, and j and k each independently represent an integer of 2 to 8; in General Formula (13), in a case where p is 2 to 500, a plurality of $R^3$'s may be the same as or different from each other; in General Formula (14), in a case where q is 2 to 500, a plurality of $X^5$'s and $R^4$'s may be the same as or different from each other respectively.

* * * * *